United States Patent
Bucktrout et al.

(10) Patent No.: US 11,198,735 B2
(45) Date of Patent: Dec. 14, 2021

(54) ANTI-GITR ANTIBODIES AND METHODS OF USE THEREOF

(71) Applicant: Rinat Neuroscience Corp., New York, NY (US)

(72) Inventors: Samantha Lisa Bucktrout, San Francisco, CA (US); Bevin Marie Brady Smith, Scotts Valley, CA (US); Edward Derrick Pascua, Oakland, CA (US); Javier Fernando Chaparro Riggers, San Mateo, CA (US)

(73) Assignee: Rinat Neuroscience Corp., New York, NY (US)

( * ) Notice: Subject to any disclaimer, the term of this patent is extended or adjusted under 35 U.S.C. 154(b) by 177 days.

(21) Appl. No.: 16/488,040

(22) PCT Filed: Feb. 21, 2018

(86) PCT No.: PCT/IB2018/051067
§ 371 (c)(1),
(2) Date: Aug. 22, 2019

(87) PCT Pub. No.: WO2018/158658
PCT Pub. Date: Sep. 7, 2018

(65) Prior Publication Data
US 2020/0031947 A1    Jan. 30, 2020

Related U.S. Application Data

(60) Provisional application No. 62/466,918, filed on Mar. 3, 2017.

(51) Int. Cl.
*C07K 16/28*    (2006.01)
*A61P 35/00*    (2006.01)
*A61K 39/00*    (2006.01)

(52) U.S. Cl.
CPC ........ *C07K 16/2878* (2013.01); *A61P 35/00* (2018.01); *A61K 2039/505* (2013.01); *C07K 2317/52* (2013.01); *C07K 2317/565* (2013.01); *C07K 2317/71* (2013.01); *C07K 2317/732* (2013.01); *C07K 2317/76* (2013.01); *C07K 2317/92* (2013.01)

(58) Field of Classification Search
CPC .......... C07K 2317/76; C07K 2317/565; C07K 2317/92; C07K 16/2878; C07K 2317/52; C07K 2317/71; C07K 2317/732; A61K 2039/505; A61P 35/00
See application file for complete search history.

(56) References Cited

PUBLICATIONS

Coe et al., Cancer Immunol. Immunother., 59(9):1367-77 (2010).
Cohen et al., Cancer Res., 66(9):4904-12 (2006).
Joshi et al., Immunity, 43:1-12 (2015).
Ko et. al. J. Exp. Med. 2005. 202(7): 885-891 (2005).
Lu et al., J. of Translational Medicine, 12:36 (2014).
Mitsui et al., Clinical Cancer Research: an Official Journal of the American Association for Cancer research, 16(10):2781-91 (2010).
Ronchetti et al., Euro. J. of Immunology, 34(3):613-22 (2004).
Ronchetti et al., J. of Immunology, 179:5916-5916 (2007).
Snell et al., Immunological Reviews, 244(1):197-217 (2011).
Tone et al. Proc. Natl. Acad. Sci., 100(25): 15059-15064 (2003).

*Primary Examiner* — Ruixiang Li
(74) *Attorney, Agent, or Firm* — Pfizer Inc.

(57) ABSTRACT

The present invention provides antibodies that bind Glucocorticoid Induced Tumor necrosis factor Receptor family related protein (GITR) and methods of using same. The anti-GITR antibodies can be used therapeutically alone or in combination with other therapeutics to treat cancer and other diseases.

6 Claims, 23 Drawing Sheets
Specification includes a Sequence Listing.

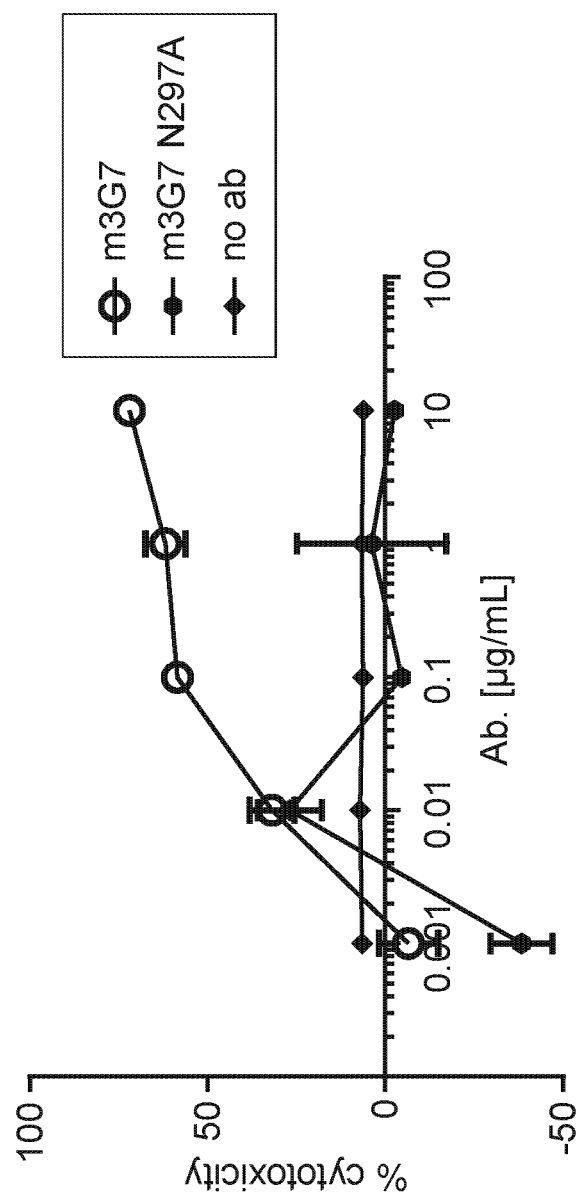

Parent Jurkat

GITR+ low

GITR+ high

10H2 1μg/ml

Mouse IgG 5μg/ml

IgG2a Isotype Control
5 mpk

21B6 IgG2a 0.2 mpk

21B6 IgG2a 1mpk

21B6 IgG2a 5mpk

Figure 7J Tumor CD8+T cell: Treg
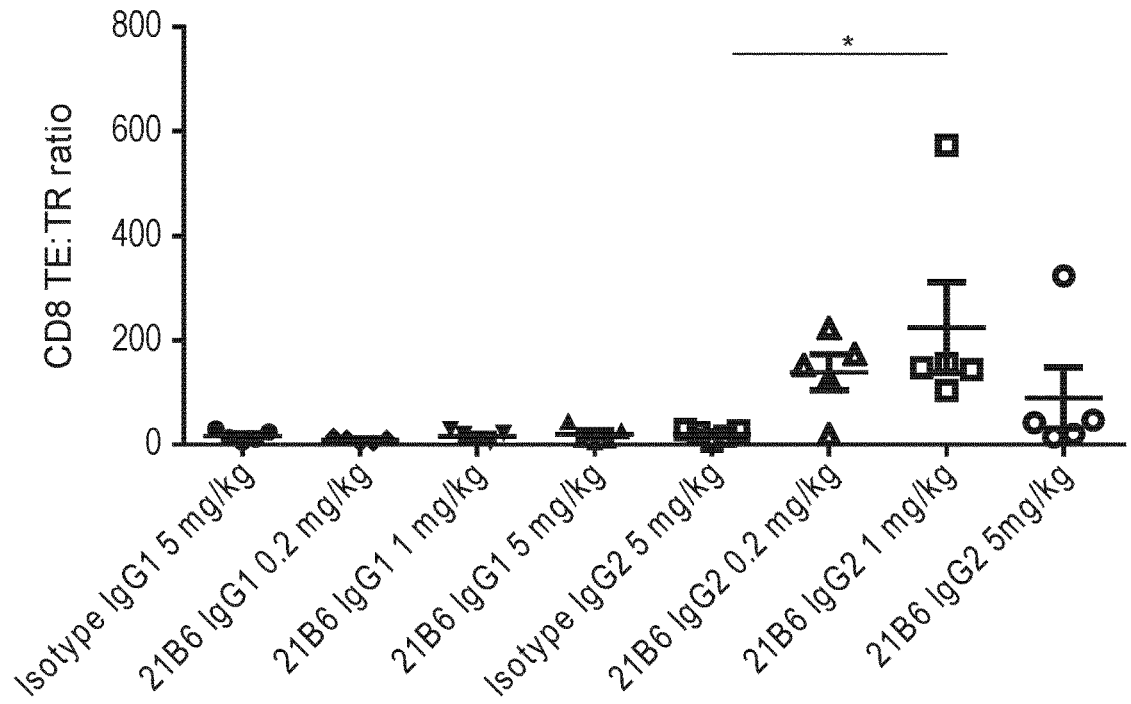
Figure 7K Tumor CD4+Teff: Treg
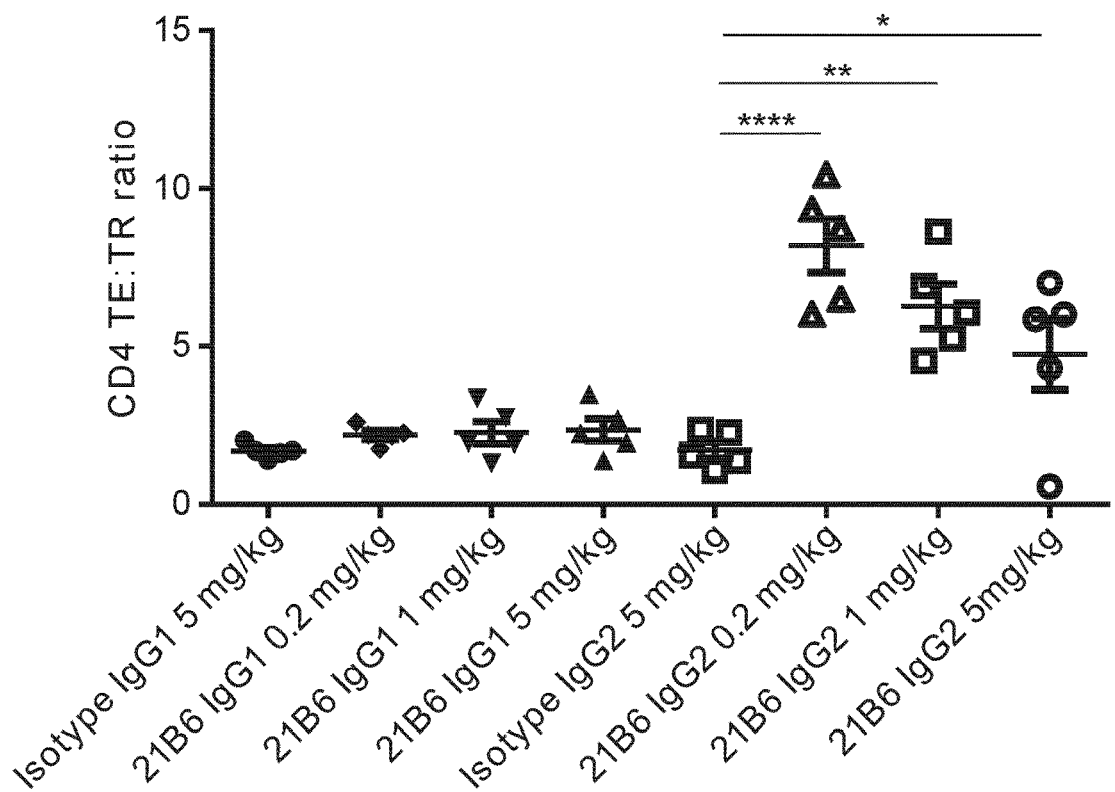

ANTI-GITR ANTIBODIES AND METHODS OF USE THEREOF

CROSS-REFERENCE TO RELATED APPLICATIONS

This application is the U.S. National Phase of International Application No. PCT/IB2018/051067, filed Feb. 21, 2018, which claims the benefit of U.S. provisional application No. 62/466,918, filed Mar. 3, 2017. The complete content of all of the above-referenced patent applications are hereby incorporated by reference for all purposes.

SEQUENCE LISTING INCORPORATED BY REFERENCE

This application contains a Sequence Listing which has been submitted electronically in ASCII format and is hereby incorporated by reference in its entirety. Said ASCII copy, created on Aug. 8, 2019, is named PC72321A_Sequence_Listing.txt and is 69,203 bytes in size.

FIELD

The present invention relates to antibodies, e.g., full length antibodies that bind Glucocorticoid Induced Tumor necrosis factor Receptor family related protein (GITR). The invention further relates to compositions comprising antibodies to GITR, and methods of using anti-GITR antibodies as a medicament. Certain embodiments relate to methods of using anti-GITR antibodies for the treatment, prevention and/or diagnosis of various diseases, including hyperproliferative disease, such as cancer.

BACKGROUND

Glucocorticoid induced tumor necrosis factor receptor family related protein (GITR) is expressed on the surface of NK cells and T cells, including CD8$^+$, CD4$^+$, or regulatory T cells (Treg). Tregs express GITR at higher levels than other types of CD4$^+$ T cells or CD8$^+$ T cells. Expression of GITR is low and on minor populations of Tregs in peripheral blood, whereas Treg infiltrating solid tumors have increased GITR expression on the majority of Tregs.

Signaling via GITR increases T cell proliferation and effector functions and also protects T cells from activation-induced cell death (AICD), which in turn increases the frequency of memory T cells. See, e.g., Ronchetti et al., Euro. J. of Immunology. 34(3):613-22 (2004); and Snell et al., Immunological Reviews. 244(1):197-217 (2011). Previous studies have shown that an agonist anti-GITR monoclonal antibody (mAb) has anti-tumor efficacy in multiple mouse syngeneic tumor models, including Meth A fibrosarcoma, CT26 colon carcinoma, and MB49 bladder carcinoma. See, e.g., Joshi et al., Immunity, 43:1-12 (2015); and Ronchetti et al., J. of Immunology, 179:5916-5916 (2007). This efficacy has been shown to correspond with enhanced responsiveness of effector T cells. See, e.g., Ko et al., J. Exp. Med. 202(7):885-891 (2005); Coe et al., Cancer Immunol. Immunother., 59(9):1367-77 (2010); and Cohen et al., Cancer Res., 66(9):4904-12 (2006). GITR agonists have also shown synergistic anti-tumor effect with an anti-CTLA-4 antibody and an anti-PD-1 antibody. See, e.g., Mitsui et al., Clinical Cancer Research: an Official Journal of the American Association for Cancer research, 16(10):2781-91 (2010); and Lu et al., J. of Translational Medicine, 12:36 (2014). Accordingly, development of an antibody-based therapeutic agent that modulates GITR signaling would be of great value in treatments of cancer.

SUMMARY

The invention disclosed herein is directed to antibodies that selectively bind to GITR. It is demonstrated that the anti-GITR antibodies of the present invention have the dual properties of Treg depletion and T effector cell activation, which in turn resulting in enhanced T effector to Treg ratio in tumors and tumor regression in patients.

In one aspect, the invention provides an isolated antibody that specifically binds to GITR and comprises: a heavy chain variable region (VH) comprising a VH complementarity determining region one (CDR1), VH CDR2, and VH CDR3 of the VH having an amino acid sequence selected from the group consisting of SEQ ID NO: 2, 4, 6, 8, 10, 12, 14, or 112; and/or a light chain variable region (VL) comprising a VL CDR1, VL CDR2, and VL CDR3 of the VL having an amino acid sequence selected from the group consisting of SEQ ID NO: 1, 3, 5, 7, 9, 11, 13, or 111. In some embodiments, the antibody comprises a VH region produced by the expression vector with ATCC Accession No. PTA-123632. In some embodiments, the antibody comprises a VL region produced by the expression vector with ATCC Accession No. PTA-123633.

In some embodiments, the antibody comprises a VH CDR1 comprising the amino acid sequence of SEQ ID NO: 24, 25, 26, 32, 33, 34, 35, 39, 40, 41, 115, 116, 117, 63, 64, 65, a VH CDR2 comprising the amino acid sequence of SEQ ID NO: 27, 28, 44, 45, 66, or 67, and a VH CDR3 comprising the amino acid sequence shown in SEQ ID NO: 29, 46, or 68; and/or a VL CDR1 comprising the amino acid sequence shown in SEQ ID NO: 21, 30, 36, 42, 113, or 31, a VL CDR2 comprising the amino acid sequence shown in SEQ ID NO: 22, 37, 43, 114, or 61, and a VL CDR3 comprising the amino acid sequence shown in SEQ ID NO: 23, 38, or 62. In some embodiments, the antibody comprises a VH comprising the amino acid sequence shown in SEQ ID NO: 2, 4, 6, 8, 10, 12, 14, or 112, or a variant thereof with one or several conservative amino acid substitutions in residues that are not within a CDR. In some embodiments, the antibody comprises a VL comprising the amino acid sequence shown in SEQ ID NO: 1, 3, 5, 7, 9, 11, 13, or 111, or a variant thereof with one or several amino acid substitutions in amino acids that are not within a CDR. In some embodiments, the antibody comprises a VH comprising the amino acid sequence shown in SEQ ID NO: 2, 4, 6, 8, 10, 12, 14, or 112, and a VL comprising the amino acid sequence shown in SEQ ID NO: 1, 3, 5, 7, 9, 11, 13, or 111.

In another aspect, the invention provides an isolated antibody that specifically binds to GITR and comprises: a VH comprising a VH CDR1, VH CDR2, and VH CDR3 of the VH having an amino acid sequence selected from the group consisting of SEQ ID NO: 16, 18, 20, 121, and 123; and/or a VL comprising a VL CDR1, VL CDR2, and VL CDR3 of the VL having an amino acid sequence selected from the group consisting of SEQ ID NO: 15, 17, 19, 120, and 122. In some embodiments, the antibody comprises a VH CDR1 comprising the amino acid sequence of SEQ ID NO: 50, 51, 52, 56, or 57, a VH CDR2 comprising the amino acid sequence of SEQ ID NO: 53, 54, 58, or 59, and a VH CDR3 comprising the amino acid sequence shown in SEQ ID NO: 55, 60, or 124; and/or a VL CDR1 comprising the amino acid sequence shown in SEQ ID NO: 47, a VL CDR2 comprising the amino acid sequence shown in SEQ ID NO: 48, and a VL CDR3 comprising the amino acid sequence shown in SEQ ID NO: 49.

In another aspect, the invention provides an isolated antibody that specifically binds to GITR and comprises: a VH comprising a VH CDR1, VH CDR2, and VH CDR3 of the VH having an amino acid sequence selected from the group consisting of SEQ ID NO: 70 and 72; and/or a VL comprising a VL CDR1, VL CDR2, and VL CDR3 of the VL having an amino acid sequence selected from the group consisting of SEQ ID NO: 69 and 71. In some embodiments, the antibody comprises a VH CDR1 comprising the amino acid sequence of SEQ ID NO: 32, 76, 77, 84, 85, or 86, a VH CDR2 comprising the amino acid sequence of SEQ ID NO: 78 or 79, and a VH CDR3 comprising the amino acid sequence shown in SEQ ID NO: 80 or 87; and/or a VL CDR1 comprising the amino acid sequence shown in SEQ ID NO: 73 or 81, a VL CDR2 comprising the amino acid sequence shown in SEQ ID NO: 74 or 82, and a VL CDR3 comprising the amino acid sequence shown in SEQ ID NO: 75 or 83.

In some embodiments, the antibody can be a human antibody, a humanized antibody, or a chimeric antibody. In some embodiments, the antibody is a monoclonal antibody.

In some embodiments, the antibody comprises a constant region. In some embodiments, the antibody is of the human IgG$_1$, IgG$_2$, IgG$_{2\Delta a}$, IgG$_3$, IgG$_4$, IgG$_{4\Delta b}$, IgG$_{4\Delta c}$, IgG$_4$ S228P, IgG$_{4\Delta b}$ S228P, and IgG$_{4\Delta c}$ S228P subclass. In some embodiments, the antibody is of the IgG1 isotype.

In another aspect, the invention provides an isolated antibody which specifically binds to GITR and competes with and/or binds to the same or overlaps with the GITR epitope recognized by the anti-GITR antibodies as described herein.

In some embodiments, an anti-GITR antibody provided herein promotes Treg depletion and activates T effector cells (e.g., as measured in vivo using a syngeneic tumor model in CT26 cells).

In some embodiments, an anti-GITR antibody provided herein increases the release of the inflammatory cytokines IFNγ and TNFα from effector T cells (e.g., as measured in vitro in CD4+ and CD8+ T cells).

In some embodiments, an anti-GITR antibody provided herein enhances anti-tumor immune responses (e.g., inhibiting tumor growth, and enhancing the effects on non-T cells such as NK and other innate cells).

In some embodiments, an anti-GITR antibody provided herein binds human GITR.

In another aspect, the invention provides a pharmaceutical composition comprising a therapeutically effective amount of an anti-GITR antibody as described herein and a pharmaceutically acceptable carrier.

In another aspect, the invention provides an isolated polynucleotide comprising a nucleotide sequence encoding an anti-GITR antibody as described herein. In another aspect, the invention provides a vector comprising the polynucleotide.

In another aspect, the invention provides an isolated host cell that recombinantly produces an anti-GITR antibody as described herein.

In another aspect, the invention provides a method of producing an anti-GITR antibody, the method comprising: culturing a cell line that recombinantly produces the antibody as described herein under conditions wherein the antibody is produced; and recovering the antibody.

In another aspect, the invention provides a method of producing an anti-GITR antibody, the method comprising: culturing a cell line comprising nucleic acid encoding an antibody comprising a heavy chain comprising the amino acid sequence shown in SEQ ID NO: 110 and a light chain comprising the amino acid sequence shown in SEQ ID NO: 109 under conditions wherein the antibody is produced; and recovering the antibody.

In some embodiments, the heavy and light chains are encoded on separate vectors. In other embodiments, heavy and light chains are encoded on the same vector.

In another aspect, the invention provides a method for treating a condition in a subject comprising administering to the subject in need thereof an effective amount of the pharmaceutical composition as described herein. In some embodiments, the condition is a cancer. In some embodiments, the cancer is selected from the group consisting of B-cell related cancer, gastric cancer, small intestine cancer, sarcoma, head and neck cancer, thymic cancer, epithelial cancer, salivary cancer, liver cancer, biliary cancer, neuroendocrine tumors, stomach cancer, thyroid cancer, lung cancer, mesothelioma, ovarian cancer, breast cancer, prostate cancer, esophageal cancer, pancreatic cancer, glioma, renal cancer, bladder cancer, cervical cancer, uterine cancer, vulvar cancer, penile cancer, testicular cancer, anal cancer, choriocarcinoma, colorectal cancer, oral cancer, skin cancer, Merkel cell carcinoma, glioblastoma, brain tumor, bone cancer, eye cancer, and melanoma.

In some embodiments, the B-cell related cancer is selected from the group consisting of multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other B-cell related lymphoma.

In some embodiments, the cancer is relapsed or refractory.

In some embodiments, the cancer is locally advanced or metastatic melanoma, squamous cell head and neck cancer (SCHNC), ovarian cancer, renal cancer, gastric cancer, or lung cancer.

In another aspect, the invention provides a method of inhibiting tumor growth or progression in a subject who has a tumor, comprising administering to the subject an effective amount of the pharmaceutical composition as described herein.

In another aspect, the invention provides a method of inhibiting or preventing metastasis of cancer cells in a subject, comprising administering to the subject in need thereof an effective amount of the pharmaceutical composition as described herein.

In another aspect, the invention provides a method of inducing tumor regression in a subject who has a GITR expressing tumor, comprising administering to the subject an effective amount of the pharmaceutical composition as described herein.

In some embodiments, the antibody herein can be administered parenterally in a subject. In some embodiments, the subject is a human.

In some embodiments, the method can further comprise administering an effective amount of a second therapeutic agent. In some embodiments, the second therapeutic agent is a biotherapeutic agent, for example, an antibody, including but not limited to, an anti-CTLA-4 antibody, an anti-4-1BB antibody, an anti-PD-1 antibody, an anti-PD-L1 antibody, an anti-TIM3 antibody, an anti-LAG3 antibody, an anti-TIGIT antibody, an anti-OX40 antibody, an IL-8 antibody, an anti-HVEM antibody, an anti-BTLA antibody, an anti-CD40 antibody, an anti-CD40L antibody, anti-CD47 antibody, an anti-CSF1R antibody, an anti-CSF1 antibody, an anti-MARCO antibody, an anti-CXCR4 antibodies, an anti-VEGFR1 antibody, an anti-VEGFR2 antibody, an anti-TNFR1 antibody, an anti-TNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD 52 antibody, an anti-CCR4 antibody, an anti-CCR8 antibody, an anti-CD200R antibody, an anti-VISG4 antibody, an anti-CCR2 antibody, an anti-LILRb2 antibody, an anti-CXCR4 antibody, an anti-CD206 antibody, an anti-CD163 antibody, an anti-KLRG1 antibody, an anti-FLT3 antibody, an anti-B7-H4 antibody, an anti-B7-H3 antibody, or a second anti-GITR antibody.

In some embodiments, the second therapeutic agent is a TNFα, a PAP inhibitor, an oncolytic virus, a kinase inhibitor, an ALK inhibitor (e.g., sunitinib or crizotinib), a MEK inhibitor, an IDO inhibitor, a GLS1 inhibitor, a tyrosine kinase inhibitor (e.g., axitinib or palbociclib), a CAR (Chimeric Antigen Receptor)-T cell or T cell therapy, a TLR (Toll-Like Receptor) Agonist (e.g., TLR3, TLR4, TLR5, TLR7, TLR9), or a tumor vaccine.

Also provided is the use of any of the anti-GITR antibodies provided herein in the manufacture of a medicament for the treatment of cancer or for inhibiting tumor growth or progression in a subject in need thereof.

BRIEF DESCRIPTION OF THE FIGURES/DRAWINGS

FIG. 4C shows that GITR antibodies mediate cell cytotoxicity in the in vitro assay of antibody-dependent cell phagocytosis (ADCP) mediated by macrophages.

Figure 5A:
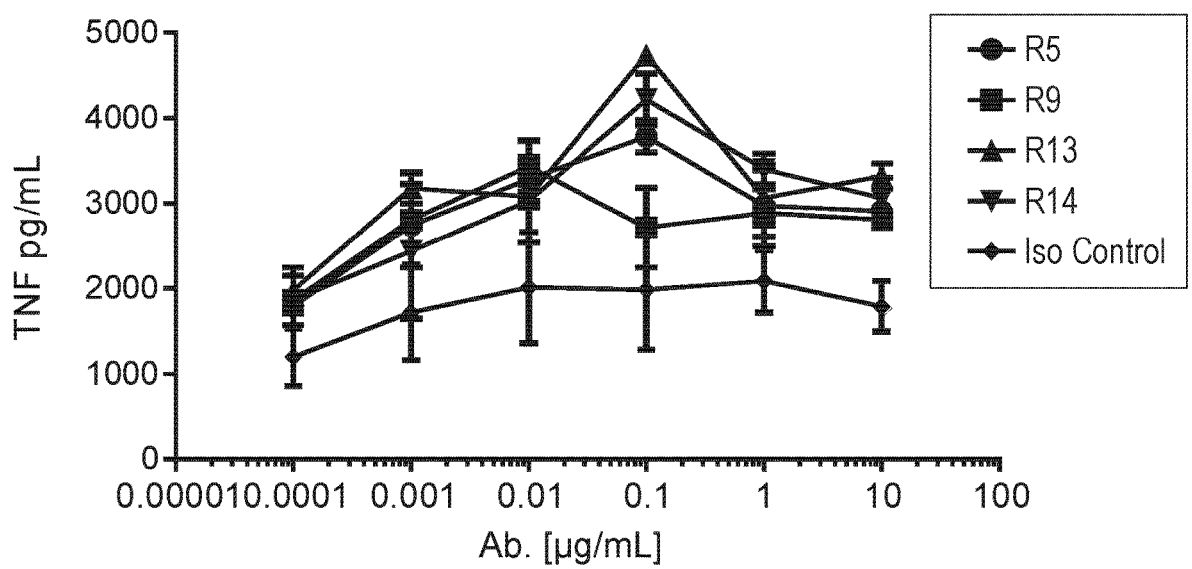
FIG. 5A shows a graph summarizing that the GITR antibodies of the present invention (h3G7 R5 ("R5"), h3G7 R9 ("R9"), h10H2 R13 ("R13"), and h10H2 R14 ("R14")) caused enhanced secretion of TNFα from the GITR+3A9 cells in a dose dependent manner when plate bound.
Figure 5B:
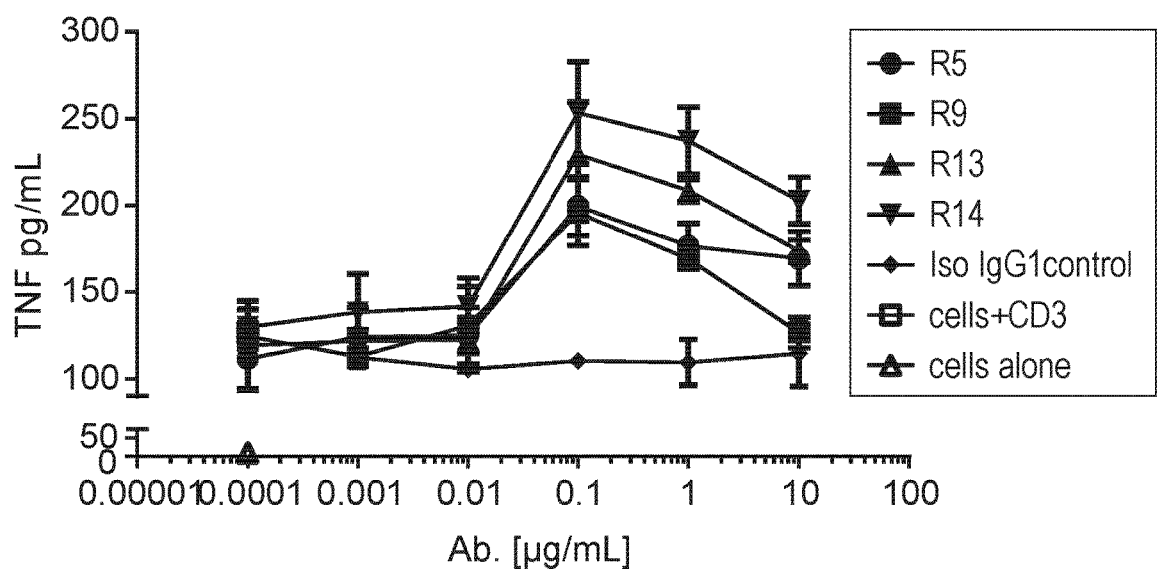

FIG. 5B also shows a graph summarizing that soluble anti-GITR antibodies R5, R9, R13, and R14 enhanced secretion of TNFα between in GITR+3A9 cells co-cultured with the B cell lymphoma line (LK35.2).

Figure 5C:
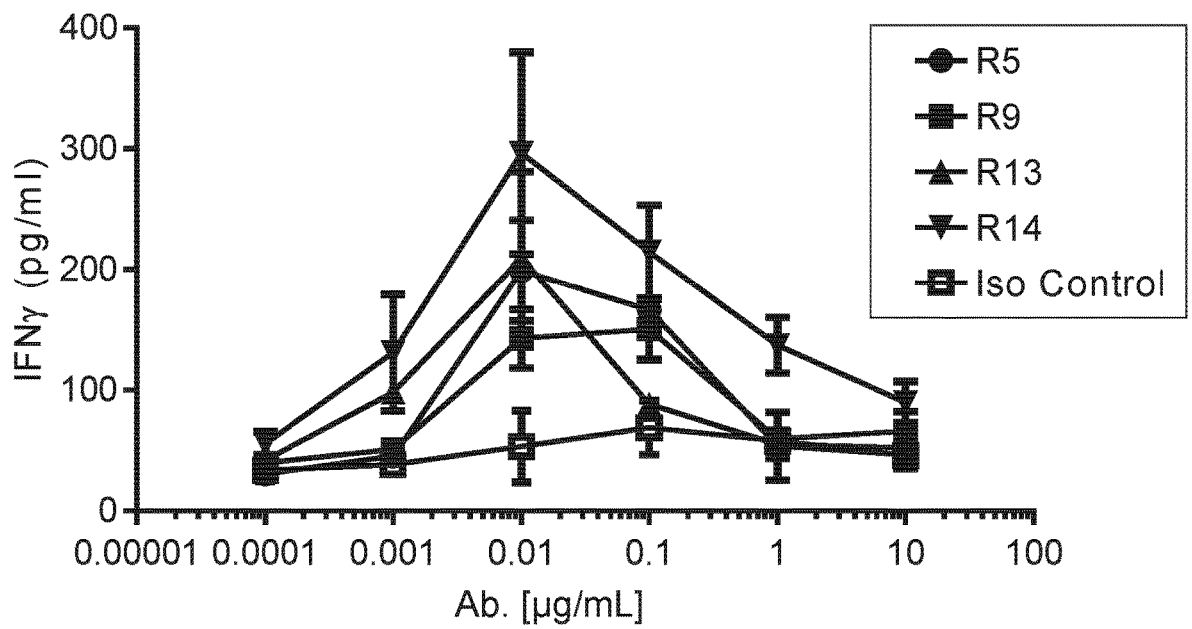

FIG. 5C shows that plate-bound anti-GITR antibodies R5, R9, R13 and R14 caused dose dependent increases in secreted IFNγ, from human blood CD4+ and CD8+ T cells activated with anti-CD3 antibody.

Figure 5D:
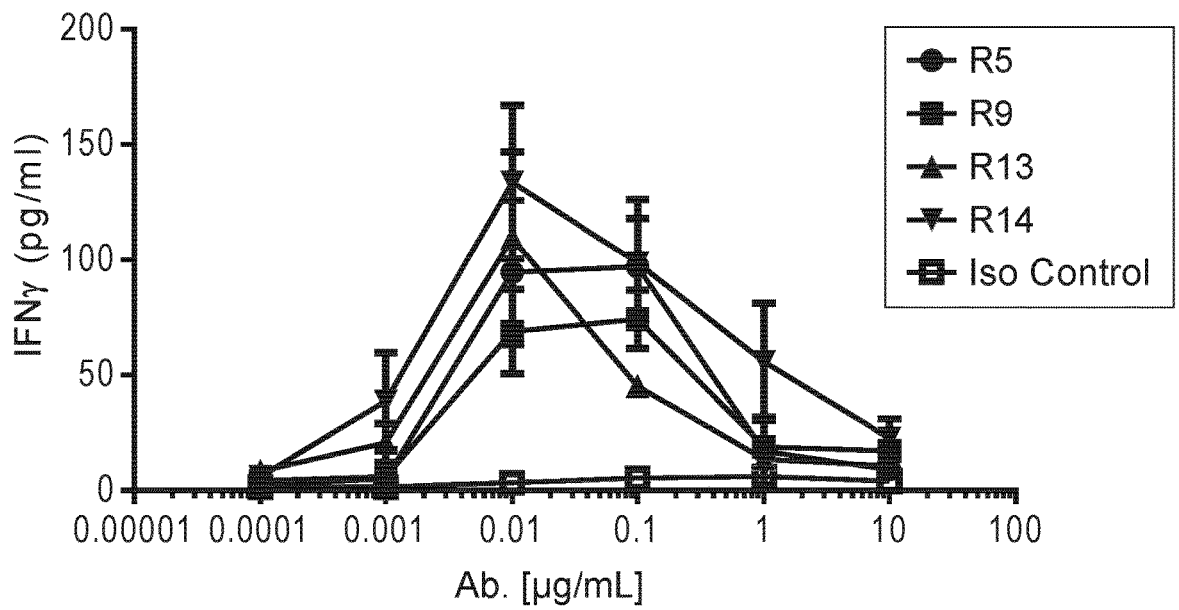

FIG. 5D shows that plate-bound anti-GITR antibodies R5, R9, R13, and R14 caused dose dependent increases in secreted TNFα from human blood CD4+ and CD8+ T cells activated with anti-CD3 antibody.

Figure 6A:
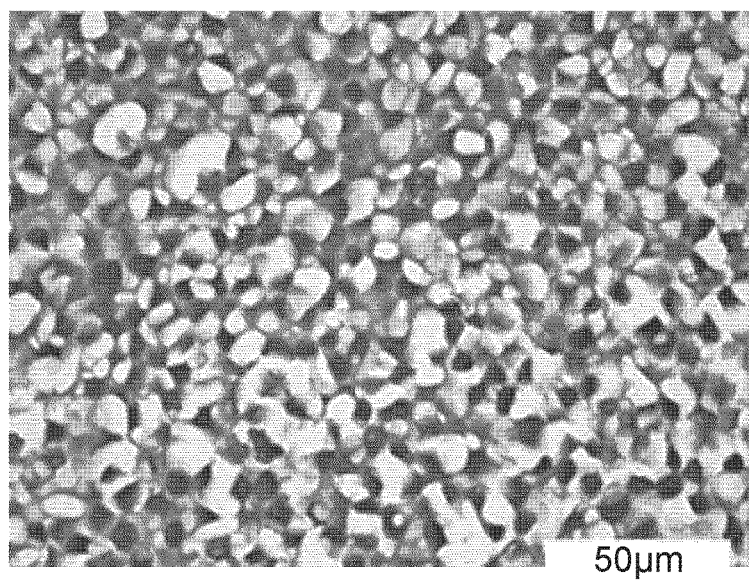
Figure 6B:
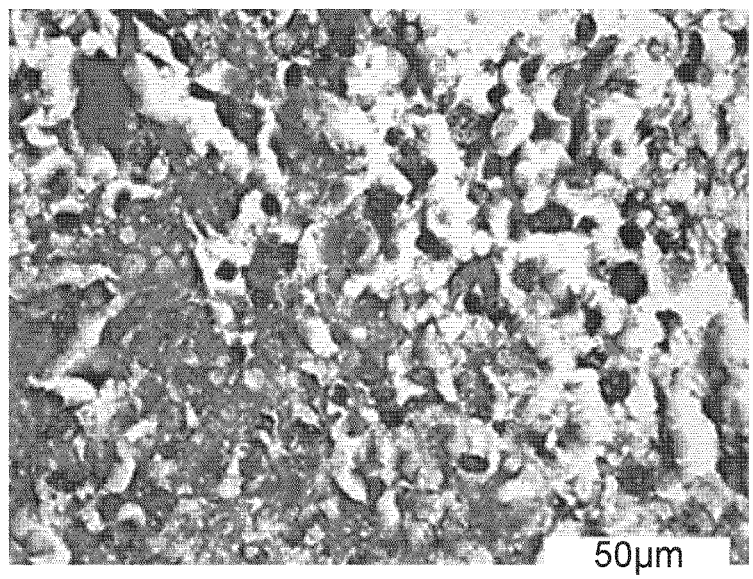
Figure 6C:
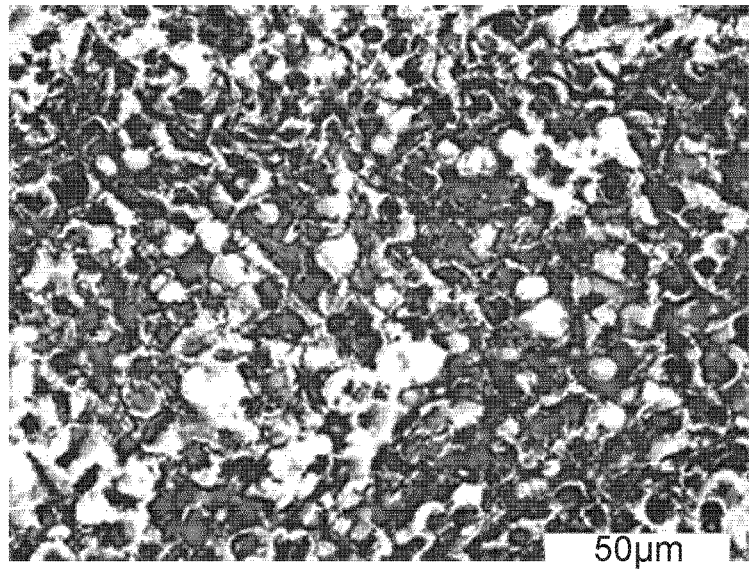

FIG. 6A, FIG. 6B, and FIG. 6C show correlated density of the staining of T cell lines expressing (A) no, (B) low and (C) high human GITR with the anti-GITR antibody m10H2.

Figure 6D:
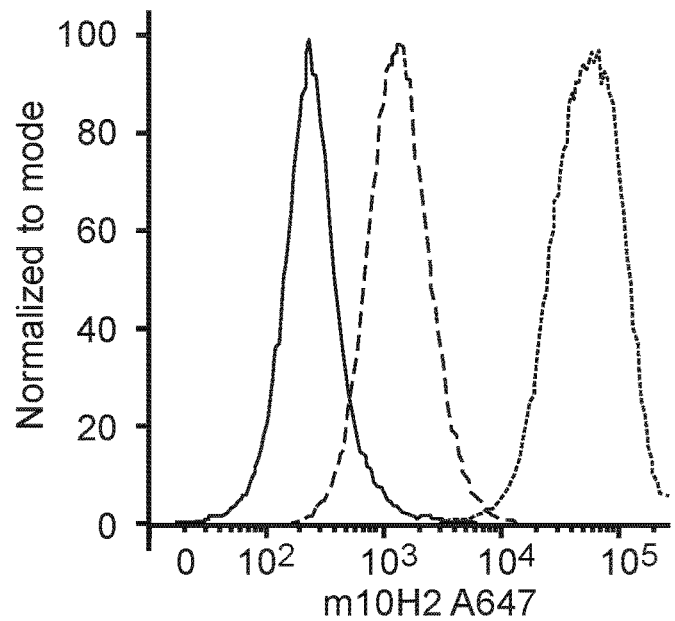

FIG. 6D shows the anti-GITR m10H2 antibody flow cytometry staining of the no, low, and high GITR-expressing cell lines described in FIG. 6A.

Figure 6E:
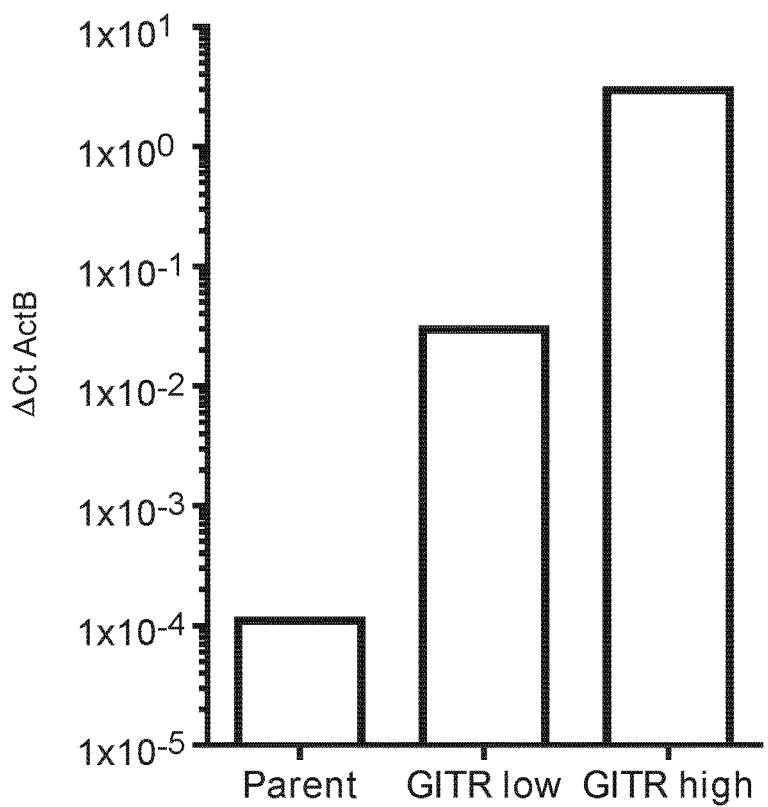

FIG. 6E shows the quantitative PCR and normalization to actin B expression of T cell lines expressing no, low and high human GITR.

Figure 6F:
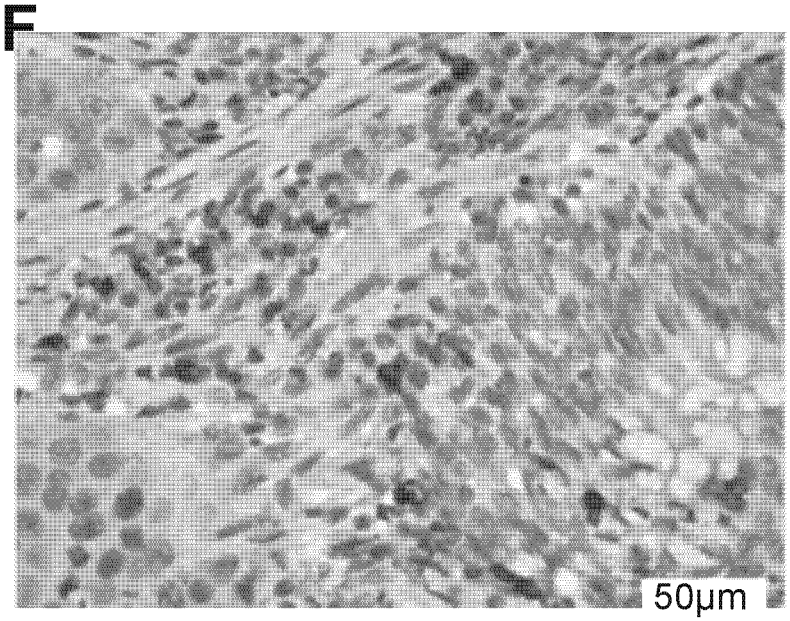

FIG. 6F shows the staining of FFPE (Formalin Fixed Paraffin Embedded) tissues isolated from NSCLC tumors with m10H2.

Figure 6G:
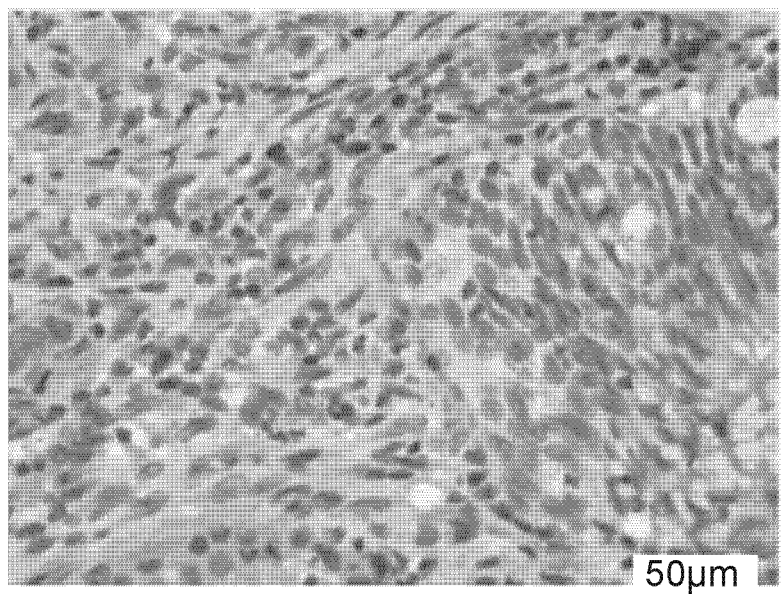

FIG. 6G shows the staining of FFPE tissues isolated from NSCLC tumors with isotype control mouse antibody.

FIG. 7A-FIG. 7D show the tumor growth of individual mice treated with 5 mpk (mg/kg) of mIgG2a isotype control, 0.2, 1 and 5 mpk (mg/kg) of the anti-GITR 21B6 mouse(m) Fc IgG2a, respectively.

FIG. 7E-FIG. 7H show the tumor growth of individual mice treated with 5 mpk (mg/kg) of mIgG2l isotype control, 0.2, 1 and 5 mpk (mg/kg) of the anti-GITR 21B6 mouse(m) Fc IgG1, respectively.

Figure 7A:
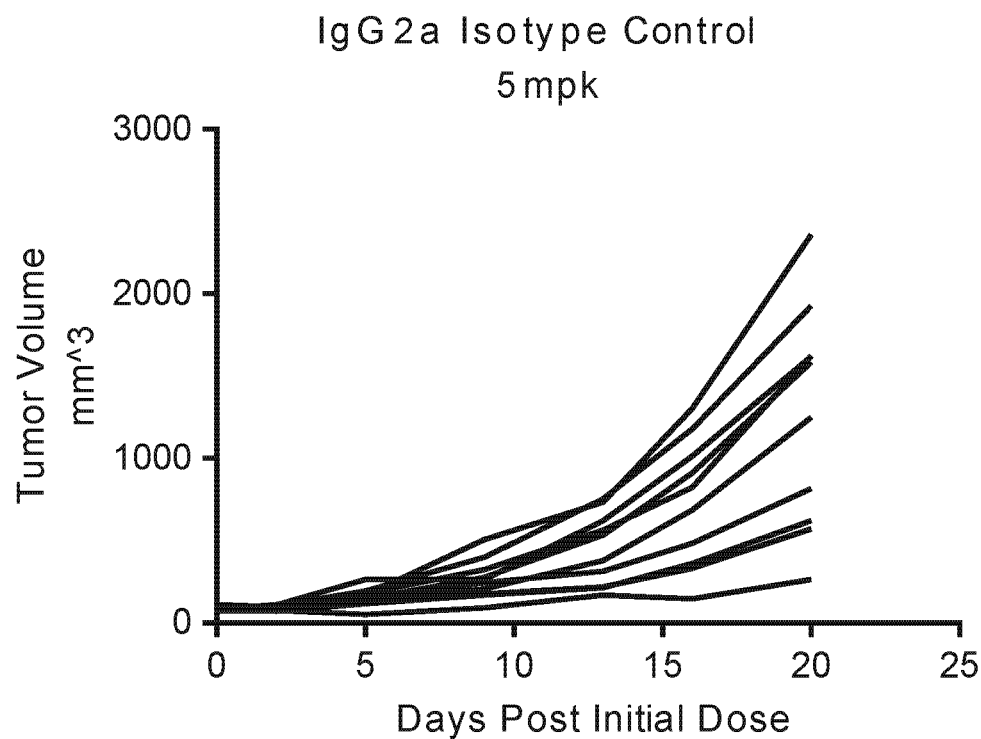
Figure 7B:
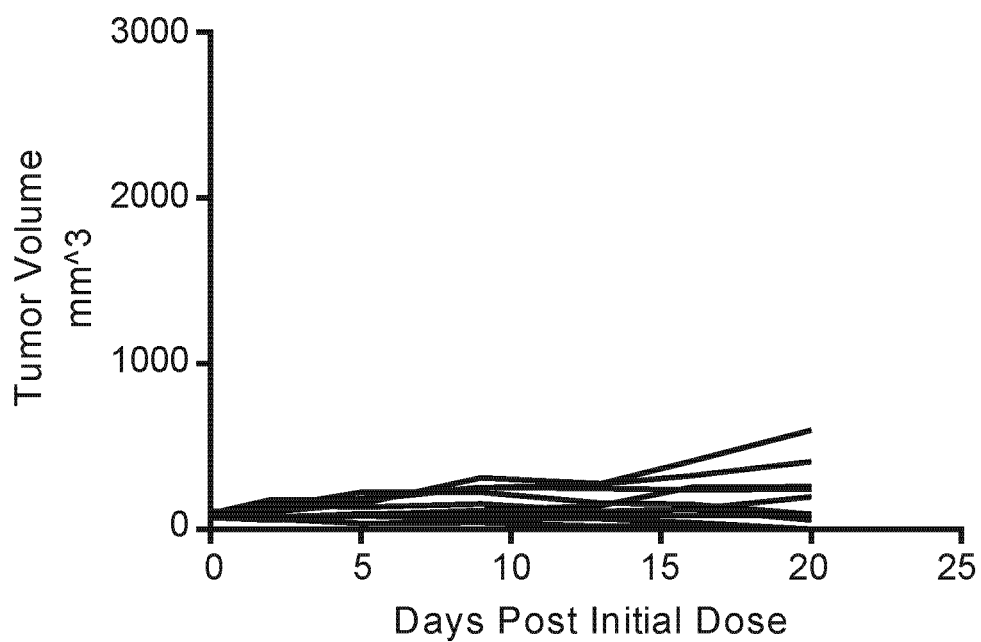
Figure 7C:
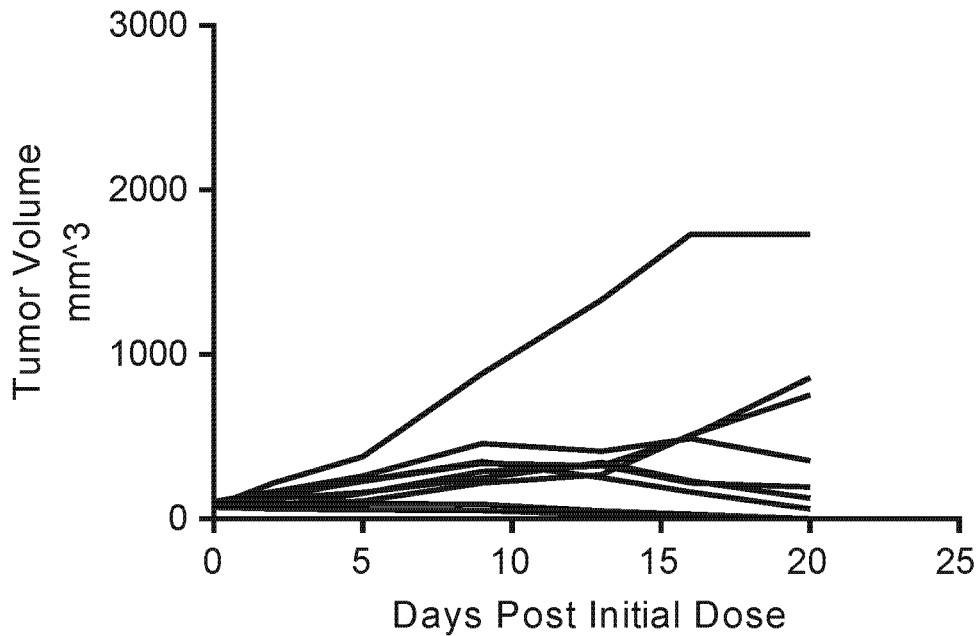
Figure 7D:
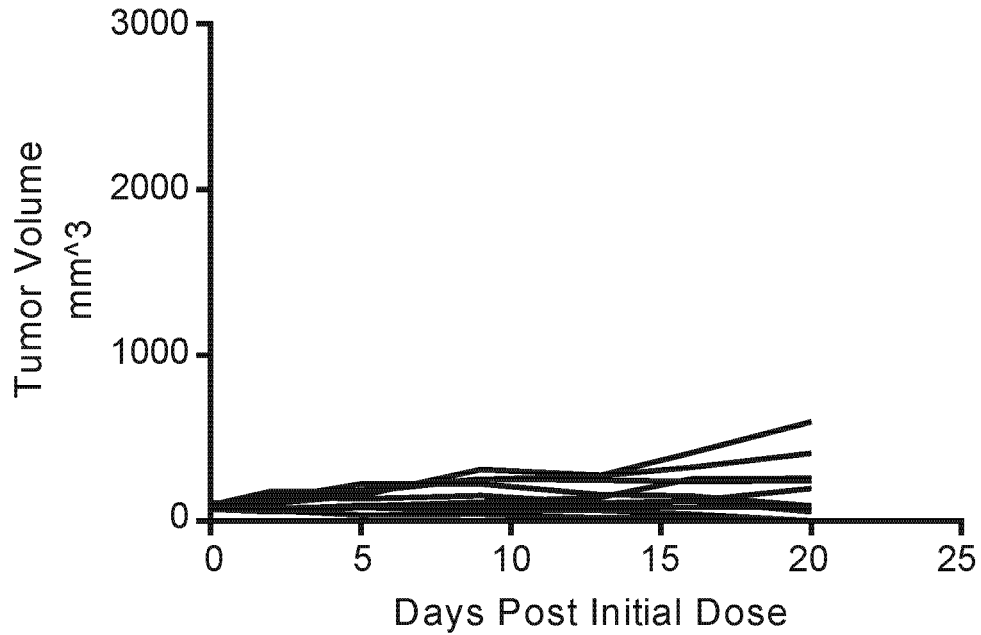
Figure 7E:
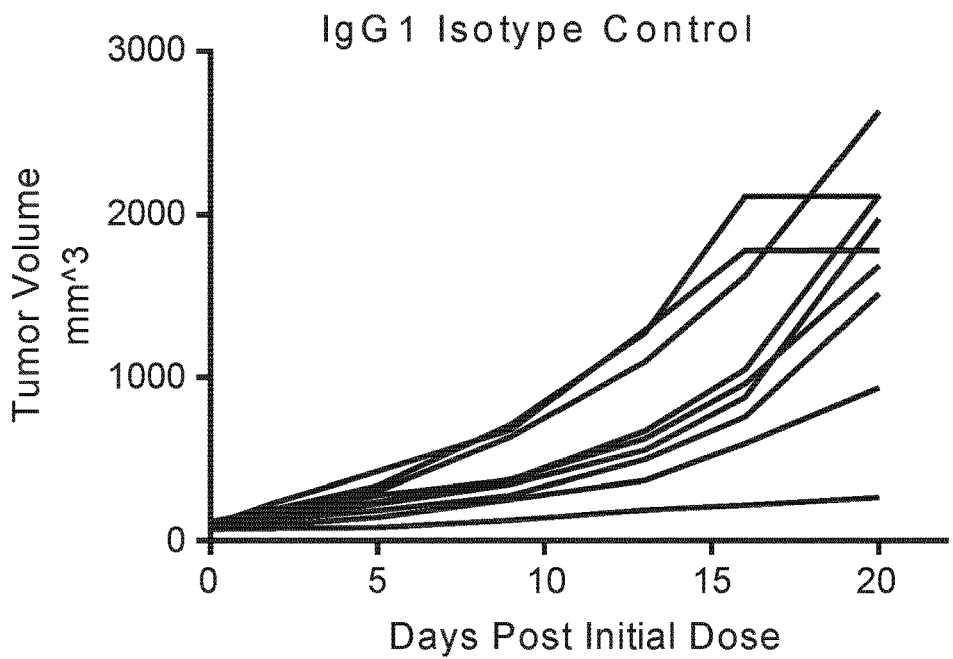
Figure 7F:
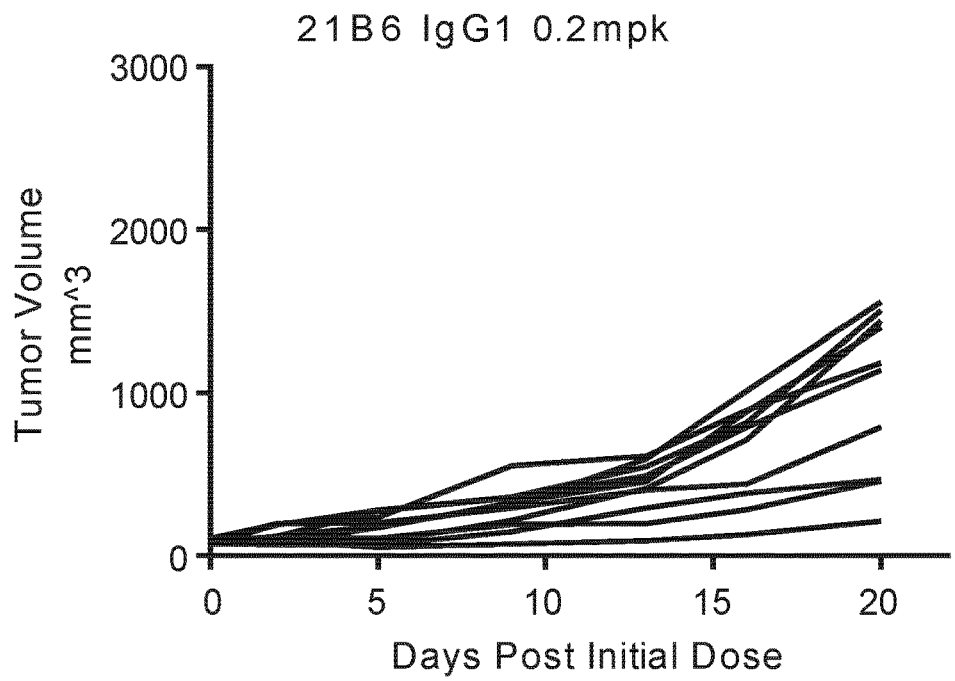
Figure 7G:
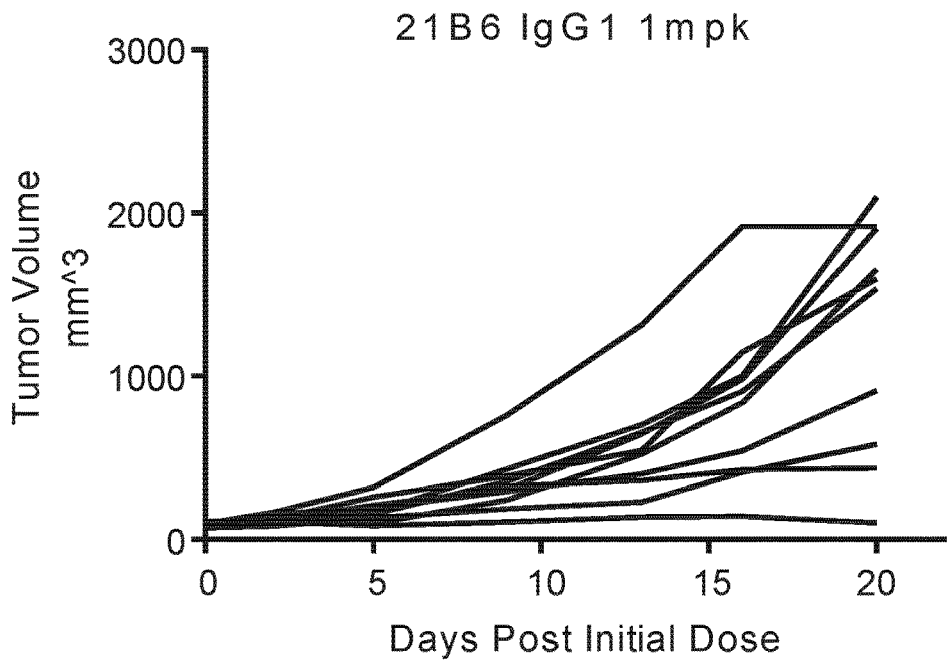
Figure 7H:
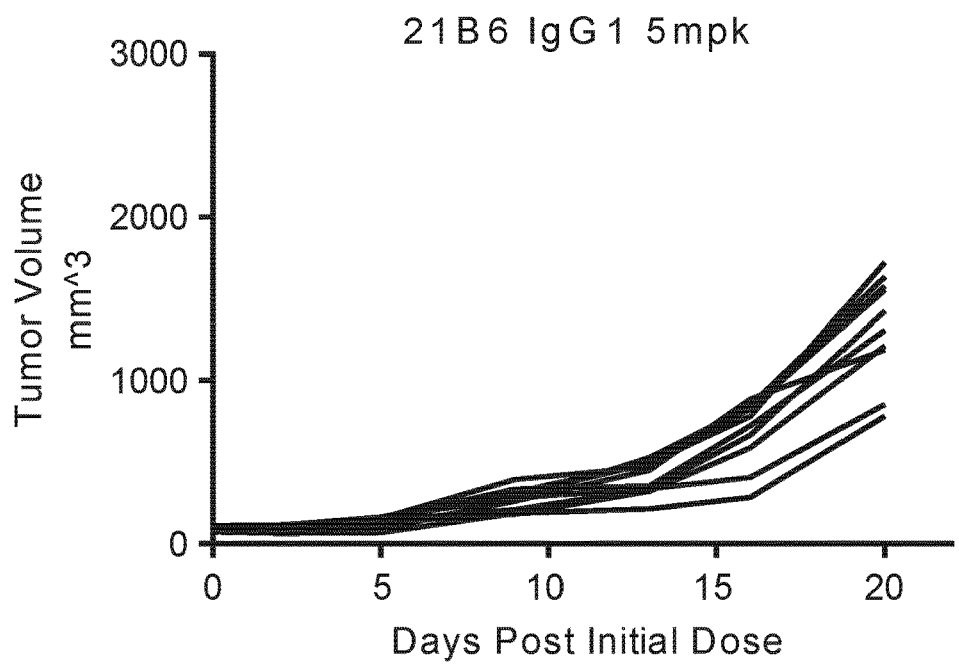
Figure 7I:
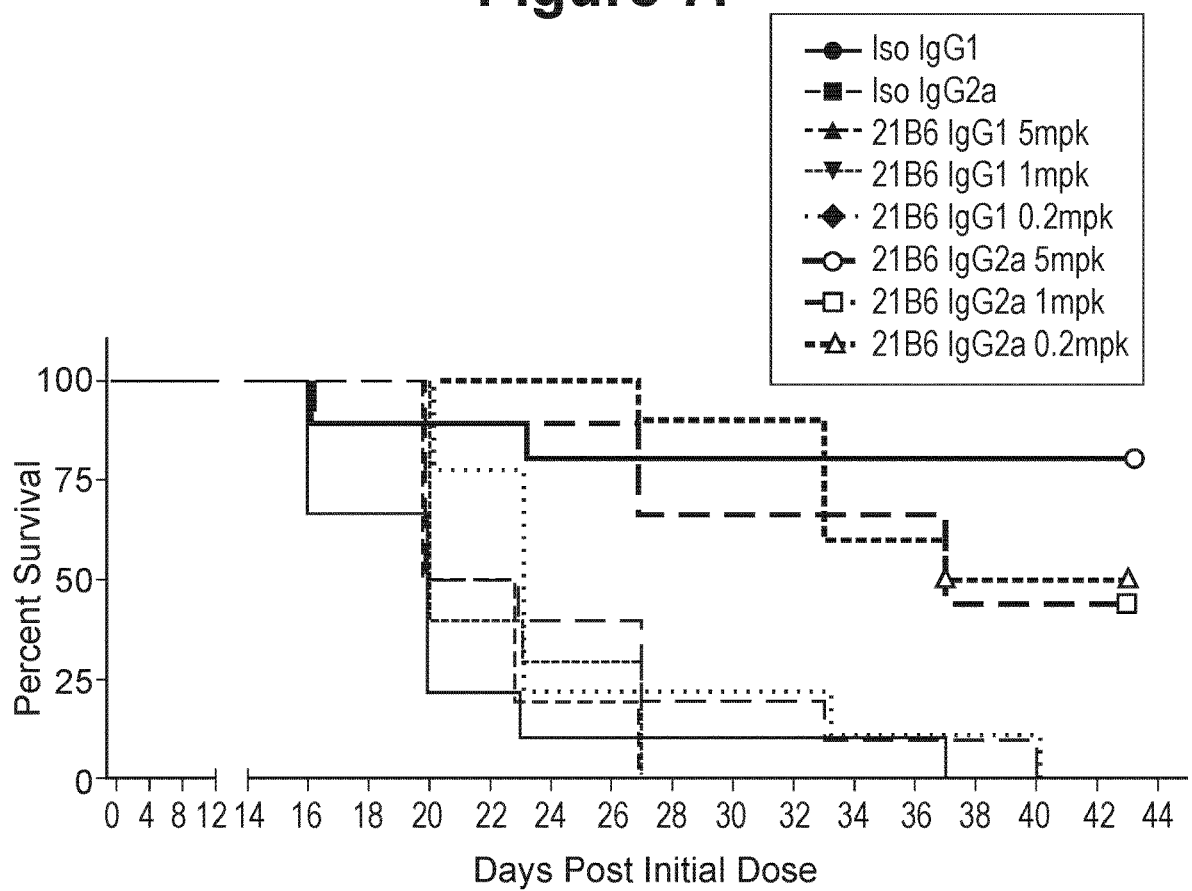

FIG. 7I shows that the IgG1 treatment did not improve survival of tumor bearing mice compared to isotype control treated mice, whereas IgG2a treatment resulted in 40%, 44.4% and 80% survival 0.2 mpk, 1 mpk and 5 mpk, respectively.

FIG. 7J shows that the inhibition of tumor growth mediated by 21B6 mIgG2a correlated with an increase in the ratio of CD8+ T cell:Treg ratio at 1 mg/kg dose.

FIG. 7K shows that the inhibition of tumor growth mediated by 21B6 mIgG2a correlated with an increase in the ratio of CD4+ Teff cell:Treg ratio at all doses.

Figure 7L:
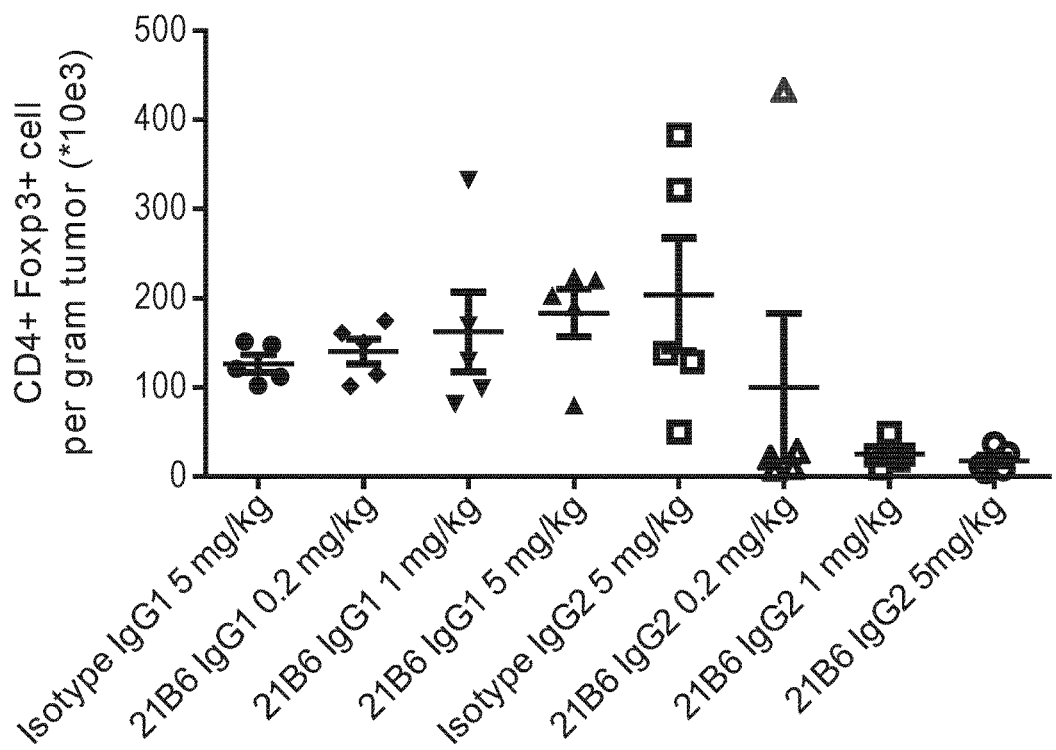
Figure 7M:
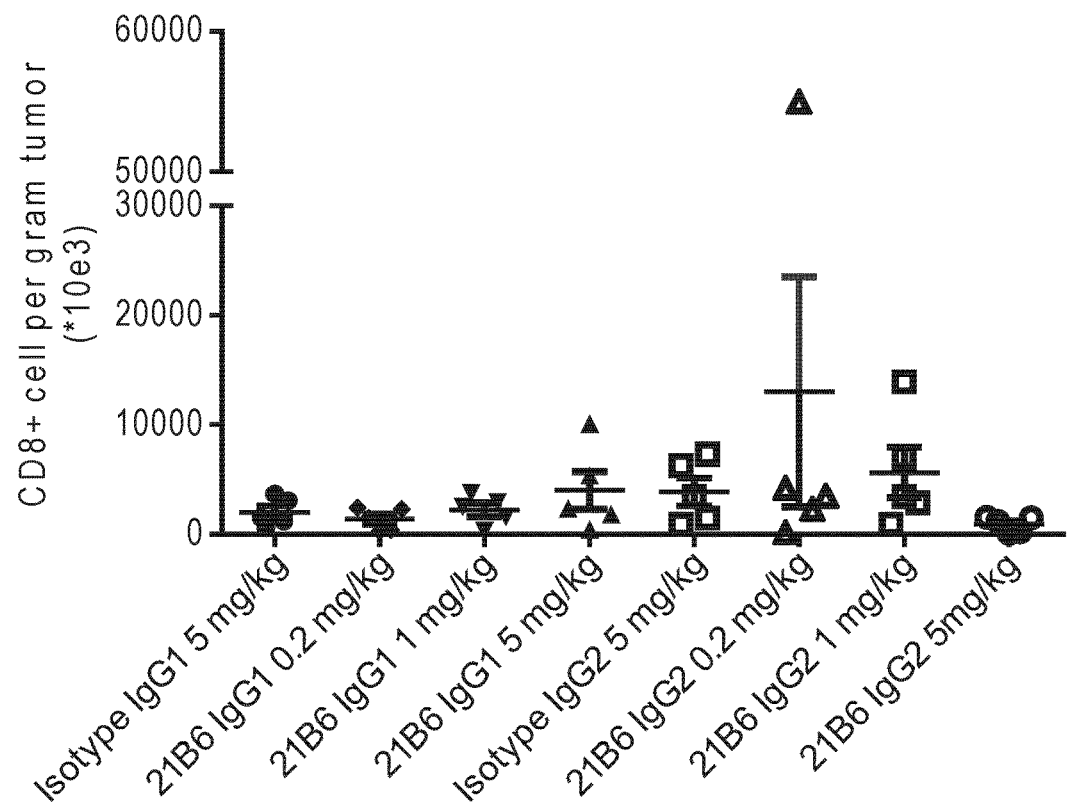
Figure 7N:
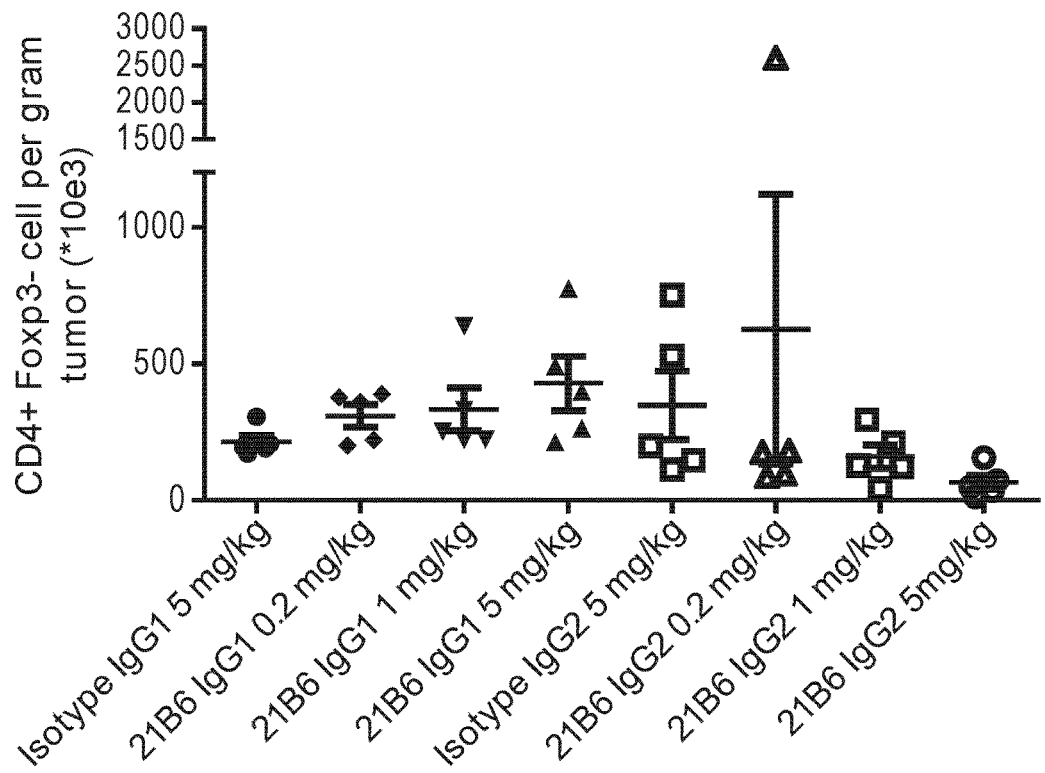

FIG. 7L, FIG. 7M, and FIG. 7N show that the 21B6 mIgG2a treated mice had a non-significant reduction in the number of tumor-infiltrating Tregs, whereas CD8+ Tcell and CD4+ Teff were unaffected.

Figure 7O:
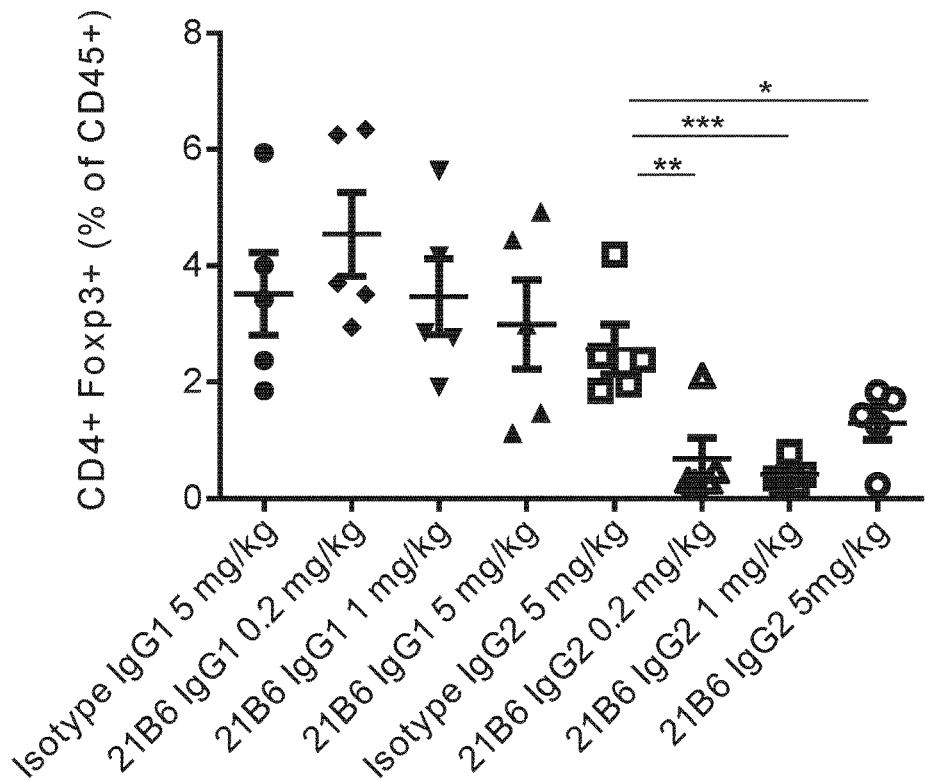

FIG. 7O shows that all doses of 21B6 mIgG2a reduced the proportion of Tregs within the CD45+ immune cells infiltrating the tumors and that the proportion of Treg in the immune infiltrate were not affected by the 21B6 mIgG1 treatment.

Figure 7P:
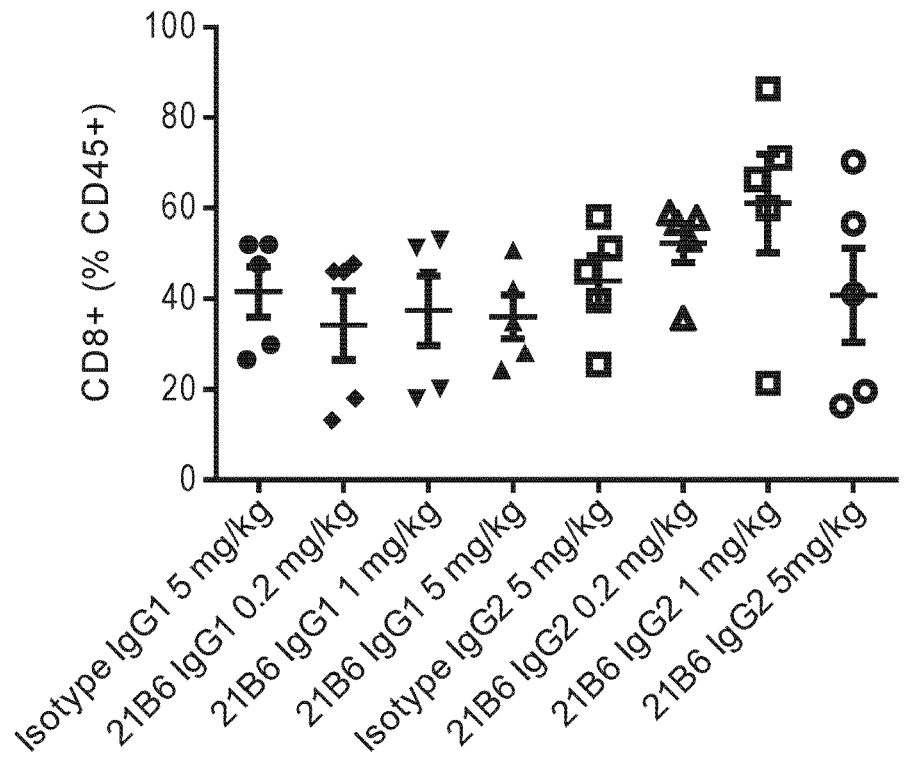
Figure 7Q:
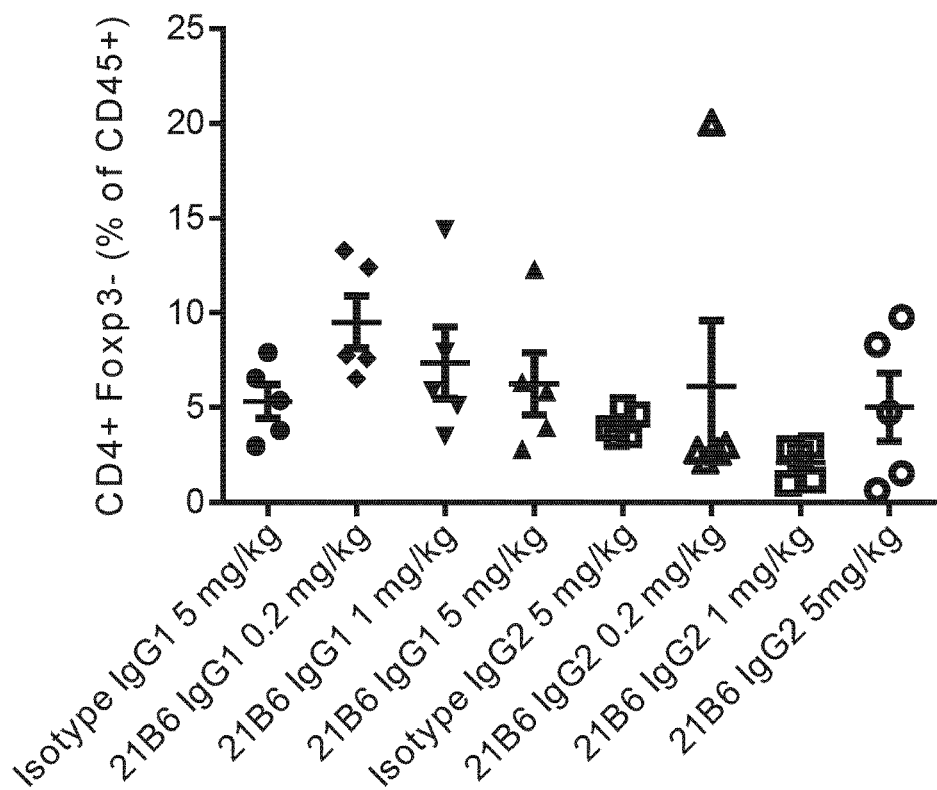

FIG. 7P and FIG. 7Q show that changes in the proportion of CD8+ T cells and CD4+ Teff cells in the tumor infiltrate were non-significant.

Figure 7R:
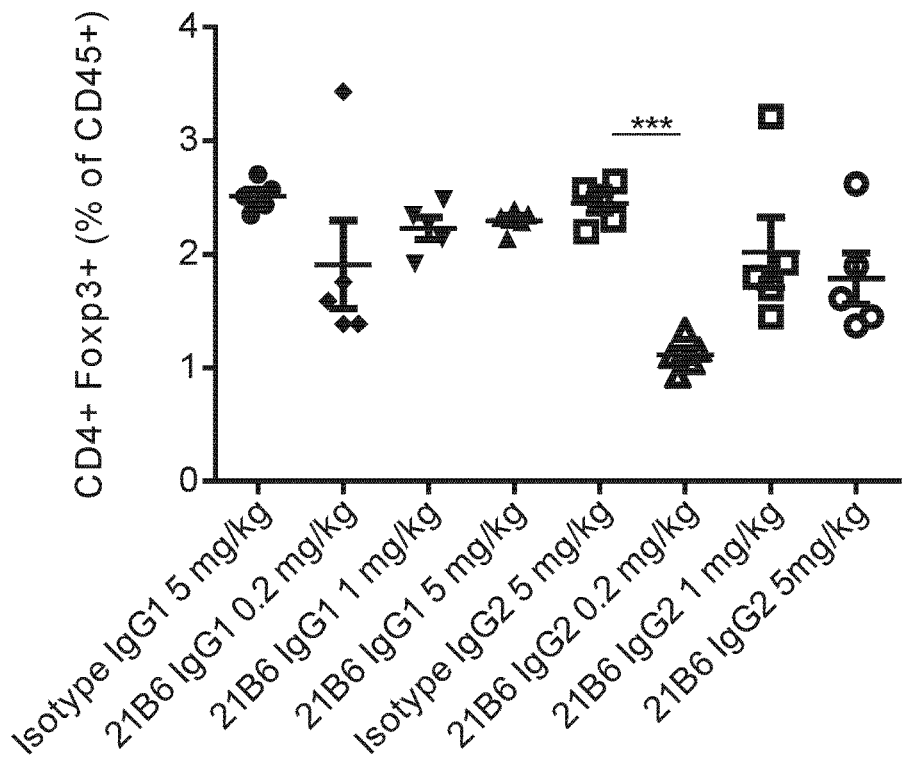
Figure 7S:
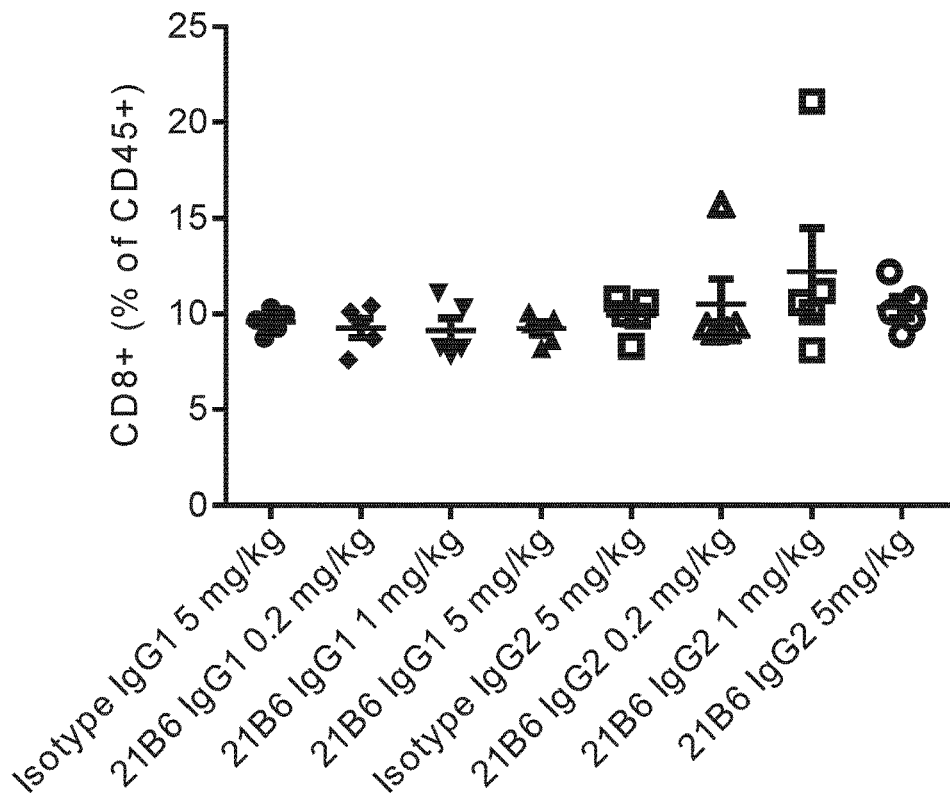
Figure 7T:
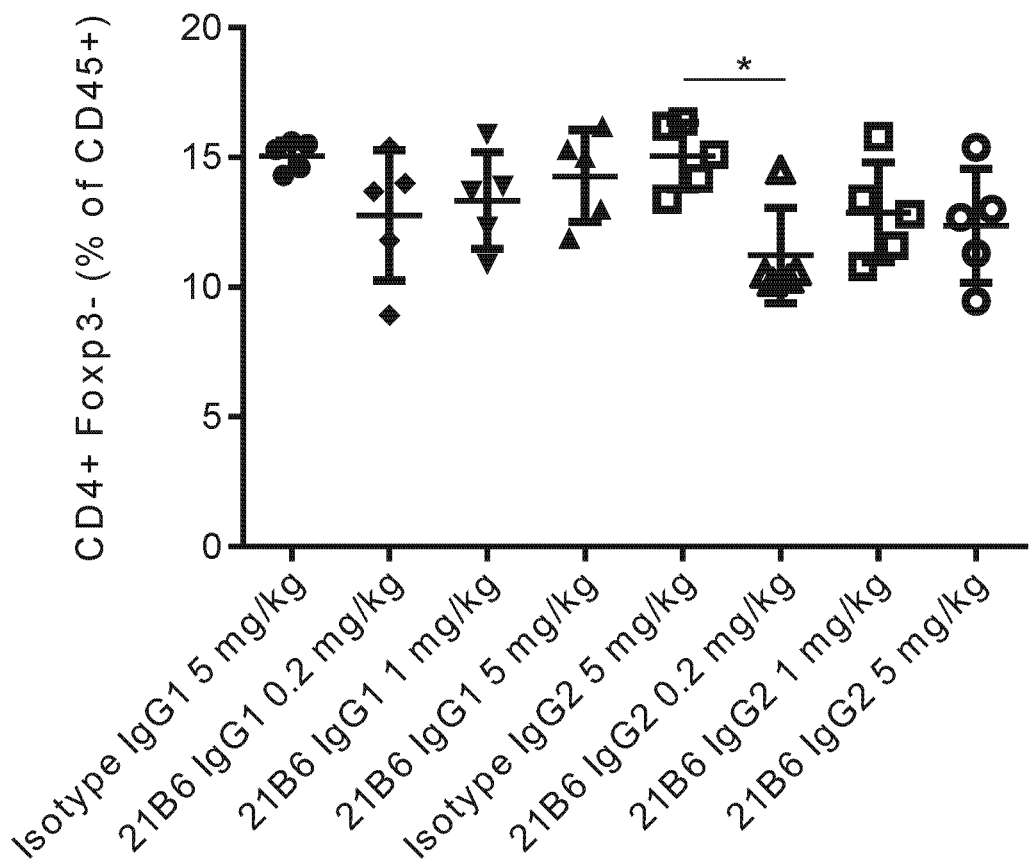

FIG. 7R, FIG. 7S, and FIG. 7T show that the 21B6 mIgG2a treated mice had the most reduction of Tregs and CD4+ Teff proportions in the spleen when treated with the 0.2 mg/kg dose (FIG. 7R and FIG. 7T), and that changes at other doses were non-significant. Splenic CD8+ T cells were unaffected at any dose (FIG. 7S).

DETAILED DESCRIPTION

Disclosed herein are antibodies that bind to GITR. Methods of making anti-GITR antibodies, compositions comprising these antibodies, and methods of using these antibodies as a medicament are provided. Anti-GITR antibodies can be used to inhibit tumor progression, and can be used in the prevention and/or treatment of cancer and/or other diseases. It is demonstrated that the anti-GITR antibodies of the present invention have at least two mechanisms of boosting the anti-tumor immunity which in turn results in tumor regression. The first mechanism is directed to the depletion of Treg infiltrating the tumor, which leads to local immune activation, particularly in enhanced T effector cell activation. The second mechanism is direct enhancement of effector functions of the T effector cells and survival of the CD8+ cells as a GITR agonist. The combined effect of Treg depletion and T effector cell activation result in enhanced T effector to Treg ratio in cold tumors and can induce tumor regression, especially in patients that have an existing adaptive anti-tumor response.

GENERAL TECHNIQUES

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The following terms, unless otherwise indicated, shall be understood to have the following meanings: the term "isolated molecule" as referring to a molecule (where the molecule is, for example, a polypeptide, a polynucleotide, or an antibody) that by virtue of its origin or source of derivation (1) is not associated with naturally associated components that accompany it in its native state, (2) is substantially free of other molecules from the same source, e.g., species, cell from which it is expressed, library, etc., (3) is expressed by a cell from a different species, or (4) does not occur in nature. Thus, a molecule that is chemically synthesized, or expressed in a cellular system different from the system from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$ and $IgA_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', $F(ab')_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to GITR, e.g., the antibodies compete for binding to the antigen.

As used herein, the term "GITR" refers to any form of GITR and variants thereof that retain at least part of the activity of GITR. Unless indicated differently, such as by specific reference to human GITR, GITR includes all mammalian species of native sequence GITR, e.g., human, canine, feline, equine, and bovine. One exemplary human GITR is found as Uniprot Accession Number Q9Y5U5 (SEQ ID NO: 108).

The term "agonist" refers to a substance which promotes (i.e., induces, causes, enhances, or increases) the biological activity or effect of another molecule. The term agonist encompasses substances which bind receptor, such as an antibody, and substances which promote receptor function without binding thereto (e.g., by activating an associated protein).

The term "antagonist antibody" refers to an antibody that binds to a target and prevents or reduces the biological effect of that target. In some embodiments, the term can denote an antibody that prevents the target to which it is bound from performing a biological function.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a GITR epitope is an antibody that binds this epitope with greater affinity, avidity, more readily, and/or with greater duration than it binds to other GITR epitopes or non-GITR epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of a tumor, remission of cancer, decreasing symptoms resulting from cancer, increasing the quality of life of those suffering from cancer, decreasing the dose of other medications required to treat cancer, delaying the progression of cancer, curing a cancer, and/or prolong survival of patients having cancer.

"Ameliorating" means a lessening or improvement of one or more symptoms as compared to not administering an anti-GITR antibody. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a disease such as, for example, cancer including, for example without limitation, B-cell related cancer, gastric cancer, small intestine cancer, sarcoma, head and neck cancer, thymic cancer, epithelial cancer, salivary cancer, liver cancer, biliary cancer, neuroendocrine tumors, stomach cancer, thyroid cancer, lung cancer, mesothelioma, ovarian cancer, breast cancer, prostate cancer, esophageal cancer, pancreatic cancer, glioma, renal cancer (e.g., renal cell carcinoma), bladder cancer, cervical cancer, uterine cancer, vulvar cancer, penile cancer, testicular cancer, anal cancer, choriocarcinoma, colorectal cancer, oral cancer, skin cancer, Merkel cell carcinoma, glioblastoma, brain tumor, bone cancer, eye cancer, and melanoma, decreasing the dose of other medications required to treat the disease, enhancing the effect of another medication, and/or delaying the progression of the cancer in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS (USA)*, 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202: 163 (1996), may be performed.

The term "$k_{on}$" or "$k_a$", as used herein, refers to the rate constant for association of an antibody to an antigen. Specifically, the rate constants ($k_{on}$ or $k_a$ and $k_{off}$ or $k_d$) and equilibrium dissociation constants are measured using whole antibody (i.e. bivalent) and monomeric GITR proteins.

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

The term "immune-effector-cell enhancer" or "IEC enhancer" refers to a substance capable of increasing or enhancing the number, quality, or function of one or more types of immune effector cells of a mammal. Examples of immune effector cells include cytolytic CD8 T cells, CD4 T cells, NK cells, and B cells.

The term "immune modulator" refers to a substance capable of altering (e.g., inhibiting, decreasing, increasing, enhancing, or stimulating) the immune response (as defined herein) or the working of any component of the innate, humoral or cellular immune system of a host mammal. Thus, the term "immune modulator" encompasses the "immune-effector-cell enhancer" as defined herein and the "immune-suppressive-cell inhibitor" as defined herein, as well as substance that affects other components of the immune system of a mammal.

The term "immune response" refers to any detectable response to a particular substance (such as an antigen or immunogen) by the immune system of a host mammal, such as innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids).

The term "immunogenic" refers to the ability of a substance to cause, elicit, stimulate, or induce an immune response, or to improve, enhance, increase or prolong a pre-existing immune response, against a particular antigen, whether alone or when linked to a carrier, in the presence or absence of an adjuvant.

The term "immune-suppressive-cell inhibitor" or "ISC inhibitor" refers to a substance capable of reducing or suppressing the number or function of immune suppressive cells of a mammal. Examples of immune suppressive cells include regulatory T cells ("Treg"), myeloid-derived suppressor cells, and tumor-associated macrophages.

The term "intradermal administration," or "administered intradermally," in the context of administering a substance to a mammal including a human, refers to the delivery of the substance into the dermis layer of the skin of the mammal. The skin of a mammal is composed of an epidermis layer, a dermis layer, and a subcutaneous layer. The epidermis is the outer layer of the skin. The dermis, which is the middle layer of the skin, contains nerve endings, sweat glands and oil (sebaceous) glands, hair follicles, and blood vessels. The subcutaneous layer is made up of fat and connective tissue that houses larger blood vessels and nerves. In contrast in intradermal administration, "subcutaneous administration" refers to the administration of a substance into the subcutaneous layer and "topical administration" refers to the administration of a substance onto the surface of the skin.

The term "neoplastic disorder" refers to a condition in which cells proliferate at an abnormally high and uncontrolled rate, the rate exceeding and uncoordinated with that of the surrounding normal tissues. It usually results in a solid lesion or lump known as "tumor." This term encompasses benign and malignant neoplastic disorders. The term "malignant neoplastic disorder", which is used interchangeably with the term "cancer" in the present disclosure, refers to a neoplastic disorder characterized by the ability of the tumor cells to spread to other locations in the body (known as "metastasis"). The term "benign neoplastic disorder" refers to a neoplastic disorder in which the tumor cells lack the ability to metastasize.

The term "preventing" or "prevent" refers to (a) keeping a disorder from occurring or (b) delaying the onset of a disorder or onset of symptoms of a disorder.

The term "tumor-associated antigen" or "TAA" refers to an antigen which is specifically expressed by tumor cells or expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules.

The term "vaccine" refers to an immunogenic composition for administration to a mammal for eliciting an immune response against a particular antigen in the mammal. A vaccine typically contains an agent (known as "antigen" or "immunogen") that resembles, or is derived from, the target of the immune response, such as a disease-causing microorganism or tumor cells. A vaccine intended for the treatment of a tumor, such as a cancer, typically contains an antigen that is derived from a TAA found on the target tumor and is able to elicit immunogenicity against the TAA on the target tumor.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

Anti-GITR Antibodies

Provided herein are anti-GITR antibodies that have the properties of boosting the anti-tumor immunity which results in tumor regression. An anti-GITR antibody of the present invention exhibits the following characteristics: (a) deplete tumor infiltrating Tregs through the function of antibody dependent cytotoxicity (ADCC) and/or antibody dependent phagocytosis (ADCP); (b) bind to GITR on the T effector cells and directly enhance the T effector cell activation; and/or (c) enhance effector functions of the T effector cells and the survival of CD8+ T cells.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the anti-GITR antibody is a monoclonal antibody. In some embodiments, the antibody is a human or humanized antibody.

The anti-GITR antibodies may be made by any method known in the art. General techniques for production of human and mouse antibodies are known in the art and/or are described herein.

Anti-GITR antibodies can be identified or characterized using methods known in the art, whereby GITR binding activity is detected. In some embodiments, an anti-GITR antibody is identified by incubating a candidate agent with GITR and monitoring binding. The binding assay may be performed with, e.g., purified GITR polypeptide(s), or with cells naturally expressing (e.g., various strains), or transfected to express, GITR polypeptide(s). In one embodiment, the binding assay is a competitive binding assay, where the ability of a candidate antibody to compete with a known anti-GITR antibody for GITR binding is evaluated. The assay may be performed in various formats, including the ELISA format. In some embodiments, an anti-GITR antibody is identified by incubating a candidate antibody with GITR and monitoring binding.

Following initial identification, the activity of a candidate anti-GITR antibody can be further confirmed and refined by bioassays, known to test the targeted biological activities. In some embodiments, an in vitro cell assay is used to further characterize a candidate anti-GITR antibody.

The anti-GITR antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-GITR antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-GITR antibody. In another example, the epitope to which the anti-GITR antibody binds can be determined in a systematic screening by using overlapping peptides derived from the GITR sequence and determining binding by the anti-GITR antibody. According to the gene fragment expression assays, the open reading frame encoding GITR is fragmented either randomly or by specific genetic constructions and the reactivity of the expressed fragments of GITR with the antibody to be tested is determined. The gene fragments may, for example, be produced by PCR and then transcribed and translated into protein in vitro, in the presence of radioactive amino acids. The binding of the antibody to the radioactively labeled GITR fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant GITR in which various residues of the GITR polypeptide have been replaced with alanine. By assessing binding of the antibody to the mutant GITR, the importance of the particular GITR residues to antibody binding can be assessed.

Yet another method which can be used to characterize an anti-GITR antibody is to use competition assays with other antibodies known to bind to the same antigen, i.e., various fragments of GITR, to determine if the anti-GITR antibody binds to the same epitope as other antibodies. Competition assays are well known to those of skill in the art, including in an ELISA format.

The binding affinity ($K_D$) of an anti-GITR antibody to GITR can be about 0.001 to about 200 nM. In some embodiments, the binding affinity is any of about 200 nM, about 150 nM, about 100 nM, about 50 nM, about 20 nM, about 19 nM, about 18 nM, about 17 nM, about 16 nM, about 15 nM, about 14 nM, about 13 nM, about 12 nM, about 11 nM, about 10 nM, about 9 nM, about 8 nM, about 7 nM, about 6 nM, about 5 nM, about 4 nM, about 3 nM, about 2 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, or about 2 pM.

Accordingly, the invention provides any of the following, or compositions (including pharmaceutical compositions) comprising an antibody having a partial light chain sequence and a partial heavy chain sequence as found in Table 1, or variants thereof. In Table 1, the underlined sequences are CDR sequences according to Kabat and in bold according to Chothia.

TABLE 1

| mAb | Light Chain | Heavy Chain |
|---|---|---|
| m3G7 | DIVLTQSPASLAVSLGQRATISC R ASESVDNFGINFMNWFQQKSGQ PPKLLIYAASNQGSGVPARFSGS GSGTDFSLDIHPMEEDDTAMYFC QQSKELPWTFGGGTKLEIK (SEQ ID NO: 1) | EVQLQQSGPERVKPGASMKISCK VSGYSFT DYTMNWVKQSHGKNL EWIG LINPYNGGIRYNQKFKGKAS LTVDKSSNTAYMELLSLTSEDSAV YYCAR IGGYYDSMDYWGQGTSV TVSS (SEQ ID NO: 2) |
| h3G7 VL1.1 | DIQMTQSPSSLSASVGDRVTITC RASESVDNFGINFLNWFQQKPG KAPKLLIYAASNQGSGVPSRFSG SGSGTDFTLTISSLQPEDFATYYC QQSKELPWTFGGGTKVEIK (SEQ ID NO: 3) | EVQLVESGGGLVQPGGSLRLSCA VSGYSFT DYTMNWVRQAPGKGL EWVA LINPYNGGIRYNQKFKGRF TISVDNAKNSLYLQMNSLRAEDTA VYYCAR IGGYYDSMDYWGQGTL VTVSS (SEQ ID NO: 4) |
| h3G7 H1 | DIQMTQSPSSLSASVGDRVTITC RASESVDNFGINFLNWYQQKPG KAPKLLIYAASNQGSGVPSRFSG SGSGTDFTLTISSLQPEDFATYYC QQSKELPWTFGGGTKVEIK (SEQ ID NO: 5) | EVQLVESGGGLVQPGGSLRLSCA ASGFTFS DYTMNWVRQAPGKGL EWVA LINPYNGGIRYNQKFKGRF TISRDNAKNSLYLQMNSLRAEDT AVYYCAR IGGYYDSMDYWGQGT LVTVSS (SEQ ID NO: 6) |
| h3G7 H2 | EIVLTQSPGTLSLSPGERATLSC R ASESVDNFGINFMNWYQQKPGQ APRLLIYAASNQGSGIPDRFSGS GSGTDFTLTISRLEPEDFAVYYC QQSKELPWTFGQGTKVEIK (SEQ ID NO: 7) | QVQLVQSGAEVKKPGASVKVSC KASGYTFT DYTMNWVRQAPGQG LEWMG LINPYNGGIRYNQKFKGR VTMTRDTSTSTVYMELSSLRSED TAVYYCAR IGGYYDSMDYWGQG TLVTVSS (SEQ ID NO: 8) |
| h3G7 AM | DIQMTQSPSSLSASVGDRVTITC RASESVDPRGINFLNWYQQKPG KAPKLLIYAASNQAKGVPSRFSG SGSGTDFTLTISSLQPEDFATYYC QQALELPWTFGGGTKVEIK (SEQ ID NO: 9) | QVQLVQSGAEVKKPGASVKVSC KASGYTFT GATMNWVRQAPGQG LEWMG LINPYNGGIRYNQKFKGR VTMTRDTSTSTVYMELSSLRSED TAVYYCAR IGGYYDSMDYWGQG TLVTVSS (SEQ ID NO: 10) |
| h3G7 R5 | DIQMTQSPSSLSASVGDRVTITC RASESVEPRGINFLNWYQQKPG KAPKLLIYAASQASKGVPSRFSG SGSGTDFTLTISSLQPEDFATYYC QQALELPWTFGGGTKVEIK (SEQ ID NO: 11) | QVQLVQSGAEVKKPGASVKVSC KASGYTFT GATMNWVRQAPGQG LEWMG LINPYTGGIRYNQKFKGR VTMTRDTSTSTVYMELSSLRSED TAVYYCAR IGGYYDSMDYWGQG TLVTVSS (SEQ ID NO: 12) |
| h3G7 LF | DIQMTQSPSSLSASVGDRVTITC RASESVEPRGINFLNWYQQKPG KAPKLLIYAASQASKGVPSRFSG SGSGTDFTLTISSLQPEDFATYYC QQALELPWTFGGGTKVEIK (SEQ ID NO: 13) | QVQLVQSGAEVKKPGASVKVSC KASGYTFT GATMINWVRQAPGQG LEWMG LINPYTGGIRYNQKFKGR VTMTRDTSTSTVYMELSSLRSED TAVYYCAR IGGYYDTMDYWGQG TLVTVSS (SEQ ID NO: 14) |
| h3G7 N9 | DIQMTQSPSSLSASVGDRVTITC RASESVQPRGINFLNWYQQKPG KAPKLLIYAASNPSKGVPSRFSG SGSGTDFTLTISSLQPEDFATYYC QQALELPWTFGGGTKVEIK (SEQ ID NO: 111) | QVQLVQSGAEVKKPGASVKVSC KASGYTFT GYTVSWVRQAPGQG LEWMG LINPYTGGIRYNQKFKGR VTMTRDTSTSTVYMELSSLRSED TAVYYCAR IGGYYDSMDYWGQG TLVTVSS (SEQ ID NO: 112) |

TABLE 1-continued

Variable Regions Sequences of Anti-GITR Antibodies

| mAb | Light Chain | Heavy Chain |
|---|---|---|
| m10H2 | DILLTQSPAILSVSPGERVSFSC R<br>ASQSIGTSIHWYQQRTNGSPRLL<br>IK YASESVSGIPSRFSGSGSGTD<br>FTLFINSVESEDIADYYC QQTYS<br>WPATFGAGTKLELK<br>(SEQ ID NO: 15) | QVQLQQSGAELMKPGASVKISCT<br>ATGYTIS RYWIEWVKQRPGHGLE<br>WIG EILPGSGVTNYNEKFKGKATF<br>TADTSSNTAYMQLSSLTSEDSAV<br>YSCAR KGTYYAMDYWGQGTSVT<br>VSS<br>(SEQ ID NO: 16) |
| h10H2<br>HU | EIVLTQSPGTLSLSPGERATLSC R<br>ASQSIGTSIHWYQQKPGQAPRLL<br>IY YASESVSGIPDRFSGSGSGTD<br>FTLTISRLEPEDFAVYYC QQTYS<br>WPATFGQGTKVEIK<br>(SEQ ID NO: 17) | QVQLVQSGAEVKKPGSSVKVSC<br>KASGGTFS RYWIEWVRQAPGQG<br>LEWMG EILPGSGVTNYNEKFKGR<br>VTITADESTSTAYMELSSLRSEDT<br>AVYYCAR KGTYYAMDYWGQGTS<br>VTVSS<br>(SEQ ID NO: 18) |
| h10H2<br>AM | EIVLTQSPGTLSLSPGERATLSC R<br>ASQSIGTSIHWYQQKPGQAPRLL<br>IY YASESVSGIPDRFSGSGSGTD<br>FTLTISRLEPEDFAVYYC QQTYS<br>WPATFGQGTKVEIK<br>(SEQ ID NO: 19) | QVQLVQSGAEVKKPGSSVKVSC<br>KASGGTFS RYWIEWVRQAPGQG<br>LEWMG EILPGSGVTFENEKFKGR<br>VTITADESTSTAYMELSSLRSEDT<br>AVYYCAR KGRYYAMDYWGQGTL<br>VTVSS<br>(SEQ ID NO: 20) |
| h10H2<br>N13 | EIVLTQSPGTLSLSPGERATLSC R<br>ASQSIGTSIHWYQQKPGQAPRLL<br>IY YASESVSGIPDRFSGSGSGTD<br>FTLTISRLEPEDFAVYYC QQTYS<br>WPATFGQGTKVEIK<br>(SEQ ID NO: 120) | QVQLVQSGAEVKKPGSSVKVSC<br>KASGGTFS RYWIEWVRQAPGQG<br>LEWMG EILPGSGVEWYNEKFKG<br>RVTITADESTSTAYMELSSLRSED<br>TAVYYCAR KGRGYAMDYWGQG<br>TSVTVSS<br>(SEQ ID NO: 121) |
| h10H2<br>N14 | EIVLTQSPGTLSLSPGERATLSC R<br>ASQSIGTSIHWYQQKPGQAPRLL<br>IY YASESVSGIPDRFSGSGSGTD<br>FTLTISRLEPEDFAVYYC QQTYS<br>WPATFGQGTKVEIK<br>(SEQ ID NO: 122) | QVQLVQSGAEVKKPGSSVKVSC<br>KASGGTFS RYWIEWVRQAPGQG<br>LEWMG EILPGSGVTFENEKFKGR<br>VTITADESTSTAYMELSSLRSEDT<br>AVYYCAR KGRYYAMDYWGQGT<br>SVTVSS<br>(SEQ ID NO: 123) |
| r18H12 | DIVMTQSPSSLAVSAGETVTINC K<br>SSQSLLYSGNQKSYLAWYQQKP<br>GQSPKLLIYWASPRQSGVPDRFI<br>GSGSGTDFTLTISSVQAEDMATY<br>YC QQYDAPPTFGGGTKLEIK<br>(SEQ ID NO: 69) | EVQLVESDGVLVQPGKSLTLSCA<br>ASGFTFS DYYMAWVRQAPTKGL<br>EWVA TISYDDITTFYRDSVKGRFT<br>ISRDTAKSTLYLQMDSLRSEDTAT<br>YYCTR GLQWPYVMDAWGQGAL<br>VTVSS<br>(SEQ ID NO: 70) |
| r21B6 | EIVLTQSPTTMAASPGEKVTITC R<br>ASSSLNYMHWFQQKSGTSPKP<br>WIYDTSELASGVPDRFSGSGSG<br>TSYSLTISSMEAEDAATYYCLQK<br>NGYPLTFGSGTKLEIK<br>(SEQ ID NO: 71) | EAQLVESGGGLVQPGRSLKLSCE<br>ASGFTFT KYGMAWVRQAPTKGL<br>EWVA SIINSGGNTYYRDSVKGRF<br>TISRDNAKSTLYLQMDSLRSEDTA<br>TYYCAT DYYDGSYHSDVVDAWG<br>QGVLVTVSS<br>(SEQ ID NO: 72) |

The invention also provides CDR portions of antibodies to GITR. Determination of CDR regions is well within the skill of the art. It is understood that in some embodiments, CDRs can be a combination of the Kabat and Chothia CDR (also termed "combined CDRs" or "extended CDRs"). In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. In general, "conformational CDRs" include the residue positions in the Kabat CDRs and Vernier zones which are constrained in order to maintain proper loop structure for the antibody to bind a specific antigen. Determination of conformational CDRs is well within the skill of the art. In some embodiments, the CDRs are the Kabat CDRs. In other embodiments, the CDRs are the Chothia CDRs. In other embodiments, the CDRs are the extended, AbM, conformational, or contact CDRs. In other words, in embodiments with more than one CDR, the CDRs may be any of Kabat, Chothia, extended, AbM, conformational, contact CDRs or combinations thereof.

In some embodiments, the antibody comprises three CDRs of any one of the heavy chain variable regions shown in Table 1. In some embodiments, the antibody comprises three CDRs of any one of the light chain variable regions shown in Table 1. In some embodiments, the antibody comprises three CDRs of any one of the heavy chain variable regions shown in Table 1, and three CDRs of any one of the light chain variable regions shown in Table 1.

In some embodiments, provided is an isolated antibody that specifically binds to GITR and comprises: a heavy chain variable region (VH) comprising a VH CDR1, VH CDR2, and VH CDR3 of the VH having an amino acid sequence selected from the group consisting of SEQ ID NO: 2, 4, 6, 8, 10, 12, 14, or 112; and/or a light chain variable region (VL) comprising a VL CDR1, VL CDR2, and VL CDR3 of the VL having an amino acid sequence selected from the group consisting of SEQ ID NO: 1, 3, 5, 7, 9, 11, 13, or 111.

In some embodiments, the antibody comprises a VH comprising the amino acid sequence shown in SEQ ID NO: 2, 4, 6, 8, 10, 12, 14, or 112, or a variant thereof with one or several conservative amino acid substitutions in residues that are not within a CDR. In some embodiments, the antibody comprises a VL comprising the amino acid sequence shown in SEQ ID NO: 1, 3, 5, 7, 9, 11, 13, or 111, or a variant thereof with one or several amino acid substitutions in amino acids that are not within a CDR.

In some embodiments, provided is an isolated antibody that specifically binds to GITR and comprises: a VH comprising a VH CDR1, VH CDR2, and VH CDR3 of the VH having an amino acid sequence selected from the group consisting of SEQ ID NO: 16, 18, 20, 121, and 123; and/or a VL comprising a VL CDR1, VL CDR2, and VL CDR3 of the VL having an amino acid sequence selected from the group consisting of SEQ ID NO: 15, 17, 19, 120, and 122.

In some embodiments, provided is an isolated antibody that specifically binds to GITR and comprises: a VH comprising a VH CDR1, VH CDR2, and VH CDR3 of the VH having an amino acid sequence selected from the group consisting of SEQ ID NO: 70 and 72; and/or a VL comprising a VL CDR1, VL CDR2, and VL CDR3 of the VL having an amino acid sequence selected from the group consisting of SEQ ID NO: 69 and 71.

In some embodiments, the antibody comprises the full-length heavy chain, with or without the C-terminal lysine, and/or the full-length light chain of anti-GITR antibody. For example, the anti-GITR antibody comprises a heavy chain comprising the amino acid sequence shown in SEQ ID NO: 110, and a light chain comprising the amino acid sequence shown in SEQ ID NO: 109.

Table 2 provides examples of CDR sequences of anti-GITR antibodies provided herein.

TABLE 2

Anti-GITR antibodies (mAbs) and their antigen-binding CDR sequences according to Kabat and Chothia

| mAb | | CDR1 | CDR2 | CDR3 |
|---|---|---|---|---|
| m3G7 | L | RASESVDNFGINFMN (SEQ ID NO: 21) | AASNQGS (SEQ ID NO: 22) | QQSKELPWT (SEQ ID NO: 23) |
| | H | GYSFTDY (SEQ ID NO: 24) (Chothia) DYTMN (SEQ ID NO: 25) (Kabat) GYSFTDYTMN (SEQ ID NO: 26) (Extended) | NPYNGG (SEQ ID NO: 27) (Chothia) LINPYNGGIRYNQKFKG (SEQ ID NO: 28) (Kabat) | IGGYYDSMDY (SEQ ID NO: 29) |
| h3G7V L1.1 | L | RASESVDNFGINFLN (SEQ ID NO: 30) | AASNQGS (SEQ ID NO: 22) | QQSKELPWT (SEQ ID NO: 23) |
| | H | GYSFTDY (SEQ ID NO: 24) (Chothia) DYTMN (SEQ ID NO: 25) (Kabat) GYSFTDYTMN (SEQ ID NO: 26) (Extended) | NPYNGG (SEQ ID NO: 27) (Chothia) LINPYNGGIRYNQKFKG (SEQ ID NO: 28) (Kabat) | IGGYYDSMDY (SEQ ID NO: 29) |
| h3G7 H1 | L | RASESVDNFGINFLN (SEQ ID NO: 30) | AASNQGS (SEQ ID NO: 22) | QQSKELPWT (SEQ ID NO: 23) |
| | H | GFTFSDY (SEQ ID NO: 32) (Chothia) DYTMN (SEQ ID NO: 25) (Kabat) GFTFSDYTMN (SEQ ID NO: 33) (Extended) | NPYNGG (SEQ ID NO: 27) (Chothia) LINPYNGGIRYNQKFKG (SEQ ID NO: 28) (Kabat) | IGGYYDSMDY (SEQ ID NO: 29) |
| h3G7 H2 | L | RASESVDNFGINFMN (SEQ ID NO: 21) | AASNQGS (SEQ ID NO: 22) | QQSKELPWT (SEQ ID NO: 23) |
| | H | GYTFTDY (SEQ ID NO: 34) (Chothia) DYTMN (SEQ ID NO: 25) (Kabat) GYTFTDYTMN (SEQ ID NO: 35) (Extended) | NPYNGG (SEQ ID NO: 27) (Chothia) LINPYNGGIRYNQKFKG (SEQ ID NO: 28) (Kabat) | IGGYYDSMDY (SEQ ID NO: 29) |

TABLE 2-continued

Anti-GITR antibodies (mAbs) and their antigen-binding CDR sequences according to Kabat and Chothia

| mAb | | CDR1 | CDR2 | CDR3 |
|---|---|---|---|---|
| h3G7 AM | L | RASESVDPRGINFLN (SEQ ID NO: 36) | AASNQAK (SEQ ID NO: 37) | QQALELPWT (SEQ ID NO: 38) |
| | H | GYTFTGA (SEQ ID NO: 39) (Chothia) GATMN (SEQ ID NO: 40) (Kabat) GYTFTGATMN (SEQ ID NO: 41) (Extended) | NPYNGG (SEQ ID NO: 27) (Chothia) LINPYNGGIRYNQKFKG (SEQ ID NO: 28) (Kabat) | IGGYYDSMDY (SEQ ID NO: 29) |
| h3G7 R5 | L | RASESVEPRGINFLN (SEQ ID NO: 42) | AASQASK (SEQ ID NO: 43) | QQALELPVVT (SEQ ID NO: 38) |
| | H | GYTFTGA (SEQ ID NO: 39) (Chothia) GATMN (SEQ ID NO: 40) (Kabat) GYTFTGATMN (SEQ ID NO: 41) (Extended) | NPYTGG (SEQ ID NO: 44) (Chothia) LINPYTGGIRYNQKFKG (SEQ ID NO: 45) (Kabat) | IGGYYDSMDY (SEQ ID NO: 29) |
| h3G7 LF | L | RASESVEPRGINFLN (SEQ ID NO: 42) | AASQASK (SEQ ID NO: 43) | QQALELPWT (SEQ ID NO: 38) |
| | H | GYTFTGA (SEQ ID NO: 39) (Chothia) GATMN (SEQ ID NO: 40) (Kabat) GYTFTGATMN (SEQ ID NO: 41) | NPYTGG (SEQ ID NO: 44) (Chothia) LINPYTGGIRYNQKFKG (SEQ ID NO: 45) (Kabat) | IGGYYDTMDY (SEQ ID NO: 46) |
| h3G7 N9 | L | RASESVQPRGINFLN (SEQ ID NO: 113) | AASNPSK (SEQ ID NO: 114) | QQALELPWT (SEQ ID NO: 38) |
| | H | GYTFTGY (SEQ ID NO: 116) (Chothia) GYTVS (SEQ ID NO: 117) GYTFTGYTVS (SEQ ID NO: 115) | NPYTGG (SEQ ID NO: 44) (Chothia) LINPYTGGIRYNQKFKG (SEQ ID NO: 45) (Kabat) | IGGYYDSMDY (SEQ ID NO: 29) |
| m10H2 | L | RASQSIGTSIH (SEQ ID NO: 47) | YASESVS (SEQ ID NO: 48) | QQTYSWPAT (SEQ ID NO: 49) |
| | H | GYTISRY (SEQ ID NO: 51) (Chothia) RYWIE (SEQ ID NO: 52) (Kabat) GYTISRYWIE (SEQ ID NO: 50) (Extended) | LPGSGV (SEQ ID NO: 54) (Chothia) EILPGSGVTNYNEKFKG (SEQ ID NO: 53) (Kabat) | KGTYYAMDY (SEQ ID NO: 55) |
| h10H2 HU | L | RASQSIGTSIH (SEQ ID NO: 47) | YASESVS (SEQ ID NO: 48) | QQTYSWPAT (SEQ ID NO: 49) |
| | H | GGTFSRY (SEQ ID NO: 57) (Chothia) RYWIE (SEQ ID NO: 52) (Kabat) GGTFSRYWIE (SEQ ID NO: 56) (Extended) | LPGSGV (SEQ ID NO: 54) (Chothia) EILPGSGVTNYNEKFKG (SEQ ID NO: 53) (Kabat) | KGTYYAMDY (SEQ ID NO: 55) |

TABLE 2-continued

Anti-GITR antibodies (mAbs) and their antigen-
binding CDR sequences according to Kabat and Chothia

| mAb | | CDR1 | CDR2 | CDR3 |
|---|---|---|---|---|
| h10H2 AM | L | RASQSIGTSIH (SEQ ID NO: 47) | YASESVS (SEQ ID NO: 48) | QQTYSWPAT (SEQ ID NO: 49) |
| | H | GGTFSRY (SEQ ID NO: 57) (Chothia) RYWIE (SEQ ID NO: 52) (Kabat) GGTFSRYWIE (SEQ ID NO: 56) (Extended) | LPGSGV (SEQ ID NO: 59) (Chothia) EILPGSGVTFENEKFKG (SEQ ID NO: 58) (Kabat) | KGRYYAMDY (SEQ ID NO: 60) |
| h10H2 N13 | L | RASQSIGTSIH (SEQ ID NO: 47) | YASESVS (SEQ ID NO: 48) | QQTYSWPAT (SEQ ID NO: 49) |
| | H | GGTFSRY (SEQ ID NO: 57) (Chothia) RYWIE (SEQ ID NO: 52) (Kabat) GGTFSRYWIE (SEQ ID NO: 56) (Extended) | LPGSGV (SEQ ID NO: 54) (Chothia) EILPGSGVTNYNEKFKG (SEQ ID NO: 53) (Kabat) | KGRGYAMDY (SEQ ID NO: 124) |
| h10H2 N14 | L | RASQSIGTSIH (SEQ ID NO: 47) | YASESVS (SEQ ID NO: 48) | QQTYSWPAT (SEQ ID NO: 49) |
| | H | GGTFSRY (SEQ ID NO: 57) (Chothia) RYWIE (SEQ ID NO: 52) (Kabat) GGTFSRYWIE (SEQ ID NO: 56) (Extended) | LPGSGV (SEQ ID NO: 59) (Chothia) EILPGSGVTFENEKFKG (SEQ ID NO: 58) (Kabat) | KGRYYAMDY (SEQ ID NO: 60) |
| r18H12 | L | KSSQSLLYSGNQKSYLA (SEQ ID NO: 73) | WASPRQS (SEQ ID NO: 74) | QQYYDAPPT (SEQ ID NO: 75) |
| | H | GFTFSDY (SEQ ID NO: 32) (Chothia) DYYMA (SEQ ID NO: 76) (Kabat) GFTFSDYYMA (SEQ ID NO: 77) (Extended) | SYDDIT (SEQ ID NO: 78) (Chothia) TISYDDITTFYRDSVKG (SEQ ID NO: 79) (Kabat) | GLQWPYVMDA (SEQ ID NO: 80) |
| r21B6 | L | RASSSLNYMH (SEQ ID NO: 81) | DTSELAS (SEQ ID NO: 82) | LQKNGYPLT (SEQ ID NO: 83) |
| | H | GFTFTKY (SEQ ID NO: 86) (Chothia) KYGMA (SEQ ID NO: 85) (Kabat) GFTFTKYGMA (SEQ ID NO: 84) (Extended) | SYDDIT (SEQ ID NO: 78) (Chothia) TISYDDITTFYRDSVKG (SEQ ID NO: 79) (Kabat) | DYYDGSYHSDVVDA (SEQ ID NO: 87) |

In some embodiments, the antibody comprises three light chain CDRs and three heavy chain CDRs from Table 2.

An alignment of light chain CDRs from a selective number of anti-GITR antibodies is provided in Table 3. Variable residues are shown in bold. Consensus light chain CDR sequences are provided in the last row of Table 3.

TABLE 3

Alignment of anti-GITR light chain CDRs

| mAb | VL CDR1 | SEQ ID NO: | VL CDR2 | SEQ ID NO: | VL CDR3 | SEQ ID NO: |
|---|---|---|---|---|---|---|
| m3G7 | RASESVDNFGINFMN | 21 | AASNQGS | 22 | QQSKELPWT | 23 |
| h3G7 V L1.1; h3G7 H1 | RASESVDNFGINFLN | 30 | AASNQGS | 22 | QQSKELPWT | 23 |
| h3G7 H2 | RASESVDNFGINFMN | 21 | AASNQGS | 22 | QQSKELPWT | 23 |
| h3G7 AM | RASESVDPRGINFLN | 36 | AASNQAK | 37 | QQALELPWT | 38 |
| h3G7 R5; h3G7 LF | RASESVEPRGINFLN | 42 | AASQQASK | 43 | QQALELPWT | 38 |
| | RASESV$X_1X_2X_3$GINF$X_4$N, wherein $X_1$ is D, Q, or E, $X_2$ is N or P, $X_3$ is F or R, $X_4$ is M or L | 31 | AAS$X_1X_2X_3X_4$, wherein $X_1$ is N or Q, $X_2$ is Q, P, or A, $X_3$ is G, A, or S, $X_4$ is S or K | 61 | QQ$X_1X_2$ELPWT, wherein $X_1$ is S or A, and $X_2$ is K or L | 62 |

An alignment of heavy chain CDRs from a selective number of anti-GITR antibodies is provided in Table 4. Variable residues are shown in bold. Consensus heavy chain CDR sequences are provided in the last row of Table 4.

TABLE 4

Alignment of anti-GITR heavy chain CDRs

| mAb | VL CDR1 | SEQ ID NO: | VL CDR2 | SEQ ID NO: | VL CDR3 | SEQ ID NO: |
|---|---|---|---|---|---|---|
| m3G7; h3G7 V L1.1; | GYSFTDY (Chothia) | 24 | NPYNGG (Chothia) | 27 | IGGYYDSMDY | 29 |
| | DYTMN (Kabat) | 25 | LINPYNGGIRYNQKFKG (Kabat) | 28 | | |
| | GYSFTDYTMN (Extended) | 26 | | | | |
| h3G7 H1 | GFTFSDY (Chothia) | 32 | NPYNGG (Chothia) | 27 | IGGYYDSMDY | 29 |
| | DYTMN (Kabat) | 25 | LINPYNGGIRYNQKFKG (Kabat) | 28 | | |
| | GFTFSDYTMN (Extended) | 33 | | | | |
| h3G7 H2 | GYTFTDY (Chothia) | 34 | NPYNGG (Chothia) | 27 | IGGYYDSMDY | 29 |
| | DYTMN (Kabat) | 25 | LINPYNGGIRYNQKFKG (Kabat) | 28 | | |
| | GYTFTDYTMN (Extended) | 35 | | | | |

TABLE 4-continued

Alignment of anti-GITR heavy chain CDRs

| mAb | VL CDR1 | SEQ ID NO: | VL CDR2 | SEQ ID NO: | VL CDR3 | SEQ ID NO: |
|---|---|---|---|---|---|---|
| h3G7 AM | GYTFTGA (Chothia) | 39 | NPYNGG (Chothia) | 27 | IGGYYDSMDY | 29 |
| | GATMN (Kabat) | 40 | LINPYNGGIRYNQKFKG (Kabat) | 28 | | |
| | GYTFTGATMN (Extended) | 41 | | | | |
| H3G7 R5 | GYTFTGA (Chothia) | 39 | NPYTGG (Chothia) | 44 | IGGYYDSMDY | 29 |
| | GATMN (Kabat) | 40 | LINPYTGGIRYNQKFKG (Kabat) | 45 | | |
| | GYTFTGATMN (Extended) | 41 | | | | |
| h3G7 LF | GYTFTGA (Chothia) | 39 | NPYTGG (Chothia) | 44 | IGGYYDTMDY | 46 |
| | GATMN (Kabat) | 40 | LINPYTGGIRYNQKFKG (Kabat) | 45 | | |
| | GYTFTGATMN (Extended) | 41 | | | | |
| h3G7 N9 | GYTFTGY (Chothia) | 39 | NPYTGG (Chothia) | 44 | IGGYYDTMDY | 46 |
| | GATVS (Kabat) | 40 | LINPYTGGIRYNQKFKG (Kabat) | 45 | | |
| | GYTFTGATMN (Extended) | 41 | | | | |
| | G$X_1X_2$F$X_3X_4X_5$, wherein $X_1$ is Y or F, $X_2$ is S or T, $X_3$ is T or S, $X_4$ is D or G, $X_5$ is Y or A (Chothia); | 63 | NPY$X_1$GG, wherein is $X_1$ N or T (Chothia) LINPY$X_1$GGIRYNQKFKG, wherein $X_1$ is N or T (Kabat) | 66, 67 | IGGYYD$X_1$MDY, wherein $X_1$ is S or T | 68 |
| | $X_1X_2$T$X_3X_4$, wherein $X_1$ is D or G, $X_2$ is Y or A, $X_3$ is V or M, $X_4$ is S or N (Kabat) | 64 | | | | |
| | G$X_1X_2$F$X_3X_4X_5$T$X_6X_7$, wherein $X_1$ is Y or F, $X_2$ is S or T, $X_3$ is T or S, $X_4$ is D or G, $X_5$ is Y or A, $X_6$ is V or M, $X_7$ is S or N (Extended) | 65 | | | | |

In some embodiments, the antibody comprises three light chain CDRs from Table 3 and three heavy chain CDRs from Table 4.

In some embodiments, the antibody comprises a VH CDR1 comprising the amino acid sequence of SEQ ID NO: 24, 25, 26, 32, 33, 34, 35, 39, 40, 41, 115, 116, 117, 63, 64, or 65, a VH CDR2 comprising the amino acid sequence of SEQ ID NO: 27, 28, 44, 45, 66, or 67, and a VH CDR3 comprising the amino acid sequence shown in SEQ ID NO: 29, 46, or 68; and/or a VL CDR1 comprising the amino acid sequence shown in SEQ ID NO: 21, 30, 36, 42, 113, or 31, a VL CDR2 comprising the amino acid sequence shown in SEQ ID NO: 22, 37, 43, 114, or 61, and a VL CDR3 comprising the amino acid sequence shown in SEQ ID NO: 23, 38, or 62.

In some embodiments, the antibody comprises a VH CDR1 comprising the amino acid sequence of SEQ ID NO: 50, 51, 52, 56, or 57, a VH CDR2 comprising the amino acid sequence of SEQ ID NO: 53, 54, 58, or 59, and a VH CDR3 comprising the amino acid sequence shown in SEQ ID NO: 55, 60, or 124; and/or a VL CDR1 comprising the amino acid sequence shown in SEQ ID NO: 47, a VL CDR2 comprising the amino acid sequence shown in SEQ ID NO: 48, and a VL CDR3 comprising the amino acid sequence shown in SEQ ID NO: 49.

In some embodiments, the antibody comprises a VH CDR1 comprising the amino acid sequence of SEQ ID NO: 32, 76, 77, 84, 85, or 86, a VH CDR2 comprising the amino acid sequence of SEQ ID NO: 78 or 79, and a VH CDR3 comprising the amino acid sequence shown in SEQ ID NO:

80 or 87; and/or a VL CDR1 comprising the amino acid sequence shown in SEQ ID NO: 73 or 81, a VL CDR2 comprising the amino acid sequence shown in SEQ ID NO: 74 or 82, and a VL CDR3 comprising the amino acid sequence shown in SEQ ID NO: 75 or 83.

The invention also provides methods of generating, selecting, and making anti-GITR antibodies. The antibodies of this invention can be made by procedures known in the art. In some embodiments, antibodies may be made recombinantly and expressed using any method known in the art.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the GITR monoclonal antibodies of the subject invention. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for GITR, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a GITR polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are different alkyl groups, can yield a population of antibodies (e.g., monoclonal antibodies).

If desired, the anti-GITR antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for GITR.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a GITR monoclonal antibody herein.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable regions of antibody m3G7, h3G7VL1.1, h3G7H1, h3G7H2, h3G7AM, h3G7R5, h3G7LF, h3G7N9, m10H2, h10H2HU, h10H2AM, h10H2N13, h10H2N14, r18H12, and r21B6. The sequence encoding the antibody of interest may be maintained in a vector in a host cell and the host cell can then be expanded and frozen for future use. Vectors (including expression vectors) and host cells are further described herein.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Kinexa™ biosensor analysis, and selection using any method known in the art for selection, including phage display, yeast display, and ribosome display.

To express the anti-GITR antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in Table 1 and the CDRs shown in Tables 2, 3 or 4. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to GITR. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 5 under the heading of "conservative substitutions." If such substitutions result in a change in biological activity, then more substantial changes, denominated "exemplary substitutions" in Table 5, or as further described below in reference to amino acid classes, may be introduced and the products screened.

TABLE 5

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |

TABLE 5-continued

Amino Acid Substitutions

| Original Residue | Conservative Substitutions | Exemplary Substitutions |
|---|---|---|
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for GITR, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an anti-GITR antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. In some embodiments, no more than one to five conservative amino acid substitutions are made within the framework region or constant region. In other embodiments, no more than one to three conservative amino acid substitutions are made within the framework region or constant region. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the Fc can be human $IgG_1$. In some embodiments, the constant region has the sequence shown in SEQ ID NO: 129.

In some embodiments, the Fc can be human $IgG_2$ or human $IgG_4$. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type $IgG_4$. In yet another embodiment, the Fc is human $IgG_4$ E233F234L235 to P233V234A235 with deletion G236 ($IgG_{4\Delta b}$). In some embodiments the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19). In other embodiments, the Fc can be human $IgG_2$ containing the mutation A330P331 to S330S331 ($IgG_{2\Delta a}$), in which the amino acid residues are numbered with reference to the wild type $IgG_2$ sequence. Eur. J. Immunol., 1999, 29:2613-2624.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157: 4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Publication No. WO99/058572.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an anti-GITR antibody of the invention can be cleaved. In various embodiments of the invention, the heavy and light chains of the anti-GITR antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. An example of a linking peptide is $(GGGGS)_3$ (SEQ ID NO: 130), which bridges approximately 3.5 nm between the carboxy terminus of one variable region and the amino terminus of the other variable region. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to GITR and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad Sci. USA 90:6444-6448; Poljak, R. J., et al., 1994, Structure 2:1121-1123).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO91/00360 and WO92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The invention also encompasses fusion proteins comprising one or more fragments or regions from the antibodies disclosed herein. In some embodiments, a fusion antibody may be made that comprises all or a portion of an anti-GITR antibody of the invention linked to another polypeptide. In another embodiment, only the variable domains of the anti-GITR antibody are linked to the polypeptide. In another embodiment, the VH domain of an anti-GITR antibody is linked to a first polypeptide, while the VL domain of an anti-GITR antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NO: 1, 3, 5, 7, 9, 11, 13, 15, 17, 19, 111, 120, 122, 69, or 71, and/or at least 10 amino acids of the variable heavy chain region shown in SEQ ID NO: 2, 4, 6, 8, 10, 12, 14, 16, 18, 20, 70, 72, 112, 121, or 123. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 1 and 2, 3 and 4, 5 and 6, 7 and 8, 9 and 10, 11 and 12, 13 and 14, 111 and 112, 15 and 16, 17 and 18, 19 and 20, 120 and 121, 122 and 123, 69 and 70, or 71 and 72. In another embodiment, the fusion polypeptide comprises one or more CDR(s). In still other embodiments, the fusion polypeptide comprises VH CDR3 and/or VL CDR3. For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this invention are made by preparing and expressing a polynucleotide encoding them using recombinant methods described herein, although they may also be prepared by other means known in the art, including, for example, chemical synthesis.

In other embodiments, other modified antibodies may be prepared using anti-GITR antibody encoding nucleic acid molecules. For instance, "Kappa bodies" (111 et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). For example, bispecific antibodies or antigen-binding fragments can be produced by fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins." In some embodiments, the bispecific antibody binds to two different epitopes of GITR. In some embodiments, the modified antibodies described above are prepared using one or more of the variable domains or CDR regions from an anti-GITR antibody provided herein.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

In another approach, the bispecific antibodies are composed of amino acid modification in the first hinge region in one arm, and the substituted/replaced amino acid in the first hinge region has an opposite charge to the corresponding amino acid in the second hinge region in another arm. This approach is described in International Patent Application No. PCT/US2011/036419 (WO2011/143545). In some embodiments, the formation of the bispecific antibodies is enhanced by altering or engineering an interface between a first and a second Fc region (e.g., a hinge region and a CH3 region). In this approach, the bispecific antibodies may be composed of a CH3 region, wherein the CH3 region comprises a first CH3 polypeptide and a second CH3 polypeptide which interact together to form a CH3 interface, wherein one or more amino acids within the CH3 interface destabilize homodimer (e.g., monospecific antibody) formation. See, e.g., PCT/US2011/036419 (WO2011/143545).

In another approach, the bispecific antibodies can be generated using a glutamine-containing peptide tag engineered to the antibody directed to an epitope (e.g., GITR) in one arm and another peptide tag (e.g., a Lys-containing peptide tag or a reactive endogenous Lys) engineered to a second antibody directed to a second epitope in another arm in the presence of transglutaminase. This approach is described in International Patent Application No. PCT/IB2011/054899 (WO2012/059882).

This invention also provides compositions comprising antibodies conjugated (for example, linked) to an agent that facilitate coupling to a solid support (such as biotin or avidin). For simplicity, reference will be made generally to antibodies with the understanding that these methods apply to any of the GITR binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the lung, heart, or heart valve.

An antibody or polypeptide of this invention may be linked to a labeling agent such as a fluorescent molecule, a radioactive molecule or any others labels known in the art. Labels are known in the art which generally provide (either directly or indirectly) a signal.

Polynucleotides, Vectors, and Host Cells

The invention also provides polynucleotides encoding any of the antibodies, including antibody fragments and modified antibodies described herein. In another aspect, the invention provides a method of making any of the polynucleotides described herein. Polynucleotides can be made and expressed by procedures known in the art. Accordingly, in some embodiments, the invention provides polynucleotides (or compositions, including pharmaceutical compositions), comprising polynucleotides encoding any of the following: m3G7, h3G7VL1.1, h3G7H1, h3G7H2, h3G7AM, h3G7R5, h3G7LF, h3G7N9, m10H2, h10H2HU, h10H2AM, h10H2N13, h10H2N14, r18H12, r21B6, or any fragment or part thereof having the ability to bind GITR.

In another aspect, the invention provides compositions (such as a pharmaceutical compositions) comprising any of the polynucleotides of the invention. In some embodiments, the composition comprises an expression vector comprising a polynucleotide encoding any of the antibodies described herein. In still other embodiments, the composition comprises either or both of the polynucleotides shown in SEQ ID NOs: 88 and 89; SEQ ID NOs: 90 and 91; SEQ ID NOs: 92 and 93; SEQ ID NOs: 94 and 95; SEQ ID NOs: 96 and 97; SEQ ID NOs: 98 and 99; SEQ ID NOs: 100 and 101; SEQ ID NOs: 102 and 103; SEQ ID NOs: 104 and 105; SEQ ID NOs: 106 and 107; SEQ ID NOs: 118 and 119; SEQ ID NOs: 125 and 126; SEQ ID NOs: 127 and 128.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 pg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to GITR or a GITR domain is effected by an immunoassay or FACS. A cell overexpressing the antibody or protein of interest can be identified.

An expression vector can be used to direct expression of an anti-GITR antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 pg to about 2 mg, about 5 pg to about 500 pg, and about 20 pg to about 100 pg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Compositions

The invention also provides pharmaceutical compositions comprising an effective amount of an anti-GITR antibody described herein. Examples of such compositions, as well as how to formulate, are also described herein. In some embodiments, the composition comprises one or more anti-GITR antibodies. In other embodiments, the anti-GITR antibody recognizes GITR. In other embodiments, the anti-GITR antibody is a human antibody. In other embodiments, the anti-GITR antibody is a humanized antibody. In some embodiments, the anti-GITR antibody comprises a constant region that is capable of triggering a desired immune response, such as antibody-mediated lysis, ADCC, and/or ADCP. In other embodiments, the anti-GITR antibody comprises a constant region that does not trigger an unwanted or undesirable immune response, such as antibody-mediated lysis, ADCC, and/or ADCP. In other embodiments, the anti-GITR antibody comprises one or more CDR(s) of the antibody (such as one, two, three, four, five, or, in some embodiments, all six CDRs).

It is understood that the compositions can comprise more than one anti-GITR antibody (e.g., a mixture of GITR antibodies that recognize different epitopes of GITR). Other exemplary compositions comprise more than one anti-GITR antibody that recognize the same epitope(s), or different species of anti-GITR antibodies that bind to different epitopes of GITR. In some embodiments, the compositions comprise a mixture of anti-GITR antibodies that recognize different variants of GITR.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The anti-GITR antibody and compositions thereof can also be used in conjunction with, or administered separately, simultaneously, or sequentially with other agents that serve to enhance and/or complement the effectiveness of the agents.

The invention also provides compositions, including pharmaceutical compositions, comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies described herein.

Methods for Preventing or Treating Conditions Mediated by GITR

The antibodies and the antibody conjugates of the present invention are useful in various applications including, but are not limited to, therapeutic treatment methods and diagnostic treatment methods.

In one aspect, the invention provides a method for treating a cancer. In some embodiments, the method of treating a cancer in a subject comprises administering to the subject in need thereof an effective amount of a composition (e.g., pharmaceutical composition) comprising any of the GITR antibodies as described herein. As used herein, cancers include, but are not limited to B-cell related cancer, gastric cancer, small intestine cancer, sarcoma, head and neck cancer (e.g., squamous cell head and neck cancer), thymic cancer, epithelial cancer, salivary cancer, liver cancer, biliary cancer, neuroendocrine tumors, stomach cancer, thyroid cancer, lung cancer, mesothelioma, ovarian cancer, breast cancer, prostate cancer, esophageal cancer, pancreatic cancer, glioma, renal cancer (e.g., renal cell carcinoma), bladder cancer, cervical cancer, uterine cancer, vulvar cancer, penile cancer, testicular cancer, anal cancer, choriocarcinoma, colorectal cancer, oral cancer, skin cancer, Merkel cell carcinoma, glioblastoma, brain tumor, bone cancer, eye cancer, and melanoma.

In some embodiments, the B-cell related cancer is, but not limited to, multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other B-cell related lymphoma.

In some embodiments, the cancer is relapsed or refractory.

In some embodiments, the cancer is locally advanced or metastatic melanoma, squamous cell head and neck cancer (SCHNC), ovarian cancer, renal cancer, gastric cancer, or lung cancer (e.g., NSCLC (Non-Small Cell Lung Cancer)).

In some embodiments, provided is a method of inhibiting tumor growth or progression in a subject, comprising administering to the subject in need thereof an effective amount of a composition comprising the anti-GITR antibodies as described herein. In some embodiments, provided is a method of inhibiting metastasis of cancer cells in a subject, comprising administering to the subject in need thereof an effective amount of a composition comprising any of the anti-GITR antibodies as described herein. In other embodiments, provided is a method of inducing regression of a tumor in a subject, comprising administering to the subject in need thereof an effective amount of a composition comprising any of the anti-GITR antibodies as described herein.

In another aspect, provided is a method of detecting, diagnosing, and/or monitoring a cancer. For example, the anti-GITR antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

With respect to all methods described herein, reference to anti-GITR antibodies also includes compositions comprising one or more additional agents. These compositions may further comprise suitable excipients, such as pharmaceutically acceptable excipients including buffers, which are well known in the art. The present invention can be used alone or in combination with other methods of treatment.

The anti-GITR antibody can be administered to a subject via any suitable route. It should be apparent to a person skilled in the art that the examples described herein are not intended to be limiting but to be illustrative of the techniques available. Accordingly, in some embodiments, the anti-GITR antibody is administered to a subject in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-GITR antibody can be aerosolized using a fluorocarbon formulation and a metered dose inhaler, or inhaled as a lyophilized and milled powder.

In some embodiments, an anti-GITR antibody is administered via site-specific or targeted local delivery techniques. Examples of site-specific or targeted local delivery techniques include various implantable depot sources of the anti-GITR antibody or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an anti-GITR antibody may be used for administration. In some embodiments, the anti-GITR antibody may be administered neat. In some embodiments, anti-GITR antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-GITR antibody can be administered using any suitable method, including by injection (e.g., intraperitoneally, intravenously, subcutaneously, intramuscularly, etc.). Anti-GITR antibodies can also be administered topically or via inhalation, as described herein. Generally, for administration of anti-GITR antibodies, the candidate dosage can be administered daily, every week, every other week, every three weeks, every four weeks, every five weeks, every six weeks, every seven weeks, every eight weeks, every ten weeks, every twelve weeks, or more than every twelve weeks. For repeated administrations over several days or longer, depending on the condition, the treatment is sustained until a desired suppression of symptoms occurs or until sufficient therapeutic levels are achieved, for example, to reduce symptoms associated with cancer. The progress of this therapy is easily monitored by conventional techniques and assays. The dosing regimen (including the anti-GITR antibody used) can vary over time.

In some embodiments, the candidate dosage is administered daily with the dosage ranging from about any of 1 pg/kg to 30 pg/kg to 300 pg/kg to 3 mg/kg, to 30 mg/kg, to 100 mg/kg or more, depending on the factors mentioned above. For example, daily dosage of about 0.01 mg/kg, about 0.03 mg/kg, about 0.1 mg/kg, about 0.3 mg/kg, about 1 mg/kg, about 2.5 mg/kg, about 3 mg/kg, about 5 mg/kg, about 10 mg/kg, about 15 mg/kg, and about 25 mg/kg may be used.

In some embodiments, the candidate dosage is administered every week with the dosage ranging from about any of 1 pg/kg to 30 pg/kg to 300 pg/kg to 3 mg/kg, to 30 mg/kg, to 100 mg/kg or more, depending on the factors mentioned above. For example, a weekly dosage of about 0.01 mg/kg, about 0.03 mg/kg, about 0.1 mg/kg, about 0.3 mg/kg, about 0.5 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every two weeks with the dosage ranging from about any of 1 pg/kg to 30 pg/kg to 300 pg/kg to 3 mg/kg, to 30 mg/kg, to 100 mg/kg or more, depending on the factors mentioned above. For example, a bi-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every three weeks with the dosage ranging from about any of 1 pg/kg to 30 pg/kg to 300 pg/kg to 3 mg/kg, to 30 mg/kg, to 100 mg/kg or more, depending on the factors mentioned above. For example, a tri-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In some embodiments, the candidate dosage is administered every month or every four weeks with the dosage ranging from about any of 1 pg/kg to 30 pg/kg to 300 pg/kg to 3 mg/kg, to 30 mg/kg, to 100 mg/kg or more, depending on the factors mentioned above. For example, a monthly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In other embodiments, the candidate dosage is administered daily with the dosage ranging from about 0.01 mg to about 1200 mg or more, depending on the factors mentioned above. For example, daily dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, or about 1200 mg may be used.

In other embodiments, the candidate dosage is administered every week with the dosage ranging from about 0.01 mg to about 2000 mg or more, depending on the factors mentioned above. For example, weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every two weeks with the dosage ranging from about 0.01 mg to about 2000 mg or more, depending on the factors mentioned above. For example, bi-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every three weeks with the dosage ranging from about 0.01 mg to about 2500 mg or more, depending on the factors mentioned above. For example, tri-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg may be used.

In other embodiments, the candidate dosage is administered every four weeks or month with the dosage ranging from about 0.01 mg to about 3000 mg or more, depending on the factors mentioned above. For example, monthly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, or about 3000 mg may be used.

For the purpose of the present invention, the appropriate dosage of an anti-GITR antibody will depend on the anti-GITR antibody (or compositions thereof) employed, the type and severity of symptoms to be treated, whether the agent is administered for preventive or therapeutic purposes, previous therapy, the patient's clinical history and response to the agent, the patient's clearance rate for the administered agent, and the discretion of the attending physician. Typically the clinician will administer an anti-GITR antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms. Alternatively, sustained continuous release formulations of anti-GITR antibodies may be appropriate. Various formulations and devices for achieving sustained release are known in the art.

In one embodiment, dosages for an antibody may be determined empirically in individuals who have been given one or more administration(s) of an antibody. For example, individuals are given incremental dosages of an anti-GITR antibody. To assess efficacy, an indicator of the disease can be followed.

Administration of an anti-GITR antibody as described herein in accordance with the method in the present invention can be continuous or intermittent, depending, for example, upon the recipient's physiological condition, whether the purpose of the administration is therapeutic or prophylactic, and other factors known to skilled practitioners. The administration of an anti-GITR antibody may be essentially continuous over a preselected period of time or may be in a series of spaced doses.

In some embodiments, more than one anti-GITR antibody may be present. At least one, at least two, at least three, at least four, at least five different, or more antibodies can be present. Generally, those anti-GITR antibodies may have complementary activities that do not adversely affect each other.

In some embodiments, the anti-GITR antibody may be administered in combination with the administration of one or more additional therapeutic agents. These include, but are not limited to, the administration of a biotherapeutic agent, a chemotherapeutic agent, a vaccine, a CAR-T cell-based therapy, radiotherapy, a cytokine therapy (e.g., IL-2, IL-7, IL-15, IL-12, IFNγ, IFNα, IL-8), a vaccine, an inhibitor of other immunosuppressive pathways, an inhibitors of angiogenesis, a T cell activator, an inhibitor of a metabolic pathway, an mTOR (mechanistic target of rapamycin) inhibitor (e.g., rapamycin, rapamycin derivatives, sirolimus, temsirolimus, everolimus, and deforolimus), an inhibitor of an adenosine pathway, a tyrosine kinase inhibitor including but not limited to inlyta, ALK (anaplastic lymphoma kinase) inhibitors (e.g., crizotinib, ceritinib, alectinib, and sunitinib), a BRAF inhibitor (e.g., vemurafenib and dabrafenib), an epigenetic modifier, an inhibitors or depletor of Treg cells and/or of myeloid-derived suppressor cells, a JAK (Janus Kinase) inhibitor (e.g., ruxolitinib and tofacitinb, varicitinib, filgotinib, gandotinib, lestaurtinib, momelotinib, pacritinib, and upadacitinib), a STAT (Signal Transducers and Activators of Transcription) inhibitor (e.g., STAT1, STAT3, and STAT5 inhibitors such as fludarabine), a cyclin-dependent kinase inhibitor, an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), a MEK inhibitor (e.g., trametinib, cobimetinib, binimetinib, and selumetinib), a GLS1 inhibitor, a PAP inhibitor, an oncolytic virus, an IDO (Indoleamine-pyrrole 2,3-dioxygenase) inhibitor, and cells transfected with genes encoding immune stimulating cytokines such as but not limited to GM-CSF).

In some embodiments, the biotherapeutic agent is an antibody, including but not limited to, an anti-CTLA-4 antibody, an anti-4-1BB antibody, an anti-PD-1 antibody, an anti-PD-L1 antibody, an anti-TIM3 antibody, an anti-LAG3 antibody, an anti-TIGIT antibody, an anti-OX40 antibody, an IL-8 antibody, an anti-HVEM antibody, an anti-BTLA antibody, an anti-CD40 antibody, an anti-CD40L antibody, anti-CD47 antibody, an anti-CSF1R antibody, an anti-CSF1 antibody, an anti-MARCO antibody, an anti-CXCR4 antibodies, an anti-VEGFR1 antibody, an anti-VEGFR2 antibody, an anti-TNFR1 antibody, an anti-TNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD 52 antibody, an anti-CCR4 antibody, an anti-CCR8 antibody, an anti-CD200R antibody, an anti-VISG4 antibody, an anti-CCR2 antibody, an anti-LILRb2 antibody, an anti-CXCR4 antibody, an anti-CD206 antibody, an anti-CD163 antibody, an anti-KLRG1 antibody, an anti-FLT3 antibody, an anti-B7-H4 antibody, an anti-B7-H3 antibody, or a second anti-GITR antibody.

Accordingly, in some embodiments, an anti-GITR antibody is used in conjunction with, for example, an anti-PD-L1 antagonist antibody, such as BMS-936559 (MDX-1105), MPDL3280A, and avelumab (MSB0010718C); an anti-PD-1 antagonist antibody such as for example, nivolumab (OPDIVO®), pembrolizumab (KEYTRUDA®), and pidilizumab; an anti-CTLA-4 antagonist antibody such as for example ipilimumab (YERVOY®); an anti-LAG-3 antagonist antibody such as BMS-986016 and IMP701; an anti-TIM-3 antagonist antibody; an anti-B7-H3 antagonist antibody such as for example MGA271; an-anti-VISTA antagonist antibody; an anti-TIGIT antagonist antibody; an anti-CD28 antagonist antibody; an anti-CD80 antibody; an anti-CD86 antibody; an anti-B7-H4 antagonist antibody; an anti-ICOS agonist antibody; an anti-CD28 agonist antibody; an innate immune response modulator (e.g., TLRs, KIR, NKG2A), and an IDO inhibitor. In some embodiments, an anti-GITR antibody is used in conjunction with a 4-1BB (CD137) agonist such as, for example, PF-05082566 or urelumab (BMS-663513). In some embodiments, an anti-GITR antibody is used in conjunction with an OX40 agonist such as, for example, an anti-OX-40 agonist antibody. In some embodiments, an anti-GITR antibody is used in conjunction with another GITR agonist such as, for example, TRX518. In some embodiments, an anti-GITR antibody is used in conjunction with an IDO inhibitor. In some embodiments, an anti-GITR antibody is used in conjunction with a cytokine therapy such as, for example without limitation, IL-2, IL-12, IL-7, IL-15, IL-21, IL-33, CSF-1, MCSF-1, etc.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gammal and calicheamicin phill, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), pegylated liposomal doxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

In some embodiments, an anti-GITR antibody is used in conjunction with one or more other therapeutic agents targeting an immune checkpoint modulator, such as, for example without limitation, an agent targeting PD-1, PD-L1, CTLA-4, LAG-3, B7-H3, B7-H4, B7-DC (PD-L2), B7-H5, B7-H6, B7-H8, B7-H2, B7-1, B7-2, ICOS, ICOS-L, TIGIT, CD2, CD47, CD80, CD86, CD48, CD58, CD226, CD155, CD112, LAIR1, 2B4, BTLA, CD160, TIM1, TIM-3, TIM4, VISTA (PD-H1), OX40, OX40L, GITRL, CD70, CD27, 4-1BB, 4-BBL, DR3, TL1A, CD40, CD40L, CD30, CD30L, LIGHT, HVEM, SLAM (SLAMF1, CD150), SLAMF2 (CD48), SLAMF3 (CD229), SLAMF4 (2B4, CD244), SLAMF5 (CD84), SLAMF6 (NTB-A), SLAMCF7 (CS1), SLAMF8 (BLAME), SLAMF9 (CD2F), CD28, CEACAM1 (CD66a), CEACAM3, CEACAM4, CEACAM5, CEACAM6, CEACAM7, CEACAM8, CEACAM1-3AS CEACAM3C2, CEACAM1-15, PSG1-11, CEACAM1-4C1, CEACAM1-4S, CEACAM1-4L, IDO, TDO, CCR2, CD39-CD73-adenosine pathway (A2AR), BTKs, TIKs, CXCR2, CCR4, CCR8, CCR5, VEGF pathway, CSF-1, or an innate immune response modulator.

In some embodiments, an anti-GITR antibody is used in conjunction with a biotherapeutic agent and a chemotherapeutic agent. For example, provided is a method for treating cancer in a subject in need thereof comprising administering to the subject an effective amount of the anti-GITR antibody as described wherein, an anti-PD-L1 antagonist antibody (e.g., avelumab), and a chemotherapeutic agent (e.g., gemcitabine, methotrexate, or a platinum analog). In some embodiments, provided is a method for treating cancer in a subject in need thereof comprising administering to the subject an effective amount of the anti-GITR antibody as described wherein, an anti-PD-1 antagonist antibody (e.g., nivolumab (OPDIVO®) or pembrolizumab (KEYTRUDA®), and a chemotherapeutic agent (e.g., gemcitabine, methotrexate, or a platinum analog). In some embodiments, provided is a method for treating cancer in a subject in need thereof comprising administering to the subject an effective amount of the anti-GITR antibody as described wherein, an anti-CTLA-4 antagonist antibody (e.g., ipilimumab (YERVOY®)), and a chemotherapeutic agent (e.g., gemcitabine, methotrexate, or a platinum analog).

In some embodiments, the anti-GITR antibody therapy may precede or follow the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, an anti-GITR antibody composition comprises a second agent selected from crizotinib, palbociclib, gemcitabine, cyclophosphamide, fluorouracil, FOLFOX, folinic acid, oxaliplatin, axitinib, sunitinib malate, tofacitinib, bevacizumab, rituximab, and trastuzumab.

In some embodiments, an anti-GITR antibody composition is combined with a treatment regimen further comprising a traditional therapy selected from the group consisting of: surgery, radiation therapy, chemotherapy, targeted therapy, immunotherapy, hormonal therapy, angiogenesis inhibition and palliative care.

Formulations

Therapeutic formulations of the anti-GITR antibody used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN™, PLURONICS™ or polyethylene glycol (PEG).

Liposomes containing the anti-GITR antibody are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic anti-GITR antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an anti-GITR antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

The invention also provides kits comprising any or all of the antibodies described herein. Kits of the invention include one or more containers comprising an anti-GITR antibody described herein and instructions for use in accordance with any of the methods of the invention described herein. Generally, these instructions comprise a description of administration of the anti-GITR antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In some embodiments, the antibody is a human antibody. In some embodiments, the antibody is a humanized antibody. In some embodiments, the antibody is a monoclonal antibody. The instructions relating to the use of an anti-GITR antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-GITR antibody. The container may further comprise a second pharmaceutically active agent.

Kits may optionally provide additional components such as buffers and interpretive information. Normally, the kit comprises a container and a label or package insert(s) on or associated with the container.

Biological Deposit

Representative materials of the present invention were deposited in the American Type Culture Collection, 10801 University Boulevard, Manassas, Va. 20110-2209, USA, on Nov. 10, 2016. Vector h3G7R5-VH having ATCC Accession No. PTA-123632 is a polynucleotide encoding the h3G7R5 heavy chain variable region, and vector having ATCC Accession No. PTA-123633 is a polynucleotide encoding the h3G7R5 light chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1: GITR Expression in Human Peripheral Blood T Cells

This example illustrates GITR expression by a minor fraction of T cell subsets in peripheral blood in humans.

Figure 1A:
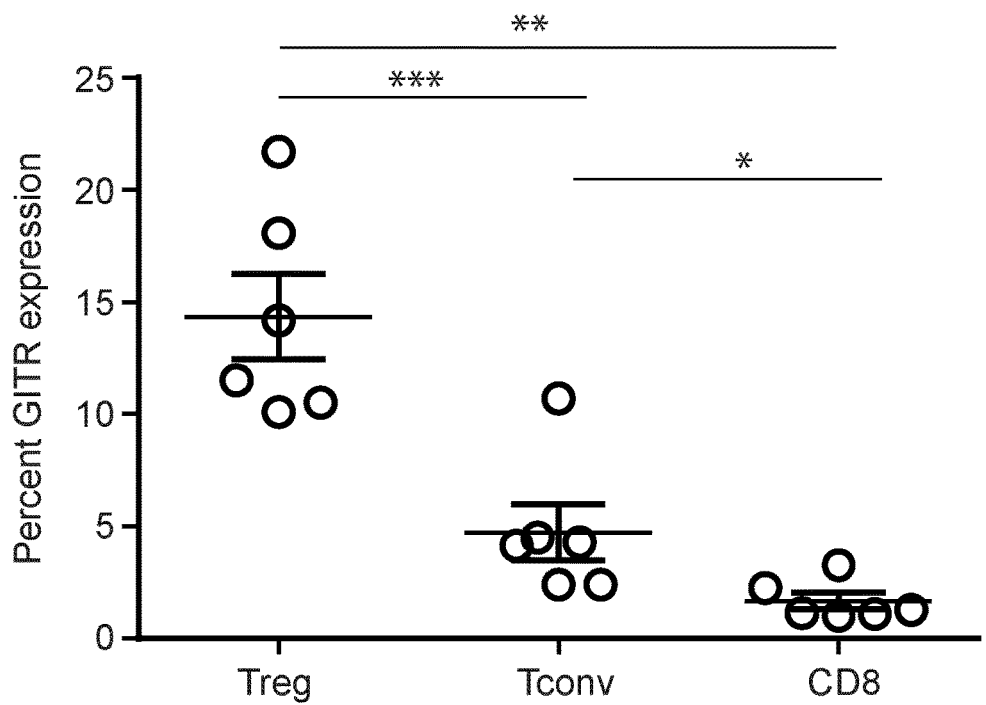
FIG. 1A depicts a graph summarizing the GITR expression in human peripheral blood T cells, including CD4+ Foxp3+T regulatory (Treg) cells, CD4+ Foxp3-T conventional (Tconv) cells, and CD8+T (CD8) cells.
Figure 1B:
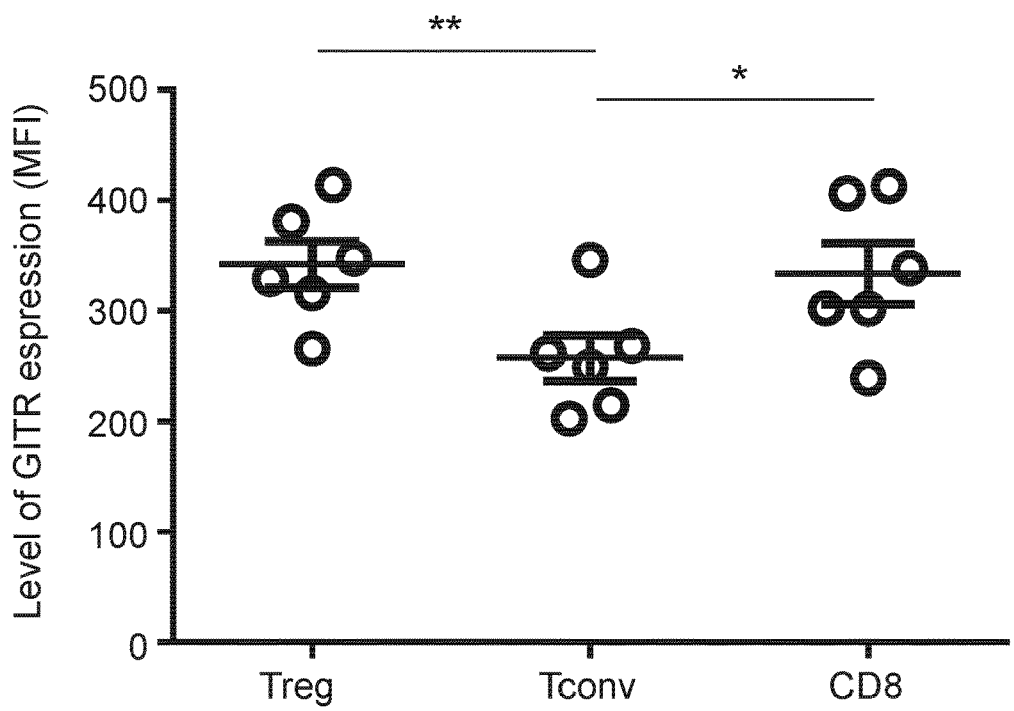
FIG. 1B depicts a graph summarizing the density (MFI) of the anti-GITR antibody (m3G7) binding to the GITR positive cells on Treg, CD8 cells, and Tconv cells.
Figure 1C:
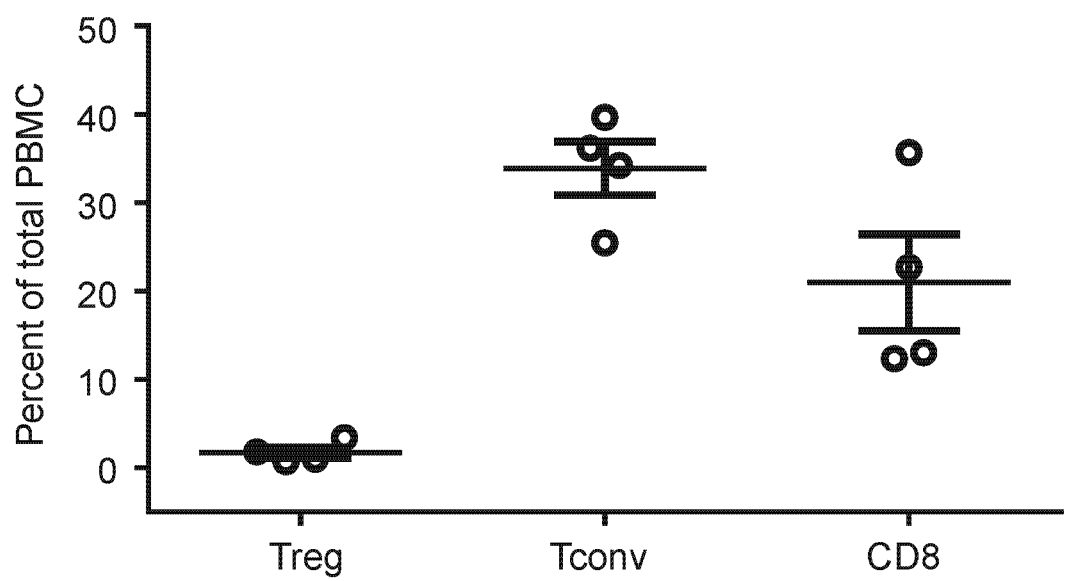
FIG. 1C depicts a graph summarizing the frequency of Treg, Tconv and CD8 cells in human peripheral blood mononuclear cells.

The expression of GITR on T cells in the peripheral blood of healthy donors was evaluated. CD4+ Foxp3+T regulatory cells (Tregs) contained a significantly higher fraction of GITR-expressing cells (14.35+/−1.9%) compared with CD4+ Foxp3− T conventional (Tconv) cells (4.75+/−1.3% GITR positive cells), or CD8+ T cells (1.68+/−0.4% GITR positive cells) (FIG. 1A). The density of the anti-GITR antibody binding to the GITR positive cells was significantly lower on CD4+ Tconv cells compared with Treg or CD8+ T cells (FIG. 1B). The Treg cells are a minor fraction comprising 1.723+/−0.61%, whereas CD4+ Tconv comprise 33.88+/−3% and CD8+ T cells 20.95+/−5.4% of peripheral blood mononuclear cells (FIG. 1C).

Example 2: GITR and OX40 Expression in Renal Cell Carcinoma Immune Cell Infiltrate in Humans This example illustrates the expression levels of GITR and OX40 in Renal Cell Carcinoma (RCC)-associated Tregs.

Figure 2A:
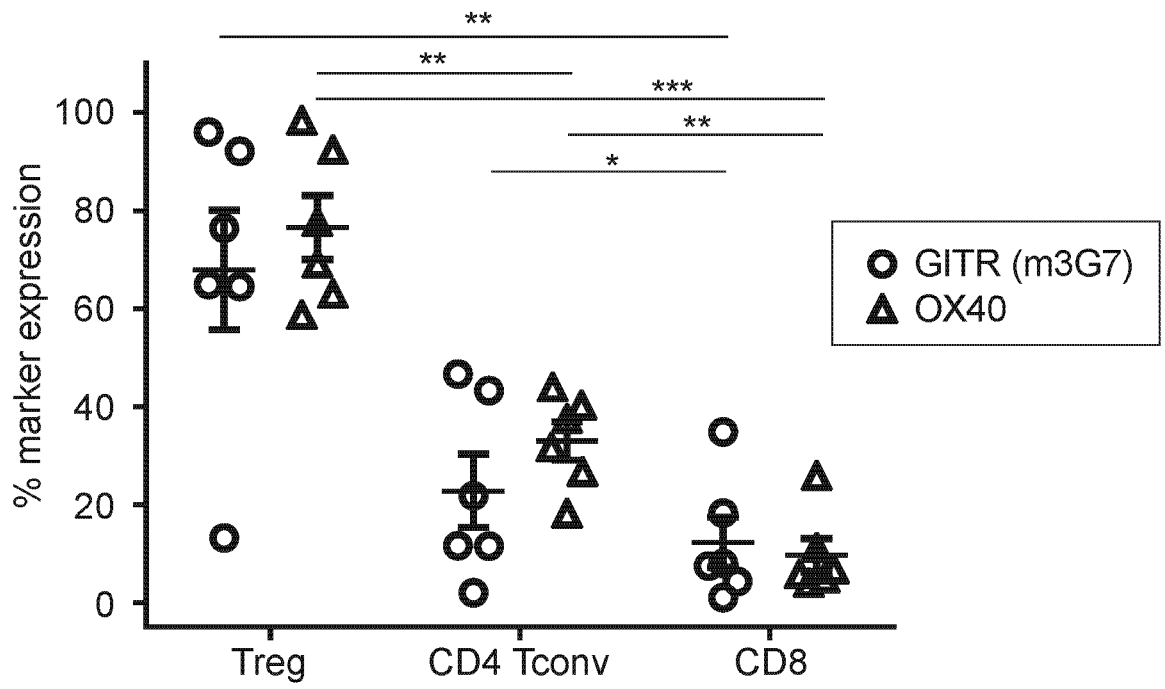
FIG. 2A depicts a graph summarizing the expression of GITR and OX40 by renal cell carcinoma-associated T cells, including CD4+ Foxp3+T regulatory (Tregs) cells, CD4+ Foxp3-T conventional (Tconv) cells, and CD8+T (CD8) cells.
Figure 2B:
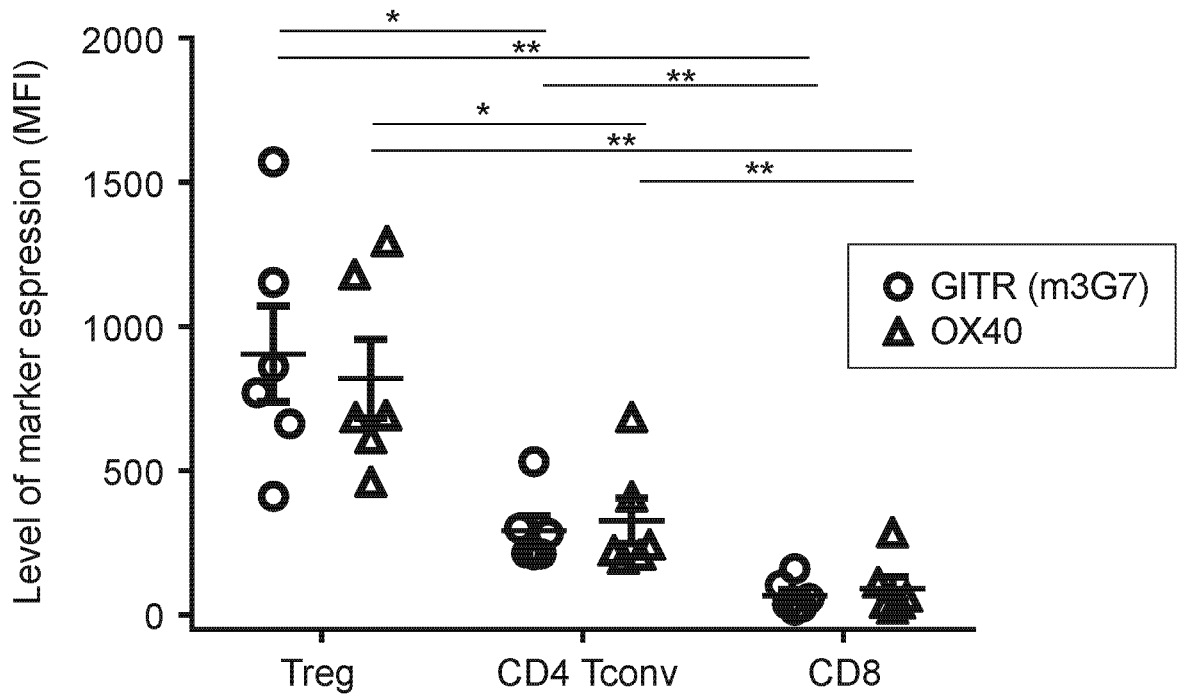
FIG. 2B depicts a graph summarizing the GITR and OX40 antibody binding density (MFI) on RCC-associated T cell subsets.

The expression of GITR and OX40 on T cells infiltrating renal cell carcinoma were evaluated. CD4+ Foxp3+ Helios+ Tregs infiltrating RCC contained more GITR and OX40-expressing cells than did CD8+ T cells, and more OX40-expressing Treg and Tconv cells than CD8+ T cells (FIG. 2A). Of Tregs, 67.8+/−12.2% expressed GITR and 76.5+/−6.5% expressed OX40. Whereas of RCC-associated CD4+ Tconv, 22.8+/−7.5% expressed GITR and 32.97+/−3.9%) expressed OX40 and CD8+ T cells, 12.3+/−5% expressed GITR and 9.7+/−3.4%) expressed OX40 (FIG. 2A). GITR and OX40 antibody binding density on RCC-associated T cells was also evaluated. The density of the antibodies binding GITR and OX40 was significantly higher on Tregs than on CD8+ Tcells or CD4+ Tconv cells (FIG. 2B). Thus, OX40 and GITR are similarly expressed by tumor-associated T cells, and are differentially higher on Tregs compared with CD8+ Tcells and CD4+ Teff cells.

Figure 2C:
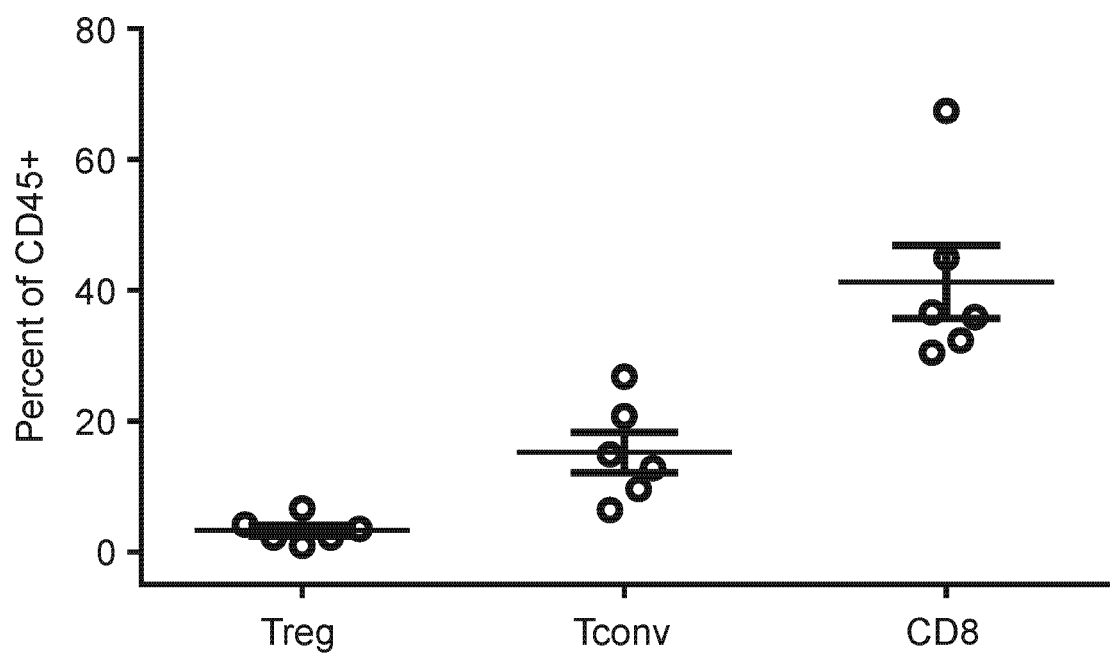
FIG. 2C depicts a graph summarizing the frequency of Treg, Tconv and CD8 cells within the immune infiltrate (CD45+) in renal cell carcinoma tissues.

The Treg cells are a minor fraction of the CD45+ immune cells infiltrating renal cell carcinoma tissue, comprising 3.29+/−0.82%, whereas CD4+ Tconv comprise 15.3+/−3% and CD8+ T cells 41.29+/−5.6% (FIG. 2C).

Methods

Enrichment of PBMC from Concentrated Whole Blood

Primary human lymphocytes were isolated from concentrated whole blood provided by the Stanford Blood Bank by first diluting blood 1:4 in Phosphate Buffered Saline (PBS, without Ca2+ and Mg2+). Peripheral Blood Mononuclear Cells (PBMC) were isolated using a Ficoll gradient underlay (Ficoll-Paque PLUS, GE Healthcare Life Sciences, Pittsburgh, Pa.). The harvested buffy layer was washed twice with PBS and counted. Cells were re-suspended at 50*10e6c/mL in PBS+2% Fetal Bovine Serum (FBS) and processed with CD3 negative enrichment kit (Stem Cell Tech Vancouver, BC) according to manufacturer's instructions.

Isolation and Analysis of Tumor Associated Lymphocytes: Digestion of Human Tumor Samples Primary tumor tissue was received whole and processed in house. The tissue was cut into small pieces with a scalpel or razor blade to ≤0.5 cm$^3$. Enzymatic dissociation was performed using a Human Tumor Dissociation Kit (Miltenyi Biotec, San Diego, Calif.). Monosuspension of the tumor was ensured by passing cell suspension over a 70 um strainer. Lysis of RBC was run (if appropriate) using ACK lysis buffer (Thermo Fisher Scientific, Waltham, Mass.) for 5 minutes at RT. Processed tumor samples were frozen and banked for future analysis at −80° C. in 90% human serum+ 10% DMSO. For analysis, frozen dissociated tumor cells were thawed into RPMI supplemented with 10% HI FBS and rested overnight before FACS analysis. Cells were washed from media and re-suspended in FACS buffer.

Antibody Staining and Flow Cytometric Analysis

A control panel was used so background of the antibody could be corrected with a Florescence Minus One (FMO) which did not include intracellular antibodies or Alexa 647 (A647) antibodies. Cells were stained with a A647-conjugated m3G7 antibody at 1 pg/ml along with antibodies specific for human surface receptors CD45, CD3, CD4, CD8 all from BD (BD Biosciences, San Jose, Calif.) diluted 1:50 in FACS buffer and a LIVE/DEAD Fixable Violet Cell Stain (Thermo Fisher Scientific, Waltham, Mass.). Foxp3 fix perm kit (eBioscience, San Diego, Calif.) was used to stain cells with intracellular markers Helios (22F6, Biolegend) and Foxp3 (259D, Biolegend) per manufacturer's instructions.

Analysis and Gating for Flow Cytometric Analysis.

Samples were analyzed post acquisition using Flow Jo software (Treestar, CA). Live immune cells were identified and gated as live/dead dye negative, CD45hi. CD4+ conventional cells (CD3+CD4+ Foxp3−), CD8+ cells (CD3+), and Tregs (CD3+CD4+ Foxp3+ Helios+/−). Mean fluorescence intensity of A647 was used to examine relative fluorescent signal and percent expression across samples using FMO samples to set gating and single color controls to set compensation. Data values were exported to GraphPad Prism software for graphical representation and statistical analysis. Data sets were analyzed using paired one-way ANOVA with Geisser-Greenhouse correction and Dunnets multiple comparison correction, or un-paired students T test as indicated. P value significance is characterized as <0.05* significant, <0.01 more significant, <0.001* highly significant.

Example 3 Determination of Kinetics and Affinity of GITR/IgG Interactions in Different Species This example shows the kinetics and affinity of human GITR/IgG, cynomolgus GITR/IgG, and mouse GITR/IgG interaction at 37° C. with different anti-GITR antibodies. See Tables 6 and 7.

TABLE 6

| mAb | hGITR kinetics (37° C.) | | | | cGITR kinetics (37° C.) | | | |
|---|---|---|---|---|---|---|---|---|
| | $k_a$ (1/Ms) | $k_d$ (1/s) | $t_{1/2}$ (min) | $K_D$ (nM) | $k_a$ (1/Ms) | $k_d$ (1/s) | $t_{1/2}$ (min) | $K_D$ (nM) |
| m3G7 | | | | >100 | | | | >100 |
| h3G7 H1 | | | | | | 7.8E-02 | 0.15 | >100 |
| h3G7 AM | 1.1E+06 | 1.9E-02 | 0.61 | 17 | 6.7E+05 | 8.8E-03 | 1.3 | 13 |
| h3G7 R5 | 9.0E+05 | 4.5E-03 | 2.6 | 5.0 | 6.0E+05 | 3.8E-03 | 3.0 | 6.4 |
| h3G7 LF | 6.9E+05 | 1.5E-02 | 0.76 | 22 | 3.3E+05 | 2.3E-02 | 0.51 | 69 |
| m10H2 | 3.5E+05 | 7.7E-04 | 15 | 2.2 | — | 7.3E-03 | 1.6 | >100 |
| h10H2 HU | — | 5.63E-02 | 0.21 | >100 | — | — | — | >100 |
| h10H2 AM | 2.33E+05 | 1.54E-03 | 7.5 | 6.6 | — | 1.1E-02 | 1.1 | >100 |

TABLE 7

| mAb | mGITR kinetics (37° C.) | | | |
|---|---|---|---|---|
| | $k_a$ (1/Ms) | $k_d$ (1/s) | $t_{1/2}$ (min) | $K_D$ (nM) |
| anti-mGITR r18H12 mIgG2a | 2.2E+05 | 4.9E-04 | 24 | 2.2 |
| anti-mGITR r21B6 mIgG2a | 3.1E+05 | 6.5E-03 | 1.8 | 21 |

All experiments were performed on a Biacore T200 surface Plasmon resonance biosensor (GE Lifesciences, Piscataway N.J.).

a. Human GITR/IgG and Cynomolgus GITR/IgG Interactions

Sensor Chip Preparation

The sensor chip preparation was performed at 25° C. with a running buffer of 10 mM HEPES, 150 mM NaCl, 0.05% (v/v) Tween-20, pH 7.4. An anti-human Fc sensor chip was made by activating all flow cells of a Biacore CM4 sensor chip with a 1:1 (v/v) mixture of 400 mM EDC and 100 mM NHS for 7 minutes, at a flow rate of 10 µL/min. An anti-human Fc reagent (Goat Anti-Human IgG Fc, SouthernBiotech Catalog #2081-01) was diluted to 30 pg/mL in 10 mM Sodium Acetate pH 4.5 and injected on all flow cells for 7 minutes at 20 µL/min. All flow cells were blocked with 100 mM ethylenediamine in 150 mM Borate buffer pH 8.5 for 7 minutes at 10 µL/min.

Kinetics & Affinity Assay

The experiments were performed at 37° C. using a running buffer of 10 mM HEPES, 150 mM NaCl, 0.05% (v/v) Tween-20, pH 7.4, 1 mg/mL BSA.

Antibodies were captured from undiluted supernatants onto downstream flow cells (flow cells 2, 3 and 4) at a flow rate of 10 µL/min for 2 minutes. Different antibodies were captured on each flow cell. Flow cell 1 was used as a reference surface. Following capture of antibodies, analyte (buffer, hGITR, or cyGITR) was injected at 30 µL/min on all flow cells for two minutes. After the analyte injection, dissociation was monitored for 10 minutes followed by regeneration of all flow cells with three 1-minute injections of 75 mM Phosphoric Acid. For each captured antibody, the following analyte injections were performed: buffer, 20 nM hGITR, 200 nM hGITR, 20 nM cyGITR and 200 nM cyGITR. Buffer cycles were collected for each captured antibody for double-referencing purposes (double-referencing as described in Myszka, J. Mol. Recognit. 12:279-284 (1999). The double-referenced sensorgrams were fit globally to a simple 1:1 Langmuir with mass transport binding model.

b. Mouse GITR/IgG Interactions

Sensor Chip Preparation

The sensor chip preparation was performed at 25° C. with a running buffer of 10 mM HEPES, 150 mM NaCl, 0.05% (v/v) Tween-20, pH 7.4. An anti-mouse Fc sensor chip was made by activating all flow cells of a Biacore CM4 sensor chip with a 1:1 (v/v) mixture of 400 mM EDC and 100 mM NHS for 7 minutes, at a flow rate of 10 µL/min. An anti-mouse immunoglobulin reagent (Rabbit anti-mouse immunoglobulin antibodies from Biacore Mouse Antibody Capture Kit, GE Lifesciences Catalog # BR-1008-38) was diluted to 60 pg/mL in 10 mM Sodium Acetate pH 5.0 and injected on all flow cells for 7 minutes at 20 µL/min. All flow cells were blocked with 100 mM ethylenediamine in 150 mM Borate buffer pH 8.5 for 7 minutes at 10 µL/min.

Kinetics & Affinity Assay

The experiments were performed at 37° C. using a running buffer of 10 mM HEPES, 150 mM NaCl, 0.05% (v/v) Tween-20, pH 7.4, 1 mg/mL BSA.

Purified antibodies were captured at 10 pg/mL onto downstream flow cells (flow cells 2, 3 and 4) at a flow rate of 10 µL/min for 2 minutes. Different antibodies were captured on each flow cell. Flow cell 1 was used as a reference surface. Following capture of antibodies, analyte (buffer, or mGITR) was injected at 30 µL/min on all flow cells for two minutes. After the analyte injection, dissociation was monitored for 10 minutes followed by regeneration of all flow cells with one 3-minute injection of 10 mM Glycine pH 1.7. A 5-membered dilution series of mGITR was analyzed using this method, where the top concentration was 300 nM and the dilution factor was 3-fold. The 33 nM dilution was run in duplicate. Buffer cycles were collected for each captured antibody for double-referencing purposes (double-referencing as described in Myszka, J. Mol. Recognit. 12:279-284 (1999). The double-referenced sensorgrams were fit globally to a simple 1:1 Langmuir with mass transport binding model.

Example 4: GITR Antibody Binding to Activated T Cells and Tregs

This example illustrates that different anti-GITR antibodies bind activated Teffectors and Tregs similarly with a dose response.

Figure 3A:
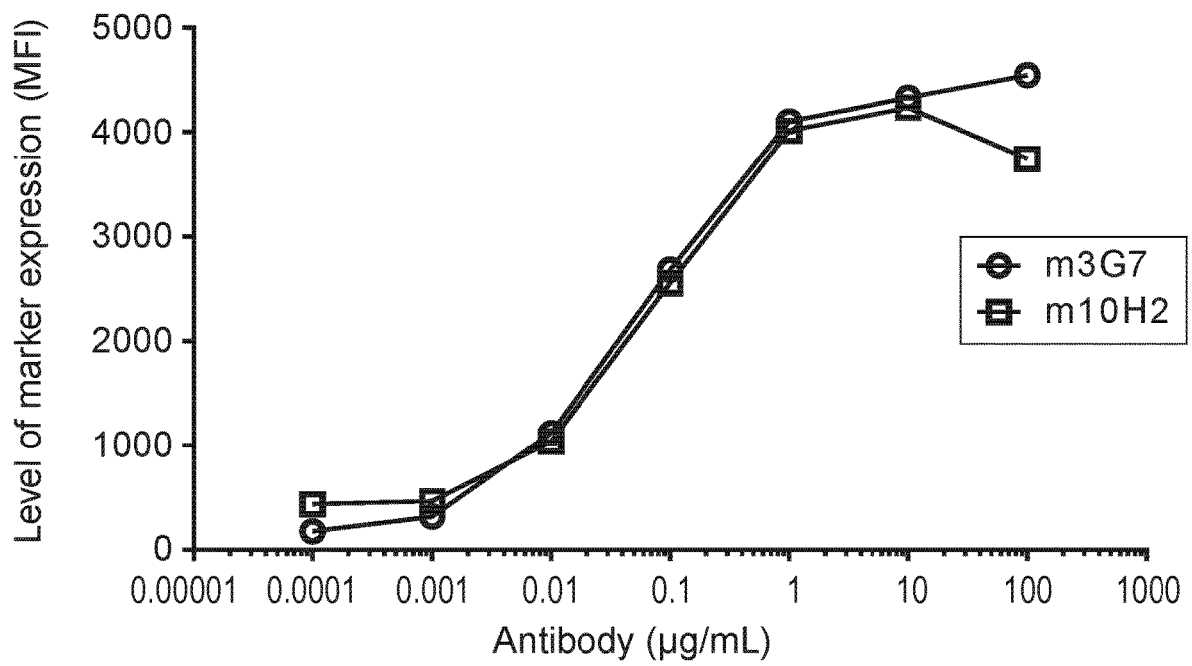
FIG. 3A shows a graph summarizing anti-GITR antibodies m3G7 and m10H2 binding to activated T cells.
Figure 3B:
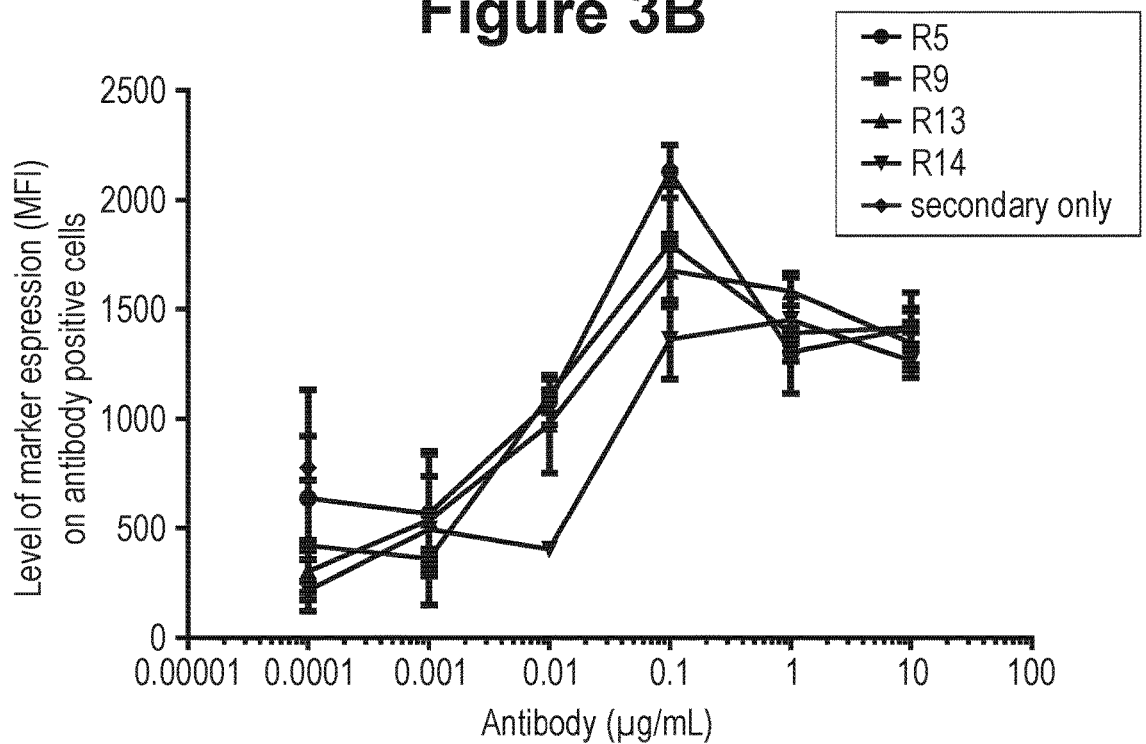
FIG. 3B shows a graph summarizing binding of anti-GITR antibodies R5 (h3G7 R5), R9 (h3G7 N9), R13 (10H2 N13), and R14 (10H2 N14) to activated Tregs.

Anti-GITR antibodies were evaluated for their binding characteristics to T cells and Tregs. To increase GITR expression on freshly isolated peripheral blood T cells, purified T cells and Tregs were activated in vitro. GITR antibodies m3G7 and m10H2 showed similar binding to activated T cells as evaluated in mean fluorescence intensity of a secondary antibody binding to the anti-human GITR antibodies (FIG. 3A). GITR antibodies R5 (h3G7R5), R9 (h3G7N9) and R13 (10H2N13) had similar binding patterns to the activated Tregs, and antibody R14 (10H2 N14) had lower density binding compared to the other antibodies (FIG. 3B).

Methods

T Cell Enrichment and Activation In Vitro.

Primary human lymphocytes were isolated from concentrated whole blood provided by the Stanford Blood Bank by first diluting blood 1:4 in Phosphate Buffered Saline (PBS, without Ca2+ and Mg2+). Peripheral Blood Mononuclear Cells (PBMC) were isolated using a Ficoll gradient underlay (Ficoll-Paque PLUS, GE Healthcare Life Sciences, Pittsburgh, Pa.). The harvested buffy layer was washed twice with PBS and counted. Cells were resuspended at 50*10e6c/mL in PBS+2% Fetal Bovine Serum (FBS) and processed with CD3 negative enrichment kit (Stem Cell Tech Vancouver, BC) according to manufacturer's instructions. After enrichment, cells were counted and frozen in aliquots of 10-20*10e6 in 90% FBS 10% DMSO freeze media for future use. For activation, a vial of cells from a donor T cell was thawed and rested overnight in R10c (RPMI 1640+10% FBS+1×NEAA+1×Sodium Pyruvate+1×Pen-Strep) at 1*10e6 cells/mL in a T75 flask. Cells were counted and stimulated for 48 hours with Dynabeads Human CD3/28 T cells activating beads at a 1:1 bead to cell ratio (Thermo Fisher). After 48 hours the cells were removed from media and washed with 1×PBS. Cells were titrated into a 96 well plate where they were stained with unlabeled mouse anti-human GITR antibodies (100-0.001 ug/mL) in PBS and incubated for 30 minutes at 37° c. Unbound antibody was washed from the cells and an APC labeled Fc gamma (Fcγ) Fragment Specific goat-anti-mouse affiniPure F(ab')$_2$ IgG (Jackson ImmunoResearch Laboratories Inc, West Grove, Pa.) was used to detect primary bound antibody. Following secondary stain the plate was washed with 1×PBS and spun at 335×g (1200 rpm). Wells were re-suspended in PBS+2% PBS and acquired on HTS.

Sorting and Expansion of Primary Tregs

Treg isolation and expansion was based on the protocol by Putnam et al. (Diabetes. 58(3):652-62 (2009)). Specifically, primary human lymphocytes were isolated from concentrated whole blood provided by the Stanford Blood Bank by first diluting blood 1:4 in Phosphate Buffered Saline (PBS, without Ca2+ and Mg2+). Peripheral Blood Mononuclear Cells (PBMC) were isolated using a Ficoll gradient underlay (Ficoll-Paque PLUS, GE Healthcare Life Sciences, Pittsburgh, Pa.). The harvested buffy layer was washed twice with PBS and counted. Cells were re-suspended at 50*10e6c/mL in PBS+2% Fetal Bovine Serum (FBS) and processed with CD4 negative enrichment kit (Stem Cell Tech Vancouver, BC) according to manufacturer's instructions. After enrichment, cells were counted and prepared for FACS sorting.

Treg staining buffer was prepared as PBS with 2% Normal Mouse Serum (Jackson ImmunoResearch Laboratories Inc, West Grove, Pa.) and 2% Human AB Serum (Corning CellGro, Manassas, Va.). CD4 negative enriched cells were stained for 30 minutes at RT in Treg staining buffer with CD3, CD4, CD8, CD25, and CD127 diluted 1:50 except CD25 which was stained diluted at 1:12.5. All antibodies provided by BD. (CD3-APC (UCHT1), CD4:PacBlue (RFP-T4, BD26986), CD8:BV786 (HIT8a, BD555635), CD127: PECy7 (M21, BD650822), CD25:PE (2A3, BD340938). After stain cells were washed and resuspended at 50*10e6 c/mL in Treg buffer. FACS sorting was run on the Aria platform (BD Biosciences, San Jose, Calif.). Tregs, identified by their phenotypic signature of CD3+CD4+ CD25hiCD127low, were FACS sorted and checked for 98%+ purity by acquiring a small fraction of the sorted sample. If appropriate cells were run through a second sort to maximize purity.

Cells from the FACS sort were counted and resuspended at 0.25*10e6c/mL in Treg expansion media composed of Roswell Park Memorial Institute (RPMI)-1640 supplemented with 5% Human AB Serum and 1×MEM-NEAA, Sodium Pyruvate, and Penicillin-Streptomycin (LifeTechnologies, San Diego, Calif.) with 1:1 Treg expander beads (Life Technology, San Diego, Calif.). After two days the media volume was doubled and recombinant human IL-2 was added at 300IU/mL. On day 5, 7, and 9 cells were counted and subcultured to 0.25*10e6c/mL with 300IU/mL IL2. In addition to the subculture on day 9, 1:1 Treg expander beads were added to the culture for a "re-stim" of the Tregs. On day 13 cells were harvested for binding and functional assays.

Phenotype of Primary Expanded Tregs

Cultured Tregs would be tracked throughout expansion to check purity. Cells were re-suspended in FACS buffer, PBS with 2% FBS for analysis using fluorophore conjugated CD markers. FACS antibodies against GITR and other CD lymphocyte markers were prepared in FACS buffer at the appropriate concentration and incubated for 30 minutes at RT. Treg purity staining utilizes intracellular targets and were processed with Foxp3 fix/perm kit (Affymetrix/eBiosciense, San Diego, Calif.). Stained cells were resuspended in fresh FACS buffer and analyzed on a FACS analyzer LSRII or Fortessa (BD Biosciences, San Jose, Calif.). To generate kinetic and binding data unconjugated antibody was titrated from 10-0.001 ug/mL (1:10 in serial dilutions, triplicate wells per concentration) and incubated at 4c for 60 minutes with 1*10e5 expanded day 12 Tregs per well. Unbound antibody was washed from cells and an A647 labeled Fc gamma (Fcγ) Fragment Specific goat-anti-human affiniPure F(ab')$_2$ IgG was used to detect bound antibody (Jackson ImmunoResearch Laboratories Inc, West Grove, Pa.). Analysis of stained cells completed with FlowJo (Treestar). Geometric mean of APC was used to calculate EC50 by log transforming the molar concentration and generating a non-linear fit curve in GraphPad Prism.

Example 5: GITR Antibodies Mediate Cell Cytotoxicity

Figure 4A:
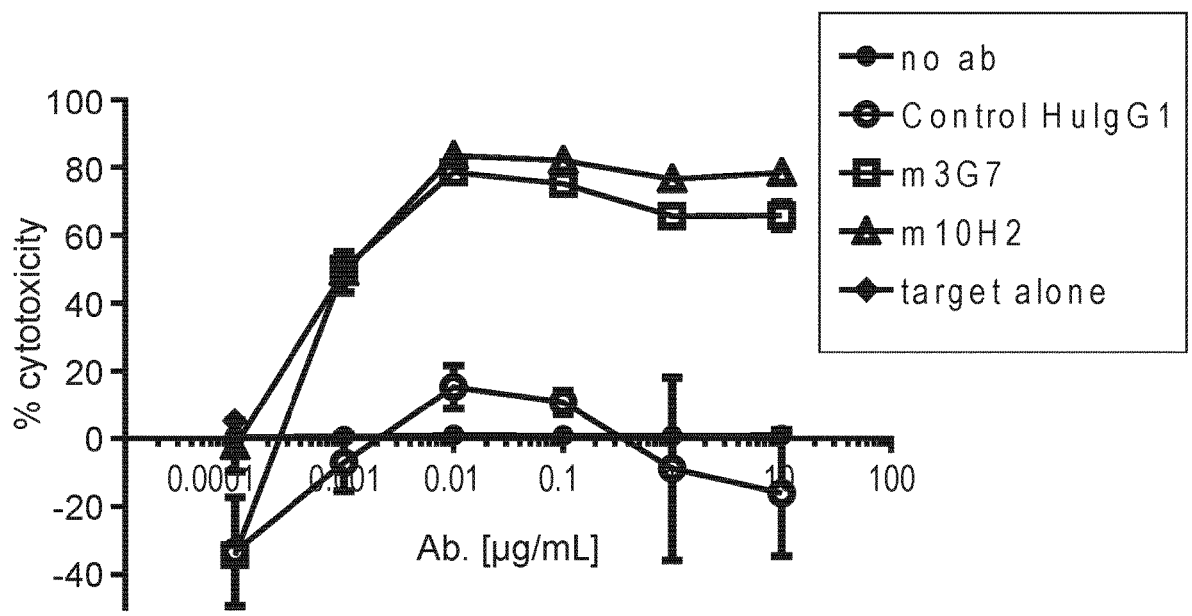
FIG. 4A shows that GITR antibodies mediate cell cytotoxicity in the in vitro assay of antibody-dependent cell cytotoxicity (ADCC) mediated by un-fractionated PBMC. The hIgG1 GITR antibodies (m3G7 and m10H2) enabled macrophages to mediate a dose dependent killing of GITR+ T cells.

This example shows that GITR antibodies mediate cell cytotoxicity in two in vitro assays: 1) antibody mediated cell cytotoxicity (ADCC) mediated by un-fractionated PBMC, and 2) antibody mediated cell phagocytosis (ADCP) mediated by macrophages.

hIgG1 anti-GITR antibodies m3G7 and m10H2 exhibited similar levels of ADCC of a GITR+ T cell line compared with isotype control, with maximal target cell killing at 0.01 ug/ml of 78.5% for m3G7 and 83.4% for m10H2 (FIG. 4A)

Figure 4B:
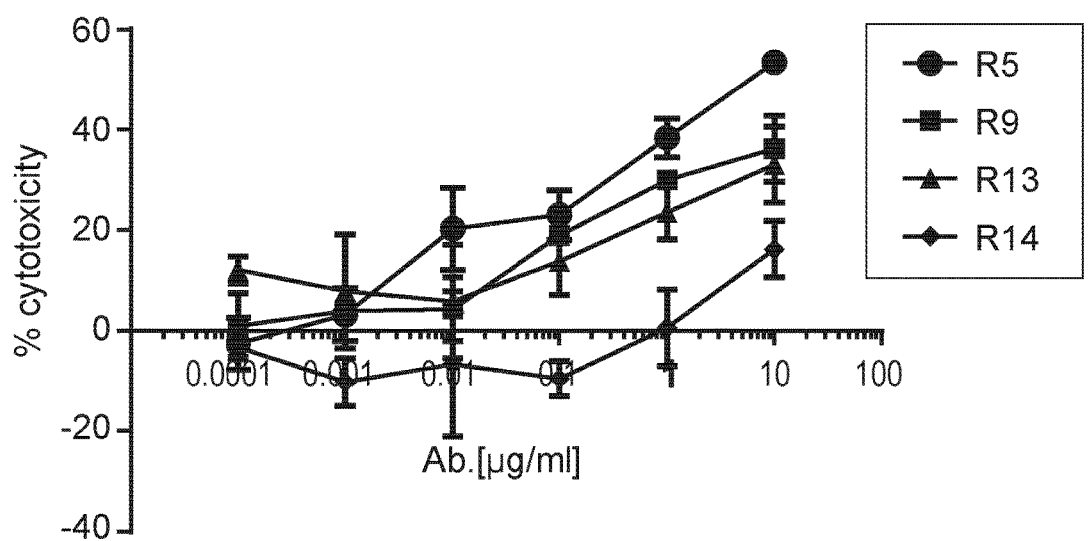
FIG. 4B shows that GITR antibodies mediate cell cytotoxicity in the in vitro assay of antibody-dependent cell phagocytosis (ADCP) mediated by macrophages. The hIgG1 GITR antibodies depicted are h3G7 R5 ("R5"), h3G7 R9 ("R9"), h10H2 R13 ("R13"), and h10H2 R14 ("R14").

Tumor associated macrophages (TAM) have been implicated as the cell population mediating antibody directed cytotoxicity of Tregs in mice (Simpson et. al. J. Exp. Med. 210(9): 1695-1710 (2013); Bulliard et. al. J. Exp. Med. 210(9): 1685-93 (2013)). We evaluated GITR antibody-mediated cytotoxicity of a GITR+ T cell line by human monocyte-derived macrophages. hIgG1 GITR antibodies enabled macrophages to mediate a dose dependent killing of GITR+ T cells (FIG. 4B). The GITR antibodies were not equivalent; antibody h3G7 R5 ("R5"), h3G7 R9 ("R9"), h10H2 R13 ("R13"), and h10H2 R14 ("R14"), had an EC50 of 919.7, 692.2, 4450. 2013 pM, respectively. Macrophage-mediated cytotoxicity was dependent on the Fc of the GITR antibody. Cytotoxic activity was lost with N297A mutation that reduced binding to FcR (Chao et al. Immunol. Invest. 38(1): 76-92 (2009)). (FIG. 4C).

Methods

ADCC Assay with Effector PBMC and GITR+ Target

Primary human lymphocytes were isolated from concentrated whole blood provided by the Stanford Blood Bank by first diluting blood 1:4 in Phosphate Buffered Saline (PBS, without Ca2+ and Mg2+). Peripheral Blood Mononuclear Cells (PBMC) were isolated using a Ficoll gradient underlay (Ficoll-Paque PLUS, GE Healthcare Life Sciences, Pittsburgh, Pa.). The harvested buffy layer was washed twice with PBS and counted. PBMC were re-suspended at 3*10e6 cells/mL in RPMI supplemented with 10% FBS and 1×MEM-NEAA, Sodium Pyruvate, and Penicillin-Streptomycin (Life Technologies, San Diego, Calif.). GITR+ Jurkat T cell line were stained in PBS with Cell Trace Violet (LifeTechnologies, San Diego, Calif.). After labeling, Jurkat's were re-suspended at 3*10e5c/mL. A dilutions series of the anti-GITR antibodies were made by titrating 1:10 a 40 ug/mL solution to 0.0004 ug/mL (6 concentrations). 50 uL of titrated antibody was plated per well of a 96-well U-bottom plate along with 50 uL of labeled Jurkats and 100 uL of PBMC to create a 20:1 effector to target ratio with final antibody [10-0.0001 ug/mL]. The plates were incubated overnight (~18 hours) and the next day the plates were harvested for analysis.

The U-well plates were spun at 1200 rpm to remove media from cells and washed with PBS. PI (Life Technologies, San Diego, Calif.) at 1:500 in PBS was added in 30 uL per well for 10 minutes at room temp. To the PI approximately 100 uL of PBS supplemented with 2% FBS (to quench PI) was added bringing the volume to 100-150 uL per well with before HTS analysis. Just prior to acquisition, 1*10e4 Count Bright counting beads (Life Technologies, San Diego, Calif.) were added to each well. The ratio of viable Treg target count to bead count would be used to normalize across the plate and be compared to ratio of control IgG1 to generate the percent cytotoxicity.

ADCP Assay: Monocytes Derived Macrophage Effectors and Expanded Treg Target

PBMC were prepared as described above. Using the EasySep™ CD14+ negative enrichment kit (Stem Cell Tech Vancouver, BC) monocytes were positively enriched and resuspended in R10c supplemented with 20 ng/mL MCSF (R&D systems, Minneapolis, Minn.) at 1*10e6 cells/mL and plated in a T175 with 55-65 mL cell suspension per flask. Monocytes strongly adhered to the tissue culture flask and were not removed when the media was refreshed with new R10c supplemented with 20 ng/mL MCSF on day 2 and on day 5 of culture. The media on day 5 was also supplemented with 10 ng/mL IL10 (R&D systems, Minneapolis, Minn.). After a week of the culture the cells were harvested and plated at 1*10e5 cells/well in 96 well flat plates in activation media consisting of 1 mg/mL PGE2 (Sigma, St Louis, Mo.), 10 ng/mL each TNF, IL1B, and IL6 (all R&D systems, Minneapolis, Minn.). The following day the plated monocytes were washed out of activation media and 5*10e4 Cell Trace Violet labeled Jurkat bulk GITR+ cells were added per well (for a final effector to target ratio of 2:1) along with either control IgG1 antibody or titrated GITR antibodies. The plates were incubated overnight (~18 hours) and the next day the plates were harvested for analysis. Cells from the 96-well flat plates were thoroughly triturated and transferred to 96-well U-well plate. The plate was spun at 1200 rpm to remove media from cells and washed with PBS. The remainder of the procedure follows section ADCC Acquisition and Analysis beginning with the PI stain.

Example 6: T Cell Cytokine Production Enhancement by the GITR Antibodies

The example shows that the anti-GITR antibodies of the present invention enhance T cell cytokine production in vitro.

GITR is a co-stimulatory receptor on T cells. Ligation of GITR with its ligand causes enhanced proliferation of differentiated T helper cells (Tone et al. Proc. Natl. Acad. Sci. 100(25): 15059-15064 (2003)). Boosted T cell activation and pro-inflammatory cytokine production, such as IFNγ translates to tumor regression in mouse models (Ko et. al. J. Exp. Med. 2005. 202(7): 885-891 (2005). In this example, the GITR antibodies for T cell activation by secretion of IFNγ and TNFα was evaluated. A T cell hybridoma (3A9; Dustin et al. J. Immunol. 157(5):2014-2021 (1996)) expressing human GITR was activated with an anti-CD3 antibody (Clone 2C11, Ebioscience) and increasing concentrations of plate immobilized the anti-GITR antibodies (h3G7 R5 ("R5"), h3G7 R9 ("R9"), h10H2 R13 ("R13"), and h10H2 R14 ("R14")). The four GITR antibodies caused enhanced secretion of TNFα in a dose dependent manner until 0.01-0.1 μg/ml. At higher GITR antibody concentrations, the TNFα secretion dropped (FIG. 5A). A similar experiment was conducted with the GITR expressing 3A9 cells and CD3 antibodies 2C11 in the presence of a B cell lymphoma line (LK35.2) to provide FcRs necessary for clustering and signaling of GITR (Zhou et al. Proc. Natl. Acad. Sci. 105(14): 5465-5470 (2008)). GITR antibodies R5, R9, R13 and R14 were added in solution and all four enhanced secretion of TNFα between concentrations of 0.01 and 10 μg/ml (FIG. 5B).

The effect of GITR antibodies on cytokine secretion of activated primary T cells was evaluated in vitro. GITR antibodies R5, R9, R13 and R14 caused dose dependent increases in secreted IFNγ and TNFα from CD4+ and CD8+ T cells peaking between 0.01 and 0.1 pg/ml, and then dropping off at higher concentrations (FIG. 5C and FIG. 5D). Accordingly, this example shows that the GITR antibodies have T cell activating attributes that are dose-dependent.

Methods

GITR Antibody T Cell Agonist Assay

To prepare immobilized GITR antibody culture plates, sterile Nunc maxisorp 96-flat well plates were coated overnight at 4c with 100 uL of 2 ug/mL Anti-Mouse and Anti-Human Fc fragment specific protein diluted in PBS. After washing 2× with 1×PBS, 100 uL of Mouse CD3 (2C11) at 10 ng/mL was incubated at 37° c. for 60-90 minutes. GITR antibodies R5, R9, R13 and R12 were titrated from 10-0.0001 ug/mL in PBS and 100 uL was added to each well with triplicates for each concentration. The plate was incubated at 37° c. for 60-90 minutes and washed before adding cells Using the prepared immobilized GITR plates, 50,000 human GITR+3A9 cells were plated per well in 200 uL of DMEM+10% FBS media. After 48 hrs of culture the supernatants were collected for cytokine analysis using the Mouse Soluble Protein Assay (Becton-Dinkinson).

The human GITR+3A9 cells were also tested in a soluble GITR antibody assay utilizing LK35.2, a mouse B cell lymphoma line. In this assay a 2:1 ratio of 3A9 to LK35.2 was plated along with mouse anti-CD3 antibody (2C11) at 0.1 ug/mL and GITR antibodies titrated from 10-0.0001 ug/m L.

Human cytokine secretion was also assayed using freshly isolated human pan T cells (CD4+CD8+) and plating them onto immobilized plates prepared as described above. 100,000 cells were plated per well in RPMI+10% FBS and supernatants were collected after 4 days of incubation.

Example 7: GITR Immunohistochemistry Staining

This example describes the optimization of an anti-GITR antibody as a immunohistochemistry (IHC) reagent that specifically stains formalin fixed paraffin embedded (FFPE) tissues.

The anti-human GITR antibody m10H2 was evaluated and showed correlated density of staining of T cell lines expressing no, low and high human GITR (FIG. 6A, FIG. 6B, and FIG. 6C). Confirmation of the minimal, low and high GITR expression is shown by flow cytometry staining surface protein with the m10H2 clone (FIG. 6D) and quantitative PCR and normalization to actin B expression (Example 6E). Furthermore, FFPE tissues isolated from NSCLC tumors were stained with m10H2 (FIG. 6F) or isotype control antibody (FIG. 6G). The m10H2 staining was confined to the membrane of cells within the mononuclear infiltrate in the tumor tissue (FIG. 6F). Accordingly, this example demonstrates that m10H2 is a validated anti-GITR antibody that can be used on FFPE tissues to quantify GITR expression.

Methods

Surface Staining on GITR Overexpressing Jurkat Cell Lines:

Prior to the IHC analysis, the three Jurkat lines were analyzed for surface GITR expression by FACS using an A647 labeled m10H2 antibody. These lines included a parent Jurkat cell line as well as two lines generated by transfection of a GITR plasmid into the Jurkat parent cells. Approximately 5*10e6 cells from each line was stained with labeled antibody at a concentration of 1 ug/mL. Following stain cells were washed from unbound antibody using 1×PBS and analyzed by FACS.

Results

By FACS the Jurkat parent cells had no detectable GITR expression while the two transduced lines had positive staining. There was approximately a log and a half fold difference between the median GITR expression on the two lines leading us to distinguish them as GITR+ low expresser and GITR+ high expresser.

Quantitative GITR Expression Analysis by PCR:

Quantitative analysis of GITR expression on Jurkat parent, GITR+ low, and GITR+ high was run by qPCR. RNA was isolated from 5-10*10e6 cells from each line using the RNeasy Mini Kit (Quiagen). A cDNA template was made using 200 ng of the isolated RNA using the High Capacity cDNA Reverse Transcription kit (Thermo Fisher). TaqMan FAST reagents were used to run the qPCR along with the cDNA template. Primers for both the housekeeping gene Actin B (Hs99999903_m1) and a custom specific GITR primer were run in each reaction. The custom GITR primer was generated by ABI using the vector sequence of the GITR transfected plasmid (sequence not disclosed by ABI). The qPCR was run on a Viia7 system according to manufacturer's instruction and TaqMan FAST thermal cycling specifications. The delta Ct was calculated using the formula: $2^{\wedge}(-\{Ct(GITR)-Ct(ActB)\})$.

Results

The qPCR analysis confirms the expression ranking of the three lines with the GITR+ low having 2.7 logs higher expression than parent and the GITR+ high line having 2 logs higher GITR expression than the GITR+ low line.

IHC Cell Processing:

With GITR expression levels assayed by FACS and qPCR, cells from the Jurkat parent (GITR negative), GITR+ low, and GITR+ high lines were prepared and processed for sectioning as follows. Between 20 and 30*10e6 cells were collected in a 50 mL conical and spun at ~750×g for 10 minutes. After removing the supernatant the pellet was transferred to a 15 mL conical in 10% neutral buffered formalin and spun at ~750×g for 10 minutes. HistoGel prepared at 50° c. was mixed with the cell pellet and allowed to chill by refrigeration at 4° C. The HistoGel cell pellet was then transferred into 10% neutral buffered formalin for fixation for >12 hours and transferred to a cassette for paraffin embedding. Sectioning of slides was performed to generate slices of pellet at 4 uM thickness. For IHC staining the UltraVision One Detection System from Thermo Scientific was used. Briefly, slides were prepared by baking at 60° C. for 1 hour and deparafinized in three rounds of xylene wash for three minutes each. The sectioned pellet was rehydrated by sequential incubations for two minutes each in 100% ETOH (2×), 95% ETOH (1×), 70% ETOH (1×), and PBS (1×). Antigen retrieval was performed by processing slides for 5 minutes in DIVA buffer and Decloaking chamber (both from Biocare Medical) heated to 110° C. and pressurized to 5 PSI followed by two washes in PBS. Slides were blocked in 3% $H_2O_2$ (Peroxidase) for 10 min and washed in PBS. Primary antibody, m10H2, was diluted to 1 ug/mL in blocking solution and slides were incubated overnight at 4° C. After washing in PBS (3×) for 3 min slides were incubated in HRP Polymer for 30 minutes at Room Temperature and washed in PBS (3×). DAB reagent was prepared and slides were exposed for 5 minutes. A counterstain was run with Hematoxylin and, after dehydration, mounted slides were complete. The slides were analyzed for GITR levels.

Staining of NSCLC Samples

Prepared slides of Non-Small Cell Lung Carcinoma (NSCLC) samples were received from an internal bank. The UltraVision One Detection System from Thermo Scientific was used as described above. As with the staining of the cell pellets 1 ug/mL of m10H2 anti-GITR antibody was assayed along with a mouse IgG1 control antibody at 5 ug/mL.

Example 8: Anti-Tumor Activity of GITR Antibodies

This example shows that the anti-mouse GITR antibodies with a mIgG2a isotype have tumor growth reduction activity in a therapeutic treatment model of CT26 colon carcinoma.

The mIgG2a most closely reflects the human IgG1 isotype that can mediate ADCC activity while the mIgG1 isotype most closely resembles hIgG2a that has minimal ADCC activity (Nimmerjahn and Ravetch, Science, 310: 1510-1512 (2005)).

The anti-GITR 21B6 mIgG2a isotype antibody had anti-tumor activity whereas the mIgG2a isotype control antibody did not (FIG. 7A-FIG. 7D). The 21B6 mIgG2a exhibited 95%, 94%, 102% tumor growth inhibition at 0.2, 1 and 5 mpk (mg/kg) respectively (Table 8, FIG. 7A-FIG. 7D). The mIgG1 isotype induced 33%, 9%, and 22% tumor growth inhibition at 0.2, 1 and 5 mg/kg respectively (Table 9, FIG. 7E-FIG. 7H). At the end of study (43 days post initial dose), 80% (8/10) of mice survived in the 5 mpk mIgG2a group, while 44.4% (4/9) survived in the 1 mg/kg mIgG2a group, and 40% (4/10) survived in the 0.2 mg/kg mIgG2a group (Table 8 and Table 9, FIG. 7I). The mIgG1 treatment resulted in no survival; all needed to be sacrificed due to tumor burden prior to the end of study (43 days) (Table 8 and Table 9, FIG. 7I).

TABLE 8

| Dose | TGI | % Tumor Free |
|---|---|---|
| 5 mpk | 102.25 | 80% |
| 1 mpk | 94.17 | 44.44% |
| 0.2 mpk | 95.30 | 40% |

TABLE 9

| Dose | TGI | % Tumor Free |
|---|---|---|
| 5 mpk | 21.76 | 0 |
| 1 mpk | 8.70 | 0 |
| 0.2 mpk | 33.19 | 0 |

The inhibition of tumor growth mediated by 21B6 IgG2a correlated with an increase in the ratio of CD8:Treg infiltrating the tumor (FIG. 7J). The 1 mg/kg dose of 21B6 IgG2a resulted in the highest CD8:Treg ratio (10.9×IgG2a isotype control, p=0.049). Treatment with 21B6 IgG2a also resulted in an increase in the ratio of CD4 Teff:Treg infiltrating the tumor (FIG. 7K) at all doses with the 0.2 mg/kg 21B6 IgG2a dose providing the highest mean ratio (4.7× higher than IgG2a isotype control). Statistical significance was observed between 5 mg/kg, 1 mg/kg, and 0.2 mg/kg compared to isotype IgG2a control with p values of 0.043, 0.003, and <0.0001, respectively. These changes were not observed in the mice treated with the 21B6 IgG1 where the CD8 T cell:Treg and CD4 Teff cell:Treg showed no statistical significance compared to IgG1 isotype control (FIG. 7J and FIG. 7K).

Tumor growth inhibition corresponded with a loss of intratumoral Tregs in the 21B6 IgG2a treated mice (FIG. 7L). All dose levels of 21B6 IgG2a reduced the number of Treg cells per gram associated with the primary tumor although these changes were not statistically significant. There were reductions of CD8+ T cells at 5 mg/kg (FIG. 7M), and CD4+T effector (Teff) cells at 5 mg/kg and 1 mg/kg (FIG. 7N), although these changes were not statistically significant. Similarly, all doses of 21B6 mIgG2a reduced the proportion of Tregs from 2.56% within the CD45+ immune cells infiltrating the tumors to 0.69% (p=0.0018) with the 0.2 mg/kg dose, to 0.42% (p=0.0005) with the 1 mg/kg dose, and to 1.29% (p=0.0287) with the 5 mg/kg dose (FIG. 7O). The proportion of Treg in the immune infiltrate was not affected by 21B6 mIgG1 treatment (FIG. 7O). Changes in the proportion of CD8+ T cells and CD4+ Teff cells in the tumor infiltrate were non-significant (FIG. 7P and FIG. 7Q). Together, these analyses suggest that reduced tumor Tregs account for the enhanced Teffector cell:Treg ratio, anti-tumor efficacy and mouse survival following GITR antibody administration, which was dependent on a mIgG2a and not a mIgG1 Fc isotype.

T cell subset frequencies were evaluated in a peripheral immune compartment; the spleens of the tumor bearing, 21B6 treated mice. The 0.2 mg/kg dose had the most effect, reducing Tregs from 2.46% of CD45+ cells in control antibody treated mice to 1.11% (p=0.0006) in mIgG2a treated mice, and reducing CD4+ Teff from 15.06% of CD45+ cells in control antibody treated mice to 11.22% (p=0.0121) in mIgG2a treated mice (FIGS. 7R and 7T). Changes at other doses were non-significant. CD8+ T cells were unaffected at any dose (FIG. 7S).

Methods

Cloning and Expression of m21B6 IgG2a

Anti-mGITR 21B6 heavy and light chain variable domain DNA sequences were obtained from cDNA generated using RT-PCR from a Lewis Rat hybridoma fusion. The resulting translated amino acid sequence was codon optimized for Human Epithelial Kidney 293 expression using proprietary algorithms from Thermo Fisher Scientific Geneart. Synthesized codon optimized variable domains were then cloned into the mammalian expression vectors pARC mIg2a and pARC mKappa using BssHII/BstEII and ApaLI/PacI respectively. Correct clones for light and heavy chain constructs were sequence confirmed and correspondingly named h3G7R5-VL and h3G7R5-VH.

Antibody Expression and Purification

A 1:1 mass ratio of plasmids h3G7R5-VL and h3G7R5-VH were co-transfected into Expi293 cells using a PEI-based transfection protocol (0.5 mg each plasmid per 2 million cells). Five days post transfection, the transfected cell culture was harvested, centrifuged, and filtered using a 0.2 uM membrane. Filtered supernatant was then purified using Protein A affinity chromatography (MabSelect Sure, GE Healthcare Life Sciences, Pittsburgh, Pa.) and then sized to remove aggregated protein (Superdex S200 26/60 GE Healthcare Life Sciences, Pittsburgh, Pa.). SDS-PAGE in conjunction with Biacore analysis identified monomeric active protein fractions.

Syngeneic Tumor Model: CT26

Animals

Mice cohorts of 7-week old female BALB/c mice (BALB/cAnNCrl) obtained from Jackson Laboratories (Bar Harbour, Me.) and housed in a pathogen free facility at Pfizer (South San Francisco, Calif.) in accordance with the Institutional Animal Care and Use Committee (IACUC) protocol. The animals were 8-weeks old when initiated into the experiment.

Cell Culture

The mouse colon carcinoma cell lines CT26 (CRL-2638) was obtained from the American Type Culture Collection (ATCC, Manassas, Va.). The cells were propagated in recommended basic media containing 10% FBS and 1% penicillin-streptomycin solution (all Thermo Fisher Scientific, Waltham, Mass.). Cells were harvested with TrypLE Select (Thermo Fisher Scientific, Waltham, Mass.) and washed with a 2× volume of media containing serum before pelleting the cells. The pellet was re-suspended in basic media without serum and a cell count and viability check was performed. The CT26 cells were brought to a concentration of 2×10$^6$ cells per mL in basic media for injection.

In Vivo Experimental Protocol

To establish tumors, 100 uL of cell suspension was injected SC into the right flank of the mice. The implants were monitored until the tumors reached an average volume of approximately 80 mm$^3$ and were randomized into groups of mice having nearly equal average tumor volumes and SEM. 21B6 antibody was prepared for a dosing at 5, 1, and 0.2 mg/kg with an isotype control IgG1 (clone MOPC-21) and IgG2 isotype control (C1.18.4, Bioxcell, West Lebanon, N.H.) at 5 mg/kg. Treatment began on the day of randomization (Day 0). Mice were weighed and dosed IP every 2-3 days for a total of three doses.

Evaluation of Tumor Growth

Twice weekly the tumor length and width (in millimeter units) would be taken with digital calipers (Mitutoyo, Aurora, Ill.). Tumor volumes were calculated using the length and width values with the formula: $V=\frac{1}{2}L \times W^2$, where L (length) is defined as the longest diameter of the tumor and W (width) is perpendicular to L. Efficacy measurements were continued to day 20, and mice were continued to be monitored up to 40 days for survival analysis.

Tumor TIL and Splenocyte Analysis

Tumor and spleen were dissected from 4-5 mice per group one day after the last dose. Tumors were dissociated with program IMP-002 on the Miltenyi Octet (Miltenyi Biotec, San Diego, Calif.) according to manufacturer instructions. Spleens were manually dissociated over a 70 uM mesh filter and red blood cells were lysed with ACK buffer (Thermo Fisher Scientific, Waltham, Mass.). Both cell populations were washed with PBS and stained with the following fluorescence labelled antibodies for FACS analysis: LIVE/DEAD (Thermo Fisher Scientific, Waltham, Mass.), CD90.2, CD4, and CD8 all from BD Biosciences and GITR and CD45 from eBioscience. Following extracellular staining for 30 minutes at 4° c. the cells were washed with PBS+2% FBS and processed with the eBioscience Foxp3 Fix/Per kit (eBioscience, San Diego, Calif.) per manufacturer's instructions. Cells were stained with intracellular markers Foxp3-eFlour450 (eBioscience, San Diego, Calif.) and Ki-67-BV605 (BD Biosciences, San Jose, Calif.). Analysis of T cell subsets was conducted in FlowJo (FlowJo, Ashland, Oreg.) and plotted using GraphPad Prism software.

Example 9 Combination Therapy Using an Anti-GITR Antibody and Other Therapeutic Agent This example describes the evaluation of the anti-GITR surrogate antibody 21B6 mIgG2a in combination with other immune-targeting antibodies for therapeutic treatment of tumors.

The CT26 colon carcinoma model underwent complete tumor regression with single agent 21B6 IgG2a (Example 8), so the B16F10 melanoma model is evaluated because it is less responsive to single agent immune targeting therapy (See, e.g., Mosley et al., Cancer Immunology Research, 5(1)29-41 (2017)). The treatment protocol is similar to the studies described in Example 8: B16F10 tumors are implanted and once reach an average size of 80 mm$^3$ are randomized and treated with 3 doses of 1 mg/kg 21B6 IgG2a and the established efficacious dose of the combination partner IP every 2-3 days for a total of three doses. The doublet combination of the anti-GITR antibody 21B6 IgG2a with anti-PD-L1, anti-4-1BB, anti-OX40 and anti-PD-1 antibodies all show improved tumor growth inhibition in comparison to either single agent treatment alone.

These data show that the anti-GITR antibodies of the present invention can be combined with immune checkpoint inhibitors or T cell stimulatory antibodies for improved tumor growth inhibitory effects.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated antibody, or antigen binding fragment thereof, that specifically binds to GITR (Glucocorticoid Induced Tumor Necrosis Factor Receptor Family Related Protein) and comprises:
   a heavy chain variable region (VH) complementarity determining region one (CDR1) comprising the amino acid sequence of SEQ ID NO: 39, 40, or 41;
   a VH CDR2 comprising the amino acid sequence of SEQ ID NO:44 or 45;
   a VH CDR3 comprising the amino acid sequence shown in SEQ ID NO:29;
   a light chain variable region (VL) CDR1 comprising the amino acid sequence shown in SEQ ID NO:42;
   a VL CDR2 comprising the amino acid sequence shown in SEQ ID NO:43; and
   a VL CDR3 comprising the amino acid sequence shown in SEQ ID NO:38.

2. The isolated antibody of claim 1, wherein the antibody optionally comprises a constant region.

3. The isolated antibody of claim 2, wherein the constant region isotype is selected from the group consisting of $IgG_i$, $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P and $IgG_{4\Delta c}$ S228P.

4. An isolated antibody that specifically binds to GITR and comprises a heavy chain variable region (VH) comprising the amino acid sequence shown in SEQ ID NO: 12 and a light chain variable region (VL) comprising the amino acid sequence shown in SEQ ID NO: 11.

5. A pharmaceutical composition comprising the antibody of claim 1 or claim 4, and a pharmaceutically acceptable carrier.

6. A kit comprising the pharmaceutical composition of claim 5.

* * * * *

SEQUENCE LISTING

```
<160> NUMBER OF SEQ ID NOS: 130

<210> SEQ ID NO 1
<211> LENGTH: 110
<212> TYPE: PRT
<213> ORGANISM: Artificial Sequence
<220> FEATURE:
<223> OTHER INFORMATION: Synthetic Construct

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Ile Asn Phe Met Asn Trp Phe Gln Gln Lys Ser Gly Gln Pro Pro
        35                  40                  45

Lys Leu Leu Ile Tyr Ala Ala Ser Asn Gln Gly Ser Gly Val Pro Ala
    50                  55                  60
```

```
Arg Phe Ser Gly Ser Gly Ser Gly Thr Asp Phe Ser Leu Asp Ile His
 65                  70                  75                  80

Pro Met Glu Glu Asp Asp Thr Ala Met Tyr Phe Cys Gln Gln Lys Glu
                 85                  90                  95

Leu Pro Trp Thr Phe Gly Gly Gly Thr Lys Leu Glu Ile Lys
            100                 105                 110

<210> SEQ ID NO 2
<211> LENGTH: 119
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Gln Gln Ser Gly Pro Glu Arg Val Lys Pro Gly Ala
  1               5                  10                  15

Ser Met Lys Ile Ser Cys Lys Val Ser Gly Tyr Ser Phe Thr Asp Tyr
                 20                  25                  30

Thr Met Asn Trp Val Lys Gln Ser His Gly Lys Asn Leu Glu Trp Ile
             35                  40                  45

Gly Leu Ile Asn Pro Tyr Asn Gly Gly Ile Arg Tyr Asn Gln Lys Phe
 50                  55                  60

Lys Gly Lys Ala Ser Leu Thr Val Asp Lys Ser Ser Asn Thr Ala Tyr
 65                  70                  75                  80

Met Glu Leu Leu Ser Leu Thr Ser Glu Asp Ser Ala Val Tyr Tyr Cys
                 85                  90                  95

Ala Arg Ile Gly Gly Tyr Tyr Asp Ser Met Asp Tyr Trp Gly Gln Gly
            100                 105                 110

Thr Ser Val Thr Val Ser Ser
            115

<210> SEQ ID NO 3
<211> LENGTH: 111
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Ser Val Asp Asn Phe
                 20                  25                  30

Gly Ile Asn Phe Leu Asn Trp Phe Gln Gln Lys Pro Gly Lys Ala Pro
             35                  40                  45

Lys Leu Leu Ile Tyr Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Lys
                 85                  90                  95

Glu Leu Pro Trp Thr Phe Gly Gly Gly Thr Lys Val Glu Ile Lys
            100                 105                 110

<210> SEQ ID NO 4
<211> LENGTH: 119
<212> TYPE: PRT
<213> ORGANISM: Artificial Sequence
```

```
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Phe Thr Asp Tyr
            20                  25                  30

Thr Met Asn Trp Val Arg Gln Ala Pro Gly Lys Gly Leu Glu Trp Val
        35                  40                  45

Ala Leu Ile Asn Pro Tyr Asn Gly Gly Ile Arg Tyr Asn Gln Lys Phe
    50                  55                  60

Lys Gly Arg Phe Thr Ile Ser Val Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ile Gly Gly Tyr Tyr Asp Ser Met Asp Tyr Trp Gly Gln Gly
            100                 105                 110

Thr Leu Val Thr Val Ser Ser
        115

<210> SEQ ID NO 5
<211> LENGTH: 111
<212> TYPE: PRT
<213> ORGANISM: Artificial Sequence
<220> FEATURE:
<223> OTHER INFORMATION: Synthetic Construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Phe
            20                  25                  30

Gly Ile Asn Phe Leu Asn Trp Tyr Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Lys
                85                  90                  95

Glu Leu Pro Trp Thr Phe Gly Gly Thr Lys Val Glu Ile Lys
            100                 105                 110

<210> SEQ ID NO 6
<211> LENGTH: 119
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Thr Met Asn Trp Val Arg Gln Ala Pro Gly Lys Gly Leu Glu Trp Val
        35                  40                  45
```

Ala Leu Ile Asn Pro Tyr Asn Gly Gly Ile Arg Tyr Asn Gln Lys Phe
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ile Gly Gly Tyr Tyr Asp Ser Met Asp Tyr Trp Gly Gln Gly
             100                 105                 110

Thr Leu Val Thr Val Ser Ser
            115

<210> SEQ ID NO 7
<211> LENGTH: 111
<212> TYPE: PRT
<213> ORGANISM: Artificial Sequence
<220> FEATURE:
<223> OTHER INFORMATION: Synthetic Construct

<400> SEQUENCE: 7

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Glu Ser Val Asp Asn Phe
             20                  25                  30

Gly Ile Asn Phe Met Asn Trp Tyr Gln Gln Lys Pro Gly Gln Ala Pro
         35                  40                  45

Arg Leu Leu Ile Tyr Ala Ala Ser Asn Gln Gly Ser Gly Ile Pro Asp
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Leu Pro Trp Thr Phe Gly Gln Gly Thr Lys Val Glu Ile Lys
             100                 105                 110

<210> SEQ ID NO 8
<211> LENGTH: 119
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Thr Met Asn Trp Val Arg Gln Ala Pro Gly Gln Gly Leu Glu Trp Met
         35                  40                  45

Gly Leu Ile Asn Pro Tyr Asn Gly Gly Ile Arg Tyr Asn Gln Lys Phe
     50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ile Gly Gly Tyr Tyr Asp Ser Met Asp Tyr Trp Gly Gln Gly
             100                 105                 110

Thr Leu Val Thr Val Ser Ser
            115

<210> SEQ ID NO 9
<211> LENGTH: 111
<212> TYPE: PRT
<213> ORGANISM: Artificial Sequence
<220> FEATURE:
<223> OTHER INFORMATION: Synthetic Construct

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Pro Arg
            20                  25                  30

Gly Ile Asn Phe Leu Asn Trp Tyr Gln Gln Lys Pro Gly Lys Ala Pro
        35                  40                  45

Lys Leu Leu Ile Tyr Ala Ala Ser Asn Gln Ala Lys Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ala Leu
                85                  90                  95

Glu Leu Pro Trp Thr Phe Gly Gly Gly Thr Lys Val Glu Ile Lys
            100                 105                 110
```

<210> SEQ ID NO 10
<211> LENGTH: 119
<212> TYPE: PRT
<213> ORGANISM: Artificial Sequence
<220> FEATURE:
<223> OTHER INFORMATION: Synthetic Construct

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ala
            20                  25                  30

Thr Met Asn Trp Val Arg Gln Ala Pro Gly Gln Gly Leu Glu Trp Met
        35                  40                  45

Gly Leu Ile Asn Pro Tyr Asn Gly Gly Ile Arg Tyr Asn Gln Lys Phe
    50                  55                  60

Lys Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Gly Gly Tyr Tyr Asp Ser Met Asp Tyr Trp Gly Gln Gly
            100                 105                 110

Thr Leu Val Thr Val Ser Ser
        115
```

<210> SEQ ID NO 11
<211> LENGTH: 111
<212> TYPE: PRT
<213> ORGANISM: Artificial Sequence
<220> FEATURE:
<223> OTHER INFORMATION: Synthetic Construct

<400> SEQUENCE: 11

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Glu Ser Val Glu Pro Arg
            20                  25                  30

Gly Ile Asn Phe Leu Asn Trp Tyr Gln Gln Lys Pro Gly Lys Ala Pro
        35                  40                  45

Lys Leu Leu Ile Tyr Ala Ala Ser Gln Ala Ser Lys Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ala Leu
                85                  90                  95

Glu Leu Pro Trp Thr Phe Gly Gly Gly Thr Lys Val Glu Ile Lys
            100                 105                 110
```

<210> SEQ ID NO 12
<211> LENGTH: 119
<212> TYPE: PRT
<213> ORGANISM: Artificial Sequence
<220> FEATURE:
<223> OTHER INFORMATION: Synthetic Construct

<400> SEQUENCE: 12

```
Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Gly Ala
            20                  25                  30

Thr Met Asn Trp Val Arg Gln Ala Pro Gly Gln Gly Leu Glu Trp Met
        35                  40                  45

Gly Leu Ile Asn Pro Tyr Thr Gly Gly Ile Arg Tyr Asn Gln Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Ile Gly Gly Tyr Tyr Asp Ser Met Asp Tyr Trp Gly Gln Gly
            100                 105                 110

Thr Leu Val Thr Val Ser Ser
        115
```

<210> SEQ ID NO 13
<211> LENGTH: 111
<212> TYPE: PRT
<213> ORGANISM: Artificial Sequence
<220> FEATURE:
<223> OTHER INFORMATION: Synthetic Construct

<400> SEQUENCE: 13

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Glu Ser Val Glu Pro Arg
            20                  25                  30

Gly Ile Asn Phe Leu Asn Trp Tyr Gln Gln Lys Pro Gly Lys Ala Pro
        35                  40                  45

Lys Leu Leu Ile Tyr Ala Ala Ser Gln Ala Ser Lys Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ala Leu
                85                  90                  95
```

Glu Leu Pro Trp Thr Phe Gly Gly Gly Thr Lys Val Glu Ile Lys
                100                 105                 110

<210> SEQ ID NO 14
<211> LENGTH: 119
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ala
                20                  25                  30

Thr Met Asn Trp Val Arg Gln Ala Pro Gly Gln Gly Leu Glu Trp Met
            35                  40                  45

Gly Leu Ile Asn Pro Tyr Thr Gly Gly Ile Arg Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Gly Gly Tyr Tyr Asp Thr Met Asp Tyr Trp Gly Gln Gly
                100                 105                 110

Thr Leu Val Thr Val Ser Ser
        115

<210> SEQ ID NO 15
<211> LENGTH: 107
<212> TYPE: PRT
<213> ORGANISM: Artificial Sequence
<220> FEATURE:
<223> OTHER INFORMATION: Synthetic Construct

<400> SEQUENCE: 15

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Val Ser Gly Ile Pro Ser Arg Phe Ser Gly
        50                  55                  60

Ser Gly Ser Gly Thr Asp Phe Thr Leu Phe Ile Asn Ser Val Glu Ser
65                  70                  75                  80

Glu Asp Ile Ala Asp Tyr Tyr Cys Gln Gln Thr Tyr Ser Trp Pro Ala
                85                  90                  95

Thr Phe Gly Ala Gly Thr Lys Leu Glu Leu Lys
                100                 105

<210> SEQ ID NO 16
<211> LENGTH: 118
<212> TYPE: PRT
<213> ORGANISM: Artificial Sequence
<220> FEATURE:
<223> OTHER INFORMATION: Synthetic Construct

<400> SEQUENCE: 16

```
Gln Val Gln Leu Gln Gln Ser Gly Ala Glu Leu Met Lys Pro Gly Ala
1               5                   10                  15

Ser Val Lys Ile Ser Cys Thr Ala Thr Gly Tyr Thr Ile Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Val Thr Asn Tyr Asn Glu Lys Phe
    50                  55                  60

Lys Gly Lys Ala Thr Phe Thr Ala Asp Thr Ser Asn Thr Ala Tyr
65                  70                  75                  80

Met Gln Leu Ser Ser Leu Thr Ser Glu Asp Ser Ala Val Tyr Ser Cys
                85                  90                  95

Ala Arg Lys Gly Thr Tyr Tyr Ala Met Asp Tyr Trp Gly Gln Gly Thr
            100                 105                 110

Ser Val Thr Val Ser Ser
            115
```

<210> SEQ ID NO 17
<211> LENGTH: 107
<212> TYPE: PRT
<213> ORGANISM: Artificial Sequence
<220> FEATURE:
<223> OTHER INFORMATION: Synthetic Construct

<400> SEQUENCE: 17

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Val Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Thr Tyr Ser Trp Pro Ala
                85                  90                  95

Thr Phe Gly Gln Gly Thr Lys Val Glu Ile Lys
            100                 105
```

<210> SEQ ID NO 18
<211> LENGTH: 118
<212> TYPE: PRT
<213> ORGANISM: Artificial Sequence
<220> FEATURE:
<223> OTHER INFORMATION: Synthetic Construct

<400> SEQUENCE: 18

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Val Thr Asn Tyr Asn Glu Lys Phe
    50                  55                  60

Lys Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Lys Gly Thr Tyr Tyr Ala Met Asp Tyr Trp Gly Gln Gly Thr
            100                 105                 110

Ser Val Thr Val Ser Ser
            115

<210> SEQ ID NO 19
<211> LENGTH: 107
<212> TYPE: PRT
<213> ORGANISM: Artificial Sequence
<220> FEATURE:
<223> OTHER INFORMATION: Synthetic Construct

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Val Ser Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ser Trp Pro Ala
                85                  90                  95

Thr Phe Gly Gln Gly Thr Lys Val Glu Ile Lys
            100                 105

<210> SEQ ID NO 20
<211> LENGTH: 118
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Val Thr Phe Glu Asn Glu Lys Phe
50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Gly Arg Tyr Tyr Ala Met Asp Tyr Trp Gly Gln Gly Thr
            100                 105                 110

Leu Val Thr Val Ser Ser
            115

<210> SEQ ID NO 21
<211> LENGTH: 15
<212> TYPE: PRT
```

<213> ORGANISM: Artificial Sequence
<220> FEATURE:
<223> OTHER INFORMATION: Synthetic Construct

<400> SEQUENCE: 21

Arg Ala Ser Glu Ser Val Asp Asn Phe Gly Ile Asn Phe Met Asn
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Ala Ala Ser Asn Gln Gly Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Ser Lys Glu Leu Pro Trp Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Gly Tyr Ser Phe Thr Asp Tyr
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Asp Tyr Thr Met Asn
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Gly Tyr Ser Phe Thr Asp Tyr Thr Met Asn
1               5                   10

<210> SEQ ID NO 27
<211> LENGTH: 6
<212> TYPE: PRT
<213> ORGANISM: Artificial Sequence

```
<220> FEATURE:
<223> OTHER INFORMATION: Synthetic Construct

<400> SEQUENCE: 27

Asn Pro Tyr Asn Gly Gly
1               5

<210> SEQ ID NO 28
<211> LENGTH: 17
<212> TYPE: PRT
<213> ORGANISM: Artificial Sequence
<220> FEATURE:
<223> OTHER INFORMATION: Synthetic Construct

<400> SEQUENCE: 28

Leu Ile Asn Pro Tyr Asn Gly Gly Ile Arg Tyr Asn Gln Lys Phe Lys
1               5                   10                  15

Gly

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Ile Gly Gly Tyr Tyr Asp Ser Met Asp Tyr
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Arg Ala Ser Glu Ser Val Asp Asn Phe Gly Ile Asn Phe Leu Asn
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is D or E
<220> FEATURE:
<221> NAME/KEY: MISC_FEATURE
<222> LOCATION: (8)..(8)
<223> OTHER INFORMATION: Xaa is N or P
<220> FEATURE:
<221> NAME/KEY: MISC_FEATURE
<222> LOCATION: (9)..(9)
<223> OTHER INFORMATION: Xaa is F or R
<220> FEATURE:
<221> NAME/KEY: MISC_FEATURE
<222> LOCATION: (14)..(14)
<223> OTHER INFORMATION: Xaa is M or L

<400> SEQUENCE: 31

Arg Ala Ser Glu Ser Val Xaa Xaa Xaa Gly Ile Asn Phe Xaa Asn
1               5                   10                  15
```

```
<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Gly Phe Thr Phe Ser Asp Tyr
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Gly Phe Thr Phe Ser Asp Tyr Thr Met Asn
1               5                  10

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Gly Tyr Thr Phe Thr Asp Tyr
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Gly Tyr Thr Phe Thr Asp Tyr Thr Met Asn
1               5                  10

<210> SEQ ID NO 36
<211> LENGTH: 15
<212> TYPE: PRT
<213> ORGANISM: Artificial Sequence
<220> FEATURE:
<223> OTHER INFORMATION: Synthetic Construct

<400> SEQUENCE: 36

Arg Ala Ser Glu Ser Val Asp Pro Arg Gly Ile Asn Phe Leu Asn
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ala Ala Ser Asn Gln Ala Lys
1               5

<210> SEQ ID NO 38
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gln Gln Ala Leu Glu Leu Pro Trp Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

Gly Tyr Thr Phe Thr Gly Ala
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct

<400> SEQUENCE: 40

Gly Ala Thr Met Asn
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Gly Tyr Thr Phe Thr Gly Ala Thr Met Asn
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Synthetic Construct

<400> SEQUENCE: 42

Arg Ala Ser Glu Ser Val Glu Pro Arg Gly Ile Asn Phe Leu Asn
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: Synthetic Construct

<400> SEQUENCE: 43

Ala Ala Ser Gln Ala Ser Lys
1               5

<210> SEQ ID NO 44
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 44

Asn Pro Tyr Thr Gly Gly
1               5

<210> SEQ ID NO 45
<211> LENGTH: 17
<212> TYPE: PRT
<213> ORGANISM: Artificial Sequence
<220> FEATURE:
<223> OTHER INFORMATION: Synthetic Construct

<400> SEQUENCE: 45

Leu Ile Asn Pro Tyr Thr Gly Gly Ile Arg Tyr Asn Gln Lys Phe Lys
1               5                   10                  15

Gly

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Ile Gly Gly Tyr Tyr Asp Thr Met Asp Tyr
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic Construct

<400> SEQUENCE: 47

Arg Ala Ser Gln Ser Ile Gly Thr Ser Ile His
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Tyr Ala Ser Glu Ser Val Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Gln Gln Thr Tyr Ser Trp Pro Ala Thr
1               5

<210> SEQ ID NO 50
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Gly Tyr Thr Ile Ser Arg Tyr Trp Ile Glu
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

Gly Tyr Thr Ile Ser Arg Tyr
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Construct

<400> SEQUENCE: 52

Arg Tyr Trp Ile Glu
1               5

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Glu Ile Leu Pro Gly Ser Gly Val Thr Asn Tyr Asn Glu Lys Phe Lys
1               5                   10                  15

Gly

<210> SEQ ID NO 54
<211> LENGTH: 6
<212> TYPE: PRT
<213> ORGANISM: Artificial Sequence
<220> FEATURE:
<223> OTHER INFORMATION: Synthetic Construct

<400> SEQUENCE: 54

Leu Pro Gly Ser Gly Val
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Lys Gly Thr Tyr Tyr Ala Met Asp Tyr
1               5
```

```
<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Gly Gly Thr Phe Ser Arg Tyr Trp Ile Glu
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct

<400> SEQUENCE: 57

Gly Gly Thr Phe Ser Arg Tyr
1               5

<210> SEQ ID NO 58
<211> LENGTH: 17
<212> TYPE: PRT
<213> ORGANISM: Artificial Sequence
<220> FEATURE:
<223> OTHER INFORMATION: Synthetic Construct

<400> SEQUENCE: 58

Glu Ile Leu Pro Gly Ser Gly Val Thr Phe Glu Asn Glu Lys Phe Lys
1               5                   10                  15

Gly

<210> SEQ ID NO 59
<211> LENGTH: 6
<212> TYPE: PRT
<213> ORGANISM: Artificial Sequence
<220> FEATURE:
<223> OTHER INFORMATION: Synthetic Construct

<400> SEQUENCE: 59

Leu Pro Gly Ser Gly Val
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic Construct

<400> SEQUENCE: 60

Lys Gly Arg Tyr Tyr Ala Met Asp Tyr
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is N or Q
<220> FEATURE:
<221> NAME/KEY: MISC_FEATURE
```

```
<222> LOCATION: (5)..(5)
<223> OTHER INFORMATION: Xaa is Q or A
<220> FEATURE:
<221> NAME/KEY: MISC_FEATURE
<222> LOCATION: (6)..(6)
<223> OTHER INFORMATION: Xaa is G, A, or S
<220> FEATURE:
<221> NAME/KEY: MISC_FEATURE
<222> LOCATION: (7)..(7)
<223> OTHER INFORMATION: Xaa is S or K

<400> SEQUENCE: 61

Ala Ala Ser Xaa Xaa Xaa Xaa
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is S or A
<220> FEATURE:
<221> NAME/KEY: MISC_FEATURE
<222> LOCATION: (4)..(4)
<223> OTHER INFORMATION: Xaa is K or L

<400> SEQUENCE: 62

Gln Gln Xaa Xaa Glu Leu Pro Trp Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Y or F
<220> FEATURE:
<221> NAME/KEY: MISC_FEATURE
<222> LOCATION: (3)..(3)
<223> OTHER INFORMATION: Xaa is S or T
<220> FEATURE:
<221> NAME/KEY: MISC_FEATURE
<222> LOCATION: (5)..(5)
<223> OTHER INFORMATION: Xaa is T or S
<220> FEATURE:
<221> NAME/KEY: MISC_FEATURE
<222> LOCATION: (6)..(6)
<223> OTHER INFORMATION: Xaa is D or G
<220> FEATURE:
<221> NAME/KEY: MISC_FEATURE
<222> LOCATION: (7)..(7)
<223> OTHER INFORMATION: Xaa is Y or A

<400> SEQUENCE: 63

Gly Xaa Xaa Phe Xaa Xaa Xaa
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (1)..(1)
<223> OTHER INFORMATION: Xaa is D or G
<220> FEATURE:
<221> NAME/KEY: MISC_FEATURE
<222> LOCATION: (2)..(2)
<223> OTHER INFORMATION: Xaa is Y or A

<400> SEQUENCE: 64

Xaa Xaa Thr Met Asn
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Y or F
<220> FEATURE:
<221> NAME/KEY: MISC_FEATURE
<222> LOCATION: (3)..(3)
<223> OTHER INFORMATION: Xaa is S or T
<220> FEATURE:
<221> NAME/KEY: MISC_FEATURE
<222> LOCATION: (5)..(5)
<223> OTHER INFORMATION: Xaa is T or S
<220> FEATURE:
<221> NAME/KEY: MISC_FEATURE
<222> LOCATION: (6)..(6)
<223> OTHER INFORMATION: Xaa is D or G
<220> FEATURE:
<221> NAME/KEY: MISC_FEATURE
<222> LOCATION: (7)..(7)
<223> OTHER INFORMATION: Xaa is Y or A

<400> SEQUENCE: 65

Gly Xaa Xaa Phe Xaa Xaa Xaa Thr Met Asn
1               5                   10

<210> SEQ ID NO 66
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is N or T

<400> SEQUENCE: 66

Asn Pro Tyr Xaa Gly Gly
1               5

<210> SEQ ID NO 67
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is N or T

<400> SEQUENCE: 67

Leu Ile Asn Pro Tyr Xaa Gly Gly Ile Arg Tyr Asn Gln Lys Phe Lys
1               5                   10                  15
```

Gly

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is S or T

<400> SEQUENCE: 68

Ile Gly Gly Tyr Tyr Asp Xaa Met Asp Tyr
1               5                   10

<210> SEQ ID NO 69
<211> LENGTH: 113
<212> TYPE: PRT
<213> ORGANISM: Artificial Sequence
<220> FEATURE:
<223> OTHER INFORMATION: Synthetic Construct

<400> SEQUENCE: 69

Asp Ile Val Met Thr Gln Ser Pro Ser Ser Leu Ala Val Ser Ala Gly
1               5                   10                  15

Glu Thr Val Thr Ile Asn Cys Lys Ser Ser Gln Ser Leu Leu Tyr Ser
            20                  25                  30

Gly Asn Gln Lys Ser Tyr Leu Ala Trp Tyr Gln Gln Lys Pro Gly Gln
        35                  40                  45

Ser Pro Lys Leu Leu Ile Tyr Trp Ala Ser Pro Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Met Ala Thr Tyr Tyr Cys Gln Gln
                85                  90                  95

Tyr Tyr Asp Ala Pro Pro Thr Phe Gly Gly Gly Thr Lys Leu Glu Ile
            100                 105                 110

Lys

<210> SEQ ID NO 70
<211> LENGTH: 119
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Asp Gly Val Leu Val Gln Pro Gly Lys
1               5                   10                  15

Ser Leu Thr Leu Ser Cys Ala Ala Ser Gly Phe Thr Phe Ser Asp Tyr
            20                  25                  30

Tyr Met Ala Trp Val Arg Gln Ala Pro Thr Lys Gly Leu Glu Trp Val
        35                  40                  45

Ala Thr Ile Ser Tyr Asp Asp Ile Thr Thr Phe Tyr Arg Asp Ser Val
    50                  55                  60

Lys Gly Arg Phe Thr Ile Ser Arg Asp Thr Ala Lys Ser Thr Leu Tyr
65                  70                  75                  80

Leu Gln Met Asp Ser Leu Arg Ser Glu Asp Thr Ala Tyr Tyr Cys
                85                  90                  95

Thr Arg Gly Leu Gln Trp Pro Tyr Val Met Asp Ala Trp Gly Gln Gly
            100                 105                 110

Ala Leu Val Thr Val Ser Ser
        115

<210> SEQ ID NO 71
<211> LENGTH: 106
<212> TYPE: PRT
<213> ORGANISM: Artificial Sequence
<220> FEATURE:
<223> OTHER INFORMATION: Synthetic Construct

<400> SEQUENCE: 71

Glu Ile Val Leu Thr Gln Ser Pro Thr Thr Met Ala Ala Ser Pro Gly
1               5                   10                  15

Glu Lys Val Thr Ile Thr Cys Arg Ala Ser Ser Ser Leu Asn Tyr Met
            20                  25                  30

His Trp Phe Gln Gln Lys Ser Gly Thr Ser Pro Lys Pro Trp Ile Tyr
        35                  40                  45

Asp Thr Ser Glu Leu Ala Ser Gly Val Pro Asp Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Leu Gln Lys Asn Gly Tyr Pro Leu Thr
                85                  90                  95

Phe Gly Ser Gly Thr Lys Leu Glu Ile Lys
            100                 105

<210> SEQ ID NO 72
<211> LENGTH: 123
<212> TYPE: PRT
<213> ORGANISM: Artificial Sequence
<220> FEATURE:
<223> OTHER INFORMATION: Synthetic Construct

<400> SEQUENCE: 72

Glu Ala Gln Leu Val Glu Ser Gly Gly Gly Leu Val Gln Pro Gly Arg
1               5                   10                  15

Ser Leu Lys Leu Ser Cys Glu Ala Ser Gly Phe Thr Phe Thr Lys Tyr
            20                  25                  30

Gly Met Ala Trp Val Arg Gln Ala Pro Thr Lys Gly Leu Glu Trp Val
        35                  40                  45

Ala Ser Ile Ile Asn Ser Gly Gly Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Thr Asp Tyr Tyr Asp Gly Ser Tyr His Ser Asp Val Val Asp Ala
            100                 105                 110

Trp Gly Gln Gly Val Leu Val Thr Val Ser Ser
        115                 120

<210> SEQ ID NO 73
<211> LENGTH: 17
<212> TYPE: PRT
<213> ORGANISM: Artificial Sequence
<220> FEATURE:
<223> OTHER INFORMATION: Synthetic Construct

```
<400> SEQUENCE: 73

Lys Ser Ser Gln Ser Leu Leu Tyr Ser Gly Asn Gln Lys Ser Tyr Leu
1               5                   10                  15
Ala

<210> SEQ ID NO 74
<211> LENGTH: 7
<212> TYPE: PRT
<213> ORGANISM: Artificial Sequence
<220> FEATURE:
<223> OTHER INFORMATION: Synthetic Construct

<400> SEQUENCE: 74

Trp Ala Ser Pro Arg Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Construct

<400> SEQUENCE: 75

Gln Gln Tyr Tyr Asp Ala Pro Pro Thr
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic Construct

<400> SEQUENCE: 76

Asp Tyr Tyr Met Ala
1               5

<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Gly Phe Thr Phe Ser Asp Tyr Tyr Met Ala
1               5                   10

<210> SEQ ID NO 78
<211> LENGTH: 6
<212> TYPE: PRT
<213> ORGANISM: Artificial Sequence
<220> FEATURE:
<223> OTHER INFORMATION: Synthetic Construct

<400> SEQUENCE: 78

Ser Tyr Asp Asp Ile Thr
1               5

<210> SEQ ID NO 79
<211> LENGTH: 17
<212> TYPE: PRT
<213> ORGANISM: Artificial Sequence
<220> FEATURE:
```

<223> OTHER INFORMATION: Synthetic Construct

<400> SEQUENCE: 79

Thr Ile Ser Tyr Asp Asp Ile Thr Thr Phe Tyr Arg Asp Ser Val Lys
1               5                   10                  15
Gly

<210> SEQ ID NO 80
<211> LENGTH: 10
<212> TYPE: PRT
<213> ORGANISM: Artificial Sequence
<220> FEATURE:
<223> OTHER INFORMATION: Synthetic Construct

<400> SEQUENCE: 80

Gly Leu Gln Trp Pro Tyr Val Met Asp Ala
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Arg Ala Ser Ser Ser Leu Asn Tyr Met His
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Synthetic Construct

<400> SEQUENCE: 82

Asp Thr Ser Glu Leu Ala Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Construct

<400> SEQUENCE: 83

Leu Gln Lys Asn Gly Tyr Pro Leu Thr
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct

<400> SEQUENCE: 84

Gly Phe Thr Phe Thr Lys Tyr Gly Met Ala
1               5                   10

<210> SEQ ID NO 85
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 85

Lys Tyr Gly Met Ala
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Construct

<400> SEQUENCE: 86

Gly Phe Thr Phe Thr Lys Tyr
1               5

<210> SEQ ID NO 87
<211> LENGTH: 14
<212> TYPE: PRT
<213> ORGANISM: Artificial Sequence
<220> FEATURE:
<223> OTHER INFORMATION: Synthetic Construct

<400> SEQUENCE: 87

Asp Tyr Tyr Asp Gly Ser Tyr His Ser Asp Val Val Asp Ala
1               5                  10

<210> SEQ ID NO 88
<211> LENGTH: 255
<212> TYPE: DNA
<213> ORGANISM: Artificial Sequence
<220> FEATURE:
<223> OTHER INFORMATION: Synthetic Construct

<400> SEQUENCE: 88
gatattgtcc tcacccaatc ccccgcttcg ctcgccgtgt cactgggcca gagagccacc    60
atttcctgtc gggcatccga aagcgtggac aatttcggga tcaacttcat gaactggttc   120
cagcagaagt ccggacagcc tccgaaactg ttgatctacg ccgcgagcaa ccagggatcg   180
ggagtgccag cccgcttcag cggatcaggc tccggtaccg atttctccct ggacatccac   240
ccgatggagg aggac                                                    255

<210> SEQ ID NO 89
<211> LENGTH: 255
<212> TYPE: DNA
<213> ORGANISM: Artificial Sequence
<220> FEATURE:
<223> OTHER INFORMATION: Synthetic Construct

<400> SEQUENCE: 89
gaggtgcagc tgcagcaaag tggccccgag agagtgaaac ccggagcctc catgaagatt    60
tcttgcaagg tgagtggata cagctttacc gactacacaa tgaactgggt gaagcagtct   120
cacgggaaga acctggagtg gattggcctg atcaatcctt acaacggcgg aattagatat   180
aaccagaagt ttaaaggaaa ggcctccttg accgttgaca aaagctcaaa taccgcctac   240
atggagctgt tgtct                                                    255

<210> SEQ ID NO 90
<211> LENGTH: 255
<212> TYPE: DNA
<213> ORGANISM: Artificial Sequence
```

```
<220> FEATURE:
<223> OTHER INFORMATION: Synthetic Construct

<400> SEQUENCE: 90
gatattcaaa tgacccaatc cccttcttct ttgtctgcat ccgttggtga tcgtgttact     60
attacctgtc gcgcgagcga atccgtggat aacttcggta ttaactttct gaattggttt    120
caacaaaagc cgggcaaggc gccgaaactg ctgatctacg cagcgtcaaa tcagggtagc    180
ggtgttccgt cgcgcttcag cggtagcggt tccggcacgg actttacgct gacgatcagc    240
agcctgcagc cagag                                                     255

<210> SEQ ID NO 91
<211> LENGTH: 255
<212> TYPE: DNA
<213> ORGANISM: Artificial Sequence
<220> FEATURE:
<223> OTHER INFORMATION: Synthetic Construct

<400> SEQUENCE: 91
gaggtccaac tggtcgagtc tggcggtggc ctggttcagc cgggtggtag cttgcgtctg     60
agctgtgcgg ttagcggtta cagctttacc gattatacca tgaactgggt ccgtcaggca    120
ccgggtaaag gtctggagtg ggtcgctctg atcaatccgt acaacggcgg catccgctac    180
aatcaaaagt ttaagggtcg cttcacgatt tcggttgata acgcgaagaa cagcctgtat    240
ctgcaaatga atagc                                                    255

<210> SEQ ID NO 92
<211> LENGTH: 255
<212> TYPE: DNA
<213> ORGANISM: Artificial Sequence
<220> FEATURE:
<223> OTHER INFORMATION: Synthetic Construct

<400> SEQUENCE: 92
gatattcaga tgacccagag cccgagcagc ctgagcgcca gcgtgggtga tcgcgtgacc     60
attacctgtc gcgcaagcga aagcgtggat aactttggca ttaactttct gaactggtat    120
cagcagaaac caggcaaagc cccaaaactg ctgatttatg ccgcaagcaa ccagggcagc    180
ggtgtgccga ccgctttag cggtagcggc agcggcaccg attttaccct gaccattagc     240
agcctgcagc cggaa                                                    255

<210> SEQ ID NO 93
<211> LENGTH: 255
<212> TYPE: DNA
<213> ORGANISM: Artificial Sequence
<220> FEATURE:
<223> OTHER INFORMATION: Synthetic Construct

<400> SEQUENCE: 93
gaagtgcagc tggttgaaag cggtggcggt ctggtgcagc caggcggtag tctgcgcctg     60
agctgtgccg caagcggctt tacctttagc gattatacca tgaactgggt cgccaggca    120 ccaggcaaag cctggaatg gtggccctg attaacccgt ataacggtgg cattcgctat    180
aaccagaaat tcaaaggtcg ctttaccatc agtcgcgata acgccaaaaa cagcctgtat    240
ctgcagatga acagc                                                    255

<210> SEQ ID NO 94
<211> LENGTH: 255
<212> TYPE: DNA
```

<213> ORGANISM: Artificial Sequence
<220> FEATURE:
<223> OTHER INFORMATION: Synthetic Construct

<400> SEQUENCE: 94

```
gaaattgtgc tgacccagag cccaggcacc ctgagcctga gcccaggtga acgcgcaacc    60
ctgagctgtc gcgcaagcga aagcgtggat aactttggca ttaacttcat gaactggtat   120
cagcagaaac caggccaggc accacgcctg ctgatttatg ccgcaagcaa ccagggcagc   180
ggcattccgg atcgctttag cggcagcggt agcggcaccg attttaccct gaccattagt   240
cgcctggaac cggaa                                                   255
```

<210> SEQ ID NO 95
<211> LENGTH: 255
<212> TYPE: DNA
<213> ORGANISM: Artificial Sequence
<220> FEATURE:
<223> OTHER INFORMATION: Synthetic Construct

<400> SEQUENCE: 95

```
caggttcagc tggtgcagag cggtgccgaa gtgaaaaaac cgggtgccag cgtgaaagtg    60
agctgcaaag ccagcggcta tacctttacc gattatacca tgaactgggt tcgccaagca   120
ccaggtcagg gcctggaatg gatgggcctg attaacccgt ataacggtgg cattcgctat   180
aaccagaaat tcaaaggtcg cgtgaccatg acccgcgata ccagcaccag caccgtgtat   240
atggaactga gcagc                                                   255
```

<210> SEQ ID NO 96
<211> LENGTH: 255
<212> TYPE: DNA
<213> ORGANISM: Artificial Sequence
<220> FEATURE:
<223> OTHER INFORMATION: Synthetic Construct

<400> SEQUENCE: 96

```
gacatccaga tgacccagag ccccagcagc ctgtctgcca gcgtgggcga cagagtgacc    60
atcacctgta gagccagcga gagcgtggac cccagaggca tcaactttct gaactggtat   120
cagcagaagc ccggcaaggc ccccaagctg ctgatctacg ccgccagcaa tcaggccaag   180
ggcgtgccca gcagatttc cggctctggc agcggcaccg acttcaccct gaccatctct   240
agcctgcagc ccgag                                                   255
```

<210> SEQ ID NO 97
<211> LENGTH: 255
<212> TYPE: DNA
<213> ORGANISM: Artificial Sequence
<220> FEATURE:
<223> OTHER INFORMATION: Synthetic Construct

<400> SEQUENCE: 97

```
cagctggtgc agtctggcgc cgaagtgaag aaaccaggcg ccagcgtgaa ggtgtcctgc    60
aaggccagcg gctacacctt taccggcgcc accatgaact gggtgcgcca ggctcctgga   120
cagggcctgg aatggatggg cctgatcaac ccctacaacg gcggcatccg gtacaaccag   180
aaattcaagg gcagagtgac catgacccgg gacaccagca cctccaccgt gtacatggaa   240
ctgagcagcc tgcgg                                                   255
```

<210> SEQ ID NO 98
<211> LENGTH: 255

```
<212> TYPE: DNA
<213> ORGANISM: Artificial Sequence
<220> FEATURE:
<223> OTHER INFORMATION: Synthetic Construct

<400> SEQUENCE: 98
gacatccaaa tgacccagtc cccttcctca ctctccgctt ccgtgggcga ccgcgtgacc    60
atcacgtgtc gggcatcgga aagcgtggaa ccaagaggga ttaacttcct gaactggtac   120
cagcagaagc ctggaaaggc cccgaagctg cttatctatg ccgcgtccca agcctcaaaa   180
ggagtgccgt cgaggttctc cgggtcggga tccggaaccg acttcaccct gactattagc   240
agcctccagc ccgag                                                    255

<210> SEQ ID NO 99
<211> LENGTH: 255
<212> TYPE: DNA
<213> ORGANISM: Artificial Sequence
<220> FEATURE:
<223> OTHER INFORMATION: Synthetic Construct

<400> SEQUENCE: 99
caggtgcagc tggtgcagtc tggcgccgaa gtgaagaaac caggcgccag cgtgaaggtg    60
tcctgcaagg ccagcggcta cacctttacc ggcgccacca tgaactgggt gcgccaggct   120
cctggacagg gctggaatg gatgggcctg atcaacccct acaccggcgg catccggtac   180
aaccagaaat tcaagggcag agtgaccatg acccgggaca ccagcacctc caccgtgtac   240
atggaactga gcagc                                                    255

<210> SEQ ID NO 100
<211> LENGTH: 255
<212> TYPE: DNA
<213> ORGANISM: Artificial Sequence
<220> FEATURE:
<223> OTHER INFORMATION: Synthetic Construct

<400> SEQUENCE: 100
gacatccaaa tgacccagtc cccttcctca ctctccgctt ccgtgggcga ccgcgtgacc    60
atcacgtgtc gggcatcgga aagcgtggaa ccaagaggga ttaacttcct gaactggtac   120
cagcagaagc ctggaaaggc cccgaagctg cttatctatg ccgcgtccca agcctcaaaa   180
ggagtgccgt cgaggttctc cgggtcggga tccggaaccg acttcaccct gactattagc   240
agcctccagc ccgag                                                    255

<210> SEQ ID NO 101
<211> LENGTH: 255
<212> TYPE: DNA
<213> ORGANISM: Artificial Sequence
<220> FEATURE:
<223> OTHER INFORMATION: Synthetic Construct

<400> SEQUENCE: 101
caggtgcagc tggtgcagtc tggcgccgaa gtgaagaaac caggcgccag cgtgaaggtg    60
tcctgcaagg ccagcggcta cacctttacc ggcgccacca tgaactgggt gcgccaggct   120
cctggacagg gctggaatg gatgggcctg atcaacccct acaccggcgg catccggtac   180
aaccagaaat tcaagggcag agtgaccatg acccgggaca ccagcacctc caccgtgtac   240
atggaactga gcagc                                                    255

<210> SEQ ID NO 102
```

```
<211> LENGTH: 255
<212> TYPE: DNA
<213> ORGANISM: Artificial Sequence
<220> FEATURE:
<223> OTHER INFORMATION: Synthetic Construct

<400> SEQUENCE: 102
gacatcttgc tgactcagtc tccagccatc ctgtctgtga gtccaggaga aagagtcagt     60
ttctcctgca gggccagtca gagcattggc acaagcatac actggtatca gcaaagaaca    120
aatggttctc caaggcttct cataaagtat gcttctgagt ctgtctctgg gatcccttcc    180
aggtttagtg gcagtggatc agggacagat tttactctgt tcatcaacag tgtggagtct    240
gaagatattg cagat                                                     255

<210> SEQ ID NO 103
<211> LENGTH: 255
<212> TYPE: DNA
<213> ORGANISM: Artificial Sequence
<220> FEATURE:
<223> OTHER INFORMATION: Synthetic Construct

<400> SEQUENCE: 103
caggttcagc tgcagcagtc tggagctgag ctgatgaagc ctggggcctc agtgaagata     60
tcctgcacgg ctactggcta cacaatcagt agatattgga tagagtgggt aaagcagagg    120
cctggacatg gccttgagtg gattggagag attttacctg gaagtggtgt tactaactac    180
aatgagaagt tcaagggcaa ggccacattc actgcagata catcctccaa cacagcctac    240
atgcaactca gcagc                                                     255

<210> SEQ ID NO 104
<211> LENGTH: 255
<212> TYPE: DNA
<213> ORGANISM: Artificial Sequence
<220> FEATURE:
<223> OTHER INFORMATION: Synthetic Construct

<400> SEQUENCE: 104
gaaatcgtgc tgactcagtc acctggaacc ctctcgttgt ccccegggga aagggccact     60 ctttcctgcc gggcatccca gtcgatcgga acctccattc actggtacca gcagaagccg    120
gggcaggcgc cccggctgct catctattac gcctccgaat ccgtgtccgg catcccggat    180
agattcagcg gaagcggctc aggcaccgac tttaccctga ctatctcgcg cctggagcct    240
gaggacttcg ctgtg                                                     255

<210> SEQ ID NO 105
<211> LENGTH: 255
<212> TYPE: DNA
<213> ORGANISM: Artificial Sequence
<220> FEATURE:
<223> OTHER INFORMATION: Synthetic Construct

<400> SEQUENCE: 105
caagtgcagc tcgtccagtc cggcgccgaa gtcaagaagc ctggttcctc ggtgaaagtg     60
tcctgcaagg catcgggagg gaccttcagc cggtattgga tcgaatgggt cagacaggcg    120
cccggacagg gccttgagtg gatgggcgaa attctgccgg gatccggagt gaccaactac    180
aacgagaagt tcaagggtcg cgtgacgatc accgccgacg aatcaacttc caccgcctac    240
atggagctga gctcc                                                     255
```

<210> SEQ ID NO 106
<211> LENGTH: 255
<212> TYPE: DNA
<213> ORGANISM: Artificial Sequence
<220> FEATURE:
<223> OTHER INFORMATION: Synthetic Construct

<400> SEQUENCE: 106

```
gaaatcgtgc tgactcagtc acctggaacc ctctcgttgt ccccggggga agggccact     60
ctttcctgcc gggcatccca gtcgatcgga acctccattc actggtacca gcagaagccg    120
gggcaggcgc cccggctgct catctattac gcctccgaat ccgtgtccgg catcccggat    180
agattcagcg gaagcggctc aggcaccgac tttaccctga ctatctcgcg cctggagcct    240
gaggacttcg ctgtg                                                     255
```

<210> SEQ ID NO 107
<211> LENGTH: 255
<212> TYPE: DNA
<213> ORGANISM: Artificial Sequence
<220> FEATURE:
<223> OTHER INFORMATION: Synthetic Construct

<400> SEQUENCE: 107

```
caagtgcaac ttgtgcagtc gggagccgaa gtcaagaagc ccggttcctc cgtgaaagtg     60
tcctgcaaag cctccggcgg tacctttagc cggtactgga tcgaatgggt cagacaggcg    120
cctgggcagg gactggaatg gatggggga atcctgccgg gctccggagt gaccttcgag    180
aacgagaagt tcaagggccg cgtgaccatt accgctgacg agtcgacttc aaccgcatat    240
atggaactca gcagc                                                     255
```

<210> SEQ ID NO 108
<211> LENGTH: 137
<212> TYPE: PRT
<213> ORGANISM: Homo sapiens

<400> SEQUENCE: 108

```
Gln Arg Pro Thr Gly Gly Pro Gly Cys Gly Pro Gly Arg Leu Leu Leu
1               5                   10                  15
Gly Thr Gly Thr Asp Ala Arg Cys Cys Arg Val His Thr Thr Arg Cys
                20                  25                  30
Cys Arg Asp Tyr Pro Gly Glu Glu Cys Cys Ser Glu Trp Asp Cys Met
            35                  40                  45
Cys Val Gln Pro Glu Phe His Cys Gly Asp Pro Cys Cys Thr Thr Cys
        50                  55                  60
Arg His His Pro Cys Pro Pro Gly Gln Gly Val Gln Ser Gln Gly Lys
65                  70                  75                  80
Phe Ser Phe Gly Phe Gln Cys Ile Asp Cys Ala Ser Gly Thr Phe Ser
                85                  90                  95
Gly Gly His Glu Gly His Cys Lys Pro Trp Thr Asp Cys Thr Gln Phe
            100                 105                 110
Gly Phe Leu Thr Val Phe Pro Gly Asn Lys Thr His Asn Ala Val Cys
        115                 120                 125
Val Pro Gly Ser Pro Ala Glu Pro
    130                 135
```

<210> SEQ ID NO 109
<211> LENGTH: 218
<212> TYPE: PRT
<213> ORGANISM: Artificial Sequence
<220> FEATURE:
<223> OTHER INFORMATION: Synthetic Construct

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Glu Pro Arg
            20                  25                  30

Gly Ile Asn Phe Leu Asn Trp Tyr Gln Gln Lys Pro Gly Lys Ala Pro
        35                  40                  45

Lys Leu Leu Ile Tyr Ala Ala Ser Gln Ala Ser Lys Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ala Leu
                85                  90                  95

Glu Leu Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 110
<211> LENGTH: 217
<212> TYPE: PRT
<213> ORGANISM: Artificial Sequence
<220> FEATURE:
<223> OTHER INFORMATION: Synthetic Construct

<400> SEQUENCE: 110

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ala
            20                  25                  30

Thr Met Asn Trp Val Arg Gln Ala Pro Gly Gln Gly Leu Glu Trp Met
        35                  40                  45

Gly Leu Ile Asn Pro Tyr Thr Gly Gly Ile Arg Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ile Gly Gly Tyr Tyr Asp Ser Met Asp Tyr Trp Gly Gln Gly
            100                 105                 110

Thr Leu Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val
    210                 215

<210> SEQ ID NO 111
<211> LENGTH: 111
<212> TYPE: PRT
<213> ORGANISM: Artificial Sequence
<220> FEATURE:
<223> OTHER INFORMATION: Synthetic Construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Gln Pro Arg
            20                  25                  30

Gly Ile Asn Phe Leu Asn Trp Tyr Gln Gln Lys Pro Gly Lys Ala Pro
        35                  40                  45

Lys Leu Leu Ile Tyr Ala Ala Ser Asn Pro Ser Lys Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ala Leu
                85                  90                  95

Glu Leu Pro Trp Thr Phe Gly Gly Gly Thr Lys Val Glu Ile Lys
            100                 105                 110

<210> SEQ ID NO 112
<211> LENGTH: 119
<212> TYPE: PRT
<213> ORGANISM: Artificial Sequence
<220> FEATURE:
<223> OTHER INFORMATION: Synthetic Construct

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Val Ser Trp Val Arg Gln Ala Pro Gly Gln Gly Leu Glu Trp Met
        35                  40                  45

Gly Leu Ile Asn Pro Tyr Thr Gly Gly Ile Arg Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

```
Ala Arg Ile Gly Gly Tyr Tyr Asp Ser Met Asp Tyr Trp Gly Gln Gly
            100                 105                 110

Thr Leu Val Thr Val Ser Ser
        115

<210> SEQ ID NO 113
<211> LENGTH: 15
<212> TYPE: PRT
<213> ORGANISM: Artificial Sequence
<220> FEATURE:
<223> OTHER INFORMATION: Synthetic Construct

<400> SEQUENCE: 113

Arg Ala Ser Glu Ser Val Gln Pro Arg Gly Ile Asn Phe Leu Asn
1               5                   10                  15

<210> SEQ ID NO 114
<211> LENGTH: 7
<212> TYPE: PRT
<213> ORGANISM: Artificial Sequence
<220> FEATURE:
<223> OTHER INFORMATION: Synthetic Construct

<400> SEQUENCE: 114

Ala Ala Ser Asn Pro Ser Lys
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic Construct

<400> SEQUENCE: 115

Gly Tyr Thr Phe Thr Gly Tyr Thr Val Ser
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Synthetic Construct

<400> SEQUENCE: 116

Gly Tyr Thr Phe Thr Gly Tyr
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic Construct

<400> SEQUENCE: 117

Gly Tyr Thr Val Ser
1               5

<210> SEQ ID NO 118
<211> LENGTH: 255
<212> TYPE: DNA
<213> ORGANISM: Artificial Sequence
<220> FEATURE:
<223> OTHER INFORMATION: Synthetic Construct
```

<400> SEQUENCE: 118

```
caggtgcagc tggtgcagtc tggcgccgaa gtgaagaaac caggcgccag cgtgaaggtg    60
tcctgcaagg ccagcggcta caccttaca ggctacaccg tgtcctgggt gcgccaggct    120
cctggacagg gactggaatg gatgggcctg atcaacccct acaccggcgg catccggtac    180
aaccagaaat tcaagggcag agtgaccatg acccgggaca ccagcacctc caccgtgtac    240
atggaactga gcagc                                                    255
```

<210> SEQ ID NO 119
<211> LENGTH: 255
<212> TYPE: DNA
<213> ORGANISM: Artificial Sequence
<220> FEATURE:
<223> OTHER INFORMATION: Synthetic Construct

<400> SEQUENCE: 119

```
gacatccaaa tgacccagtc cccttcctca ctctccgctt ccgtgggcga ccgcgtgacc    60
atcacgtgtc gggcatcgga aagcgtgcaa ccaagaggga ttaacttcct gaactggtac    120
cagcagaagc ctggaaaggc cccgaagctg cttatctatg ccgcgtccaa cccgtcaaaa    180
ggagtgccgt cgaggttctc cgggtcggga tccggaaccg acttcaccct gactattagc    240
agcctccagc ccgag                                                    255
```

<210> SEQ ID NO 120
<211> LENGTH: 107
<212> TYPE: PRT
<213> ORGANISM: Artificial Sequence
<220> FEATURE:
<223> OTHER INFORMATION: Synthetic Construct

<400> SEQUENCE: 120

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Val Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Thr Tyr Ser Trp Pro Ala
                85                  90                  95

Thr Phe Gly Gln Gly Thr Lys Val Glu Ile Lys
            100                 105
```

<210> SEQ ID NO 121
<211> LENGTH: 118
<212> TYPE: PRT
<213> ORGANISM: Artificial Sequence
<220> FEATURE:
<223> OTHER INFORMATION: Synthetic Construct

<400> SEQUENCE: 121

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30
```

Trp Ile Glu Trp Val Arg Gln Ala Pro Gly Gln Gly Leu Glu Trp Met
            35                  40                  45

Gly Glu Ile Leu Pro Gly Ser Gly Val Glu Trp Tyr Asn Glu Lys Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Lys Gly Arg Gly Tyr Ala Met Asp Tyr Trp Gly Gln Gly Thr
                100                 105                 110

Ser Val Thr Val Ser Ser
            115

<210> SEQ ID NO 122
<211> LENGTH: 107
<212> TYPE: PRT
<213> ORGANISM: Artificial Sequence
<220> FEATURE:
<223> OTHER INFORMATION: Synthetic Construct

<400> SEQUENCE: 122

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Gly Thr Ser
             20                  25                  30

Ile His Trp Tyr Gln Gln Lys Pro Gly Gln Ala Pro Arg Leu Leu Ile
             35                  40                  45

Tyr Tyr Ala Ser Glu Ser Val Ser Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Thr Tyr Ser Trp Pro Ala
                 85                  90                  95

Thr Phe Gly Gln Gly Thr Lys Val Glu Ile Lys
                100                 105

<210> SEQ ID NO 123
<211> LENGTH: 118
<212> TYPE: PRT
<213> ORGANISM: Artificial Sequence
<220> FEATURE:
<223> OTHER INFORMATION: Synthetic Construct

<400> SEQUENCE: 123

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Tyr
             20                  25                  30

Trp Ile Glu Trp Val Arg Gln Ala Pro Gly Gln Gly Leu Glu Trp Met
            35                  40                  45

Gly Glu Ile Leu Pro Gly Ser Gly Val Thr Phe Glu Asn Glu Lys Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Lys Gly Arg Gly Tyr Ala Met Asp Tyr Trp Gly Gln Gly Thr
                100                 105                 110

Ser Val Thr Val Ser Ser
        115

<210> SEQ ID NO 124
<211> LENGTH: 9
<212> TYPE: PRT
<213> ORGANISM: Artificial Sequence
<220> FEATURE:
<223> OTHER INFORMATION: Synthetic Construct

<400> SEQUENCE: 124

Lys Gly Arg Gly Tyr Ala Met Asp Tyr
1               5

<210> SEQ ID NO 125
<211> LENGTH: 255
<212> TYPE: DNA
<213> ORGANISM: Artificial Sequence
<220> FEATURE:
<223> OTHER INFORMATION: Synthetic Construct

<400> SEQUENCE: 125
gaaatcgtgc tgactcagtc acctggaacc ctctcgttgt ccccgggga aagggccact     60 ctttcctgcc gggcatccca gtcgatcgga acctccattc actggtacca gcagaagccg    120
gggcaggcgc cccggctgct catctattac gcctccgaat ccgtgtccgg catcccggat    180
agattcagcg gaagcggctc aggcaccgac tttaccctga ctatctcgcg cctggagcct    240
gaggacttcg ctgtg                                                     255

<210> SEQ ID NO 126
<211> LENGTH: 255
<212> TYPE: DNA
<213> ORGANISM: Artificial Sequence
<220> FEATURE:
<223> OTHER INFORMATION: Synthetic Construct

<400> SEQUENCE: 126
caagtgcaac ttgtgcagtc gggagccgaa gtcaagaagc ccggttcctc cgtgaaagtg     60
tcctgcaaag cctccggcgg tacctttagc cggtactgga tcgaatgggt cagacaggcg    120
cctgggcagg gactggaatg gatgggggaa atcctgccgg gctccggagt gaccttcgag    180
aacgagaagt tcaagggccg cgtgaccatt accgctgacg agtcgacttc aaccgcatat    240
atggaactca gcagc                                                     255

<210> SEQ ID NO 127
<211> LENGTH: 255
<212> TYPE: DNA
<213> ORGANISM: Artificial Sequence
<220> FEATURE:
<223> OTHER INFORMATION: Synthetic Construct

<400> SEQUENCE: 127
gaaatcgtgc tgactcagtc acctggaacc ctctcgttgt ccccgggga aagggccact     60 ctttcctgcc gggcatccca gtcgatcgga acctccattc actggtacca gcagaagccg    120
gggcaggcgc cccggctgct catctattac gcctccgaat ccgtgtccgg catcccggat    180
agattcagcg gaagcggctc aggcaccgac tttaccctga ctatctcgcg cctggagcct    240
gaggacttcg ctgtg                                                     255

<210> SEQ ID NO 128

<211> LENGTH: 255
<212> TYPE: DNA
<213> ORGANISM: Artificial Sequence
<220> FEATURE:
<223> OTHER INFORMATION: Synthetic Construct

<400> SEQUENCE: 128

```
caagtgcaac ttgtgcagtc gggagccgaa gtcaagaagc ccggttcctc cgtgaaagtg      60
tcctgcaaag cctccggcgg tacctttagc cggtactgga tcgaatgggt cagacaggcg     120
cctgggcagg gactggaatg gatgggggaa atcctgccgg gctccggagt gaccttcgag     180
aacgagaagt tcaagggccg cgtgaccatt accgctgacg agtcgacttc aaccgcatat     240
atggaactca gcagc                                                     255
```

<210> SEQ ID NO 129
<211> LENGTH: 255
<212> TYPE: PRT
<213> ORGANISM: Artificial Sequence
<220> FEATURE:
<223> OTHER INFORMATION: Synthetic Construct

<400> SEQUENCE: 129

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe
                245                 250                 255
```

<210> SEQ ID NO 130
<211> LENGTH: 15

```
<212> TYPE: PRT
<213> ORGANISM: Artificial Sequence
<220> FEATURE:
<223> OTHER INFORMATION: Synthetic Construct

<400> SEQUENCE: 130

Gly Gly Gly Gly Ser Gly Gly Gly Gly Ser Gly Gly Gly Gly Ser
1               5                   10                  15
```